US011447765B2

(12) United States Patent
Ono et al.

(10) Patent No.: US 11,447,765 B2
(45) Date of Patent: Sep. 20, 2022

(54) RHAMNOSE SYNTHASE DERIVED FROM STEVIA AND GENE

(71) Applicant: SUNTORY HOLDINGS LIMITED, Osaka (JP)

(72) Inventors: Eiichiro Ono, Kyoto (JP); Misa Ochiai, Kyoto (JP); Kazunari Iwaki, Kyoto (JP); Tadayoshi Hirai, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 63 days.

(21) Appl. No.: 16/604,303

(22) PCT Filed: Apr. 11, 2018

(86) PCT No.: PCT/JP2018/015256
§ 371 (c)(1),
(2) Date: Oct. 10, 2019

(87) PCT Pub. No.: WO2018/190378
PCT Pub. Date: Oct. 18, 2018

(65) Prior Publication Data
US 2020/0123526 A1    Apr. 23, 2020

(30) Foreign Application Priority Data
Apr. 12, 2017 (JP) .............................. JP2017-079041

(51) Int. Cl.
| | | |
|---|---|---|
| *C12N 9/90* | (2006.01) | |
| *A23L 27/10* | (2016.01) | |
| *A23L 27/30* | (2016.01) | |
| *A23L 2/60* | (2006.01) | |
| *C07H 3/08* | (2006.01) | |
| *C07H 15/256* | (2006.01) | |
| *C12N 15/70* | (2006.01) | |
| *C12P 19/24* | (2006.01) | |
| *C12P 19/56* | (2006.01) | |
| *C12Q 1/6895* | (2018.01) | |

(52) U.S. Cl.
CPC .................. *C12N 9/90* (2013.01); *A23L 2/60* (2013.01); *A23L 27/11* (2016.08); *A23L 27/36* (2016.08); *C07H 3/08* (2013.01); *C07H 15/256* (2013.01); *C12N 15/70* (2013.01); *C12P 19/24* (2013.01); *C12P 19/56* (2013.01); *C12Q 1/6895* (2013.01); *C12Y 501/03013* (2013.01); *A23V 2002/00* (2013.01); *C12Q 2600/13* (2013.01)

(58) Field of Classification Search
CPC ..... C12Q 1/6895; C12Q 2600/13; A61P 3/04; A23L 27/00; A23L 27/10; A23L 27/36; A23L 2/60; A23L 27/11; A23V 2002/00; C12P 19/56; C12P 19/44; C12P 19/02; C12P 19/24; C07H 15/256; C07H 3/08; C12N 15/70; C12N 15/63; C12N 5/10; C12N 9/90; C12Y 501/03013; A61K 31/704

See application file for complete search history.

(56) References Cited

U.S. PATENT DOCUMENTS

| | | | |
|---|---|---|---|
| 9,631,215 B2 * | 4/2017 | Houghton-Larsen ........................ C12N 9/1085 |
| 9,957,539 B2 * | 5/2018 | Ono ........................ C12P 19/18 |
| 10,000,783 B2 * | 6/2018 | Ono ........................ A61Q 19/00 |
| 10,766,935 B2 * | 9/2020 | Brog ..................... C12N 15/827 |
| 2008/0064069 A1 | 3/2008 | Oka et al. |
| 2008/0187622 A1 | 8/2008 | Moriwaki et al. |
| 2014/0329281 A1 | 11/2014 | Houghton-Larsen et al. |

FOREIGN PATENT DOCUMENTS

| | | |
|---|---|---|
| EP | 1 897 951 B1 | 12/2010 |
| JP | S59-139309 A | 8/1984 |
| JP | 2008-000124 A | 1/2008 |
| JP | 2014-524247 A | 9/2014 |
| WO | WO 2005/030975 A1 | 4/2005 |
| WO | WO 2013/022989 A2 | 2/2013 |
| WO | WO 2013/137487 A1 | 9/2013 |
| WO | WO 2014/122328 A1 | 8/2014 |
| WO | 2017/115353 | 7/2017 |

OTHER PUBLICATIONS

Chica et al., Semi-rational approaches to engineering enzyme activity: combining the benefits of directed evolution and rational design. Curr. Opi. Biotechnol., 2005, vol. 16: 378-384. (Year: 2005).*
Kim et al., Cloning and Characterization of a Putative UDP-Rhamnose Synthase 1 from Populus euramericana Guinier. J. Plant Biol., 2013, vol. 56: 7-12. (Year: 2013).*
Oka et al., Functional Analysis of *Arabidopsis thaliana* RHM2/MUM4, a Multidomain Protein Involved in UDP-D-glucose to UDP-L-rhamnose Conversion. The J. Biol. Chem., 2007, vol. 282(8): 5389-5403. (Year: 2007).*
Sen et al., Developments in directed evolution for enzyme functions. Appl. Biochem. Biotechnol., 2007, vol. 143: 212-223. (Year: 2007).*
Brandle et al., "Steviol glycoside biosynthesis", Phytochemistry, 68, 2007, pp. 1855-1863.
Brandle et al., "Leaf ESTs from Stevia rebaudiana: a resource for gene discovery in diterpene synthesis", Plant Molecular Biology, vol. 50, 2002, pp. 613-622.

(Continued)

*Primary Examiner* — Ganapathirama Raghu
(74) *Attorney, Agent, or Firm* — Greenblum & Bernstein, P.L.C.

(57) ABSTRACT

The purpose of the present invention is to provide a protein, said protein having an activity of synthesizing rhamnose from glucose, and a polynucleotide encoding the same. Provided are a rhamnose synthase derived from stevia and a method for producing rhamnose from glucose using a gene. Also provided is a method for producing a steviol glycoside using the rhamnose synthase derived from stevia.

8 Claims, 12 Drawing Sheets

Specification includes a Sequence Listing.

(56) References Cited

OTHER PUBLICATIONS

Natsume et al., "The Draft Genome of Hop (*Humulus lupulus*), an Essence for Brewing", Plant & Cell Physiology, 56(3), 2015, pp. 428-441.

Oka et al., "Functional Analysis of *Arabidopsis thaliana* RHM2/MUM4, a Multidomain Protein Involved in UDP-D-glucose to UDP-L-rhamnose Conversion", The Journal of Biological Chemistry, vol. 282, No. 8, Feb. 23, 2007, pp. 5389-5403.

Reiter et al., "Molecular genetics of nucleotide sugar interconversion pathways in plants", Plant Molecular Biology, vol. 47, 2001, pp. 95-113.

Richman et al., "Functional genomics uncovers three glucosyltransferases involved in the synthesis of the major sweet glucosides of Stevia rebaudiana", The Plant Journal, 41, 2005, pp. 55-67.

ISR for PCT/2018/015256, dated Jun. 5, 2018 (w/ translation).

Database Geneseq [Online], Jun. 15, 2007, "*Arabidopsis rhamnose synthase*, RHM1.", XP002800875, retrieved from EBI accession No. GSP:AEN13737, Database accession No. AEN13737.

Database REFSEQ [Online] NCBI; Nov. 29, 2016, "Predicted: trifunctional UDP-glucose 4,6-dehydratase/UDP-4-keto-6-deoxy-D-glucose 3,5-epimerase/UDP-4-keto-L-rhamnose-reductase RHM1 [Ipomoea nil]", XP002800876, Database accession No. XP_019153924.1.

Database UniProt [Online], Nov. 22, 2017, "SubName: Full= Putative rhamnose biosynthesis 1 {ECO:0000313 I EMBL:OTG31194.1};", XP002800877, retrieved from EBI accession No. UniProt: A0A251V6Y9, Database accession No. A0A251V6Y9.

Partial Supplementary European Search Report issued in EP Patent Application No. 18784713.2, dated Jan. 22, 2021.

Database UniProtKB [Online], Jun. 26, 2013, Slotte Tanja et al: "The Capsella rubella genome and the genomic consequences of rapid mating system evolution", XP055812109, Database accession No. R0GGH0_9BRAS.

Database GSP [Online]; Sep. 30, 2010, Alexandrov N: "Plant isolated polypeptide sequence, SEQ ID 325", XP055812128, Database accession No. AYF78907.

Database GSP [Online]; Sep. 7, 2017, Pi Brog Xx et al: "Lactuca sativa exogenous polypeptide, SEQ ID 24026", XP055812083, Database accession No. BED92240.

Extended European Search Report issued in EP Patent Application No. 18784713.2, dated Aug. 4, 2021.

Notice of Reasons for Refusal issued in JP Patent Application No. 2019-512555, dated Aug. 17, 2021, along with an English translation.

* cited by examiner

Figure 1

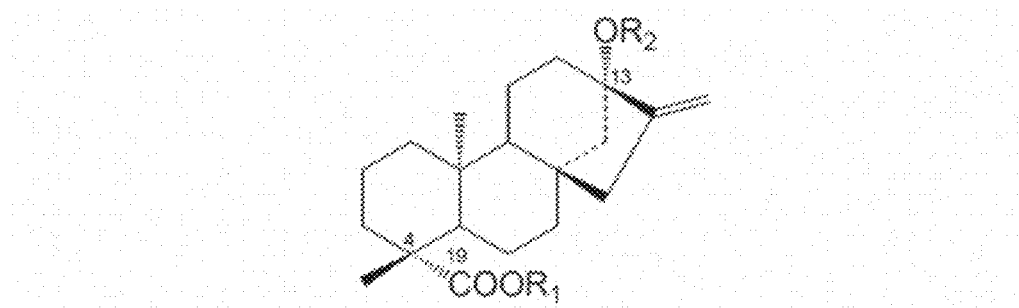

| Name | R₁ | R₂ |
|---|---|---|
| Steviol | H | H |
| Steviolmonoside | H | Glc |
| Steviolbioside | H | Glc-Glc(β2→1) |
| Dulcoside A | Glc | Glc-Rha(α2→1) |
| Rubusoside | Glc | Glc |
| Stevioside | Glc | Glc-Glc(β2→1) |
| Rebaudioside A | Glc | Glc-Glc(β2→1)<br>\|<br>Glc(β3→1) |
| Rebaudioside B | H | Glc-Glc(β2→1)<br>\|<br>Glc(β3→1) |
| Rebaudioside C (Dulcoside B) | Glc | Glc-Rha(α2→1)<br>\|<br>Glc(β3→1) |
| Rebaudioside D | Glc-Glc(β2→1) | Glc-Glc(β2→1)<br>\|<br>Glc(β3→1) |
| Rebaudioside E | Glc-Glc(β2→1) | Glc-Glc(β2→1) |
| Rebaudioside F | Glc | Glc-Xyl(β2→1)<br>\|<br>Glc(β3→1) |

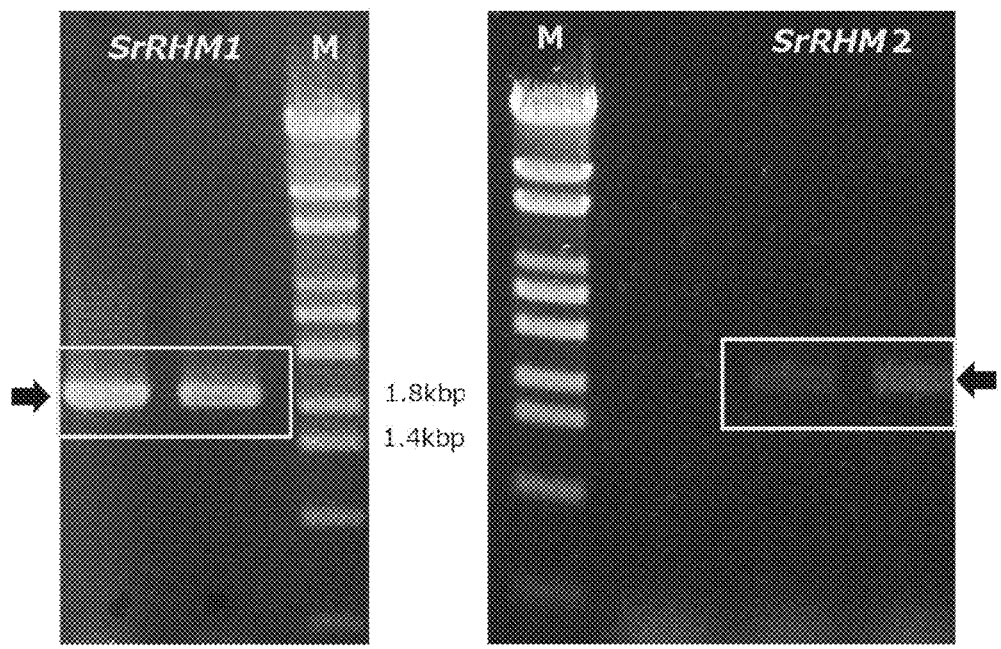
Figure 2: Amplification of SrRHM gene
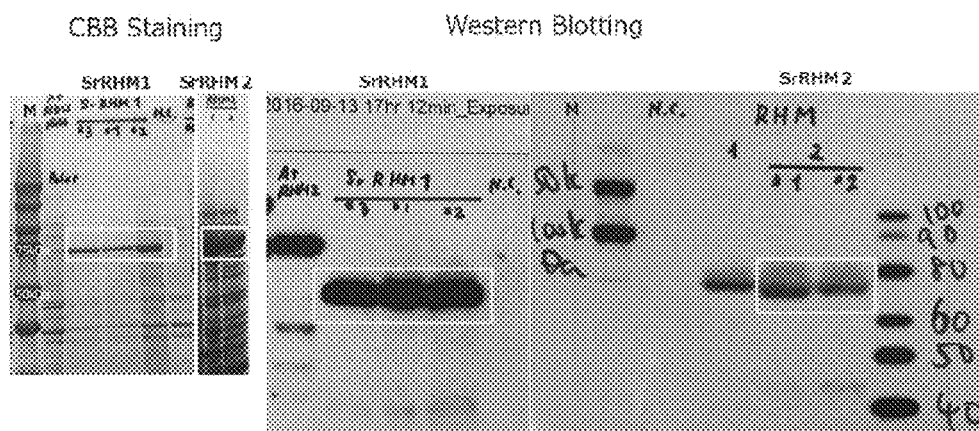
Figure 3: Expression of SrRHM recombinant proteins

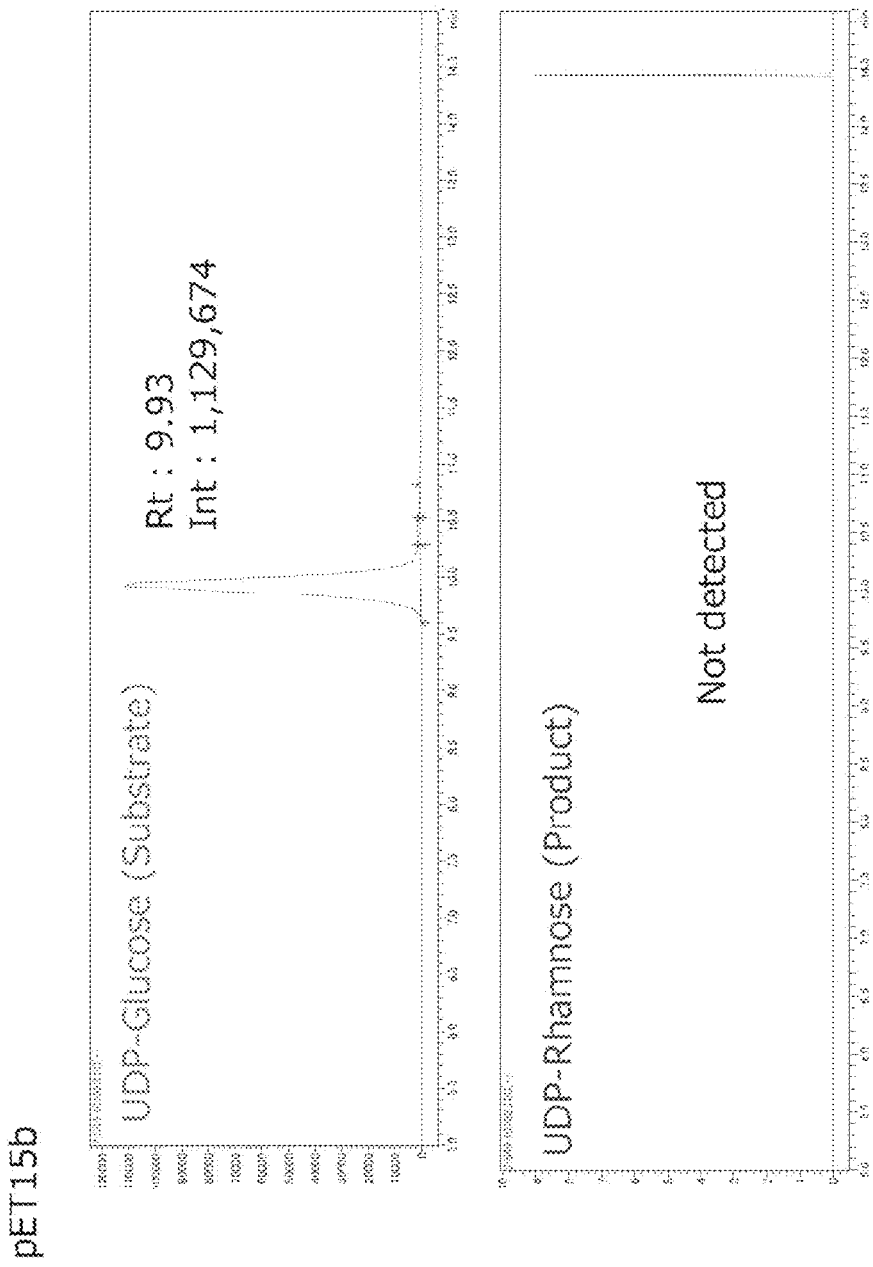
Figure 4-1: Enzymatic activity of SrRHM recombinant protein (Negative control, pET15b)

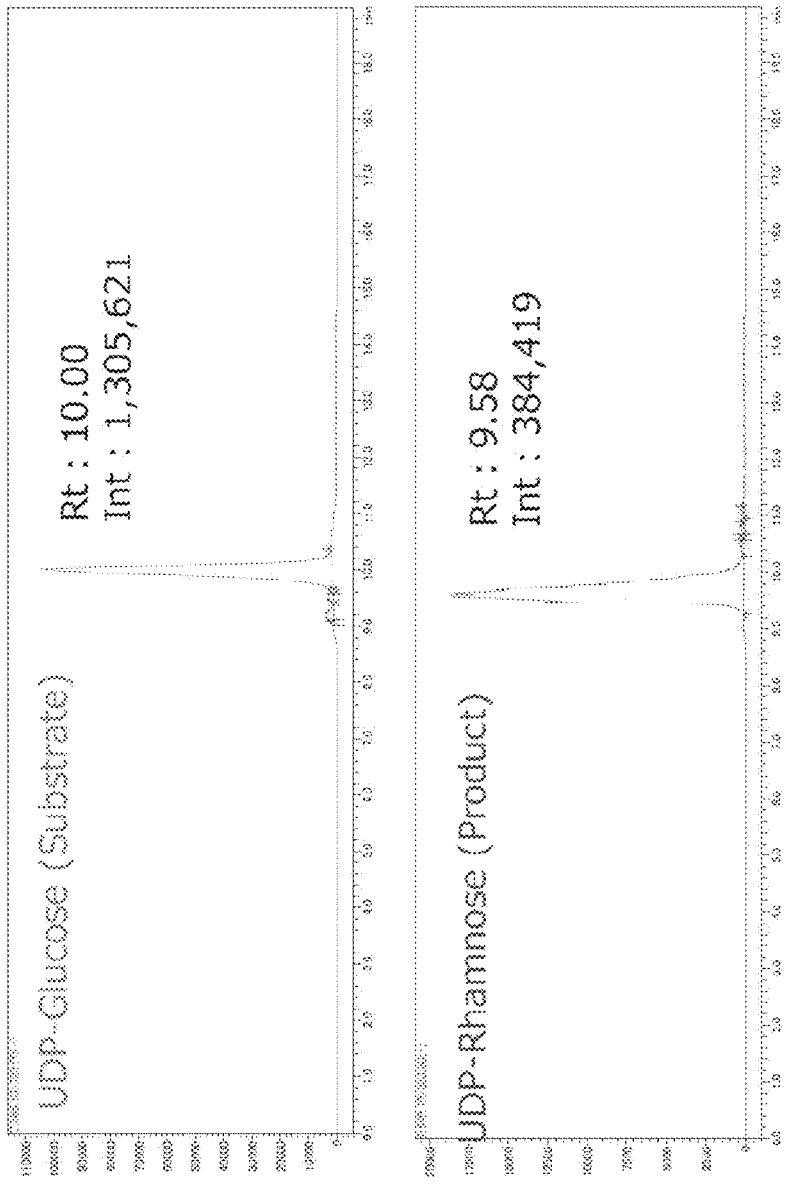
Figure 4-2: Enzymatic activity of SrRHM recombinant protein (AtRHM2, Positive control)

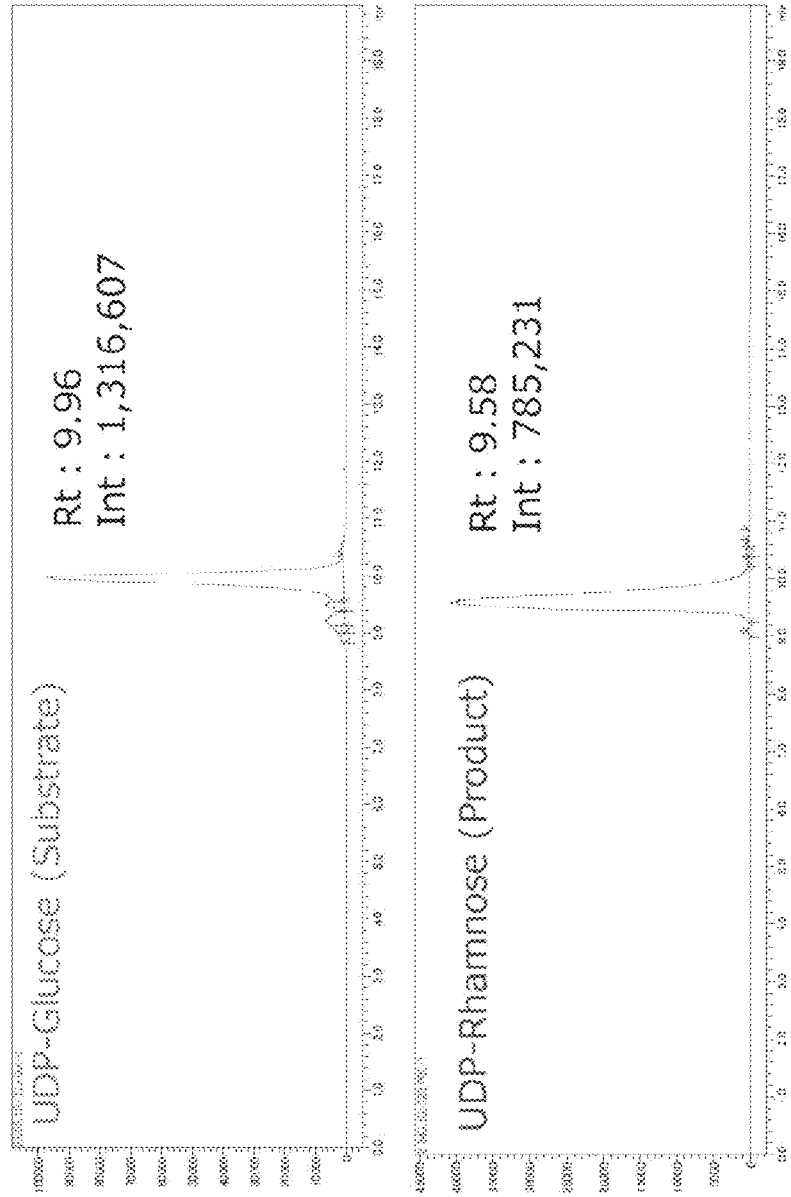
Figure 4-3: Enzymatic activity of SrRHM recombinant protein (SrRHM1#1)

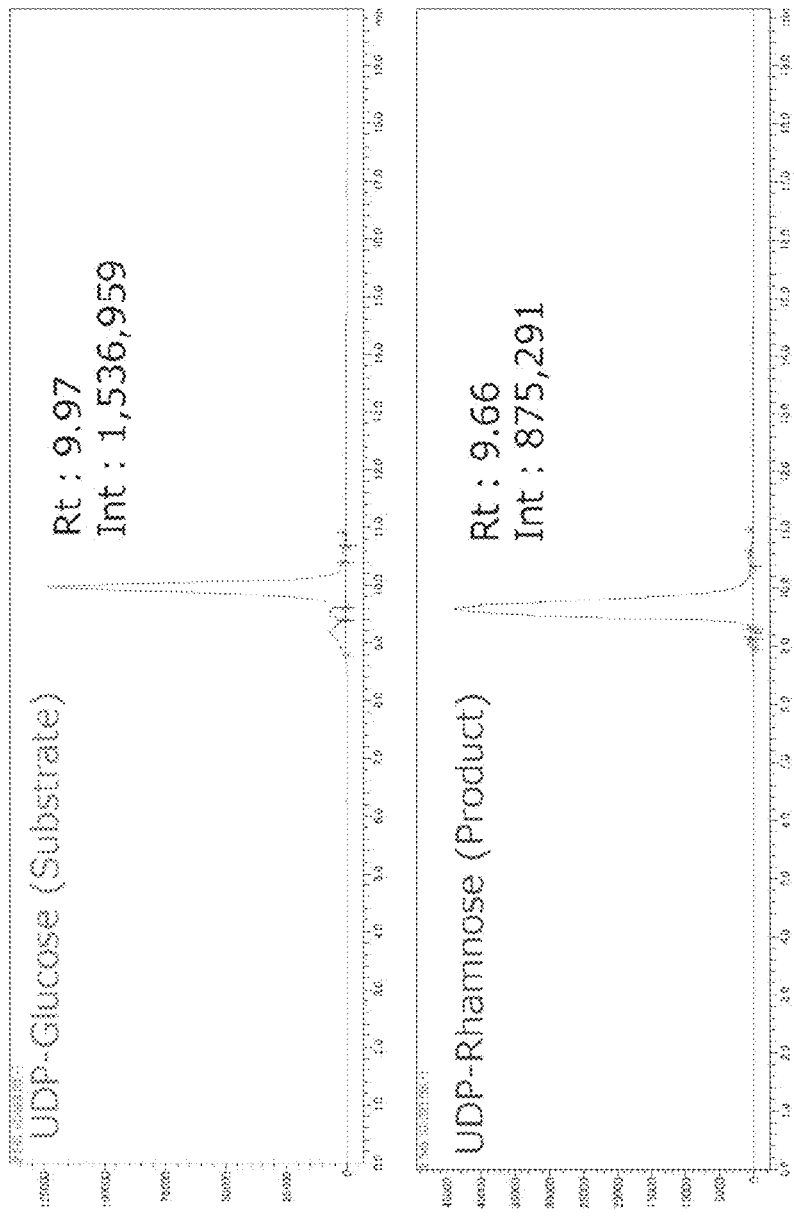
Figure 4-4: Enzymatic activity of SrRHM recombinant protein (SrRHM1#2)

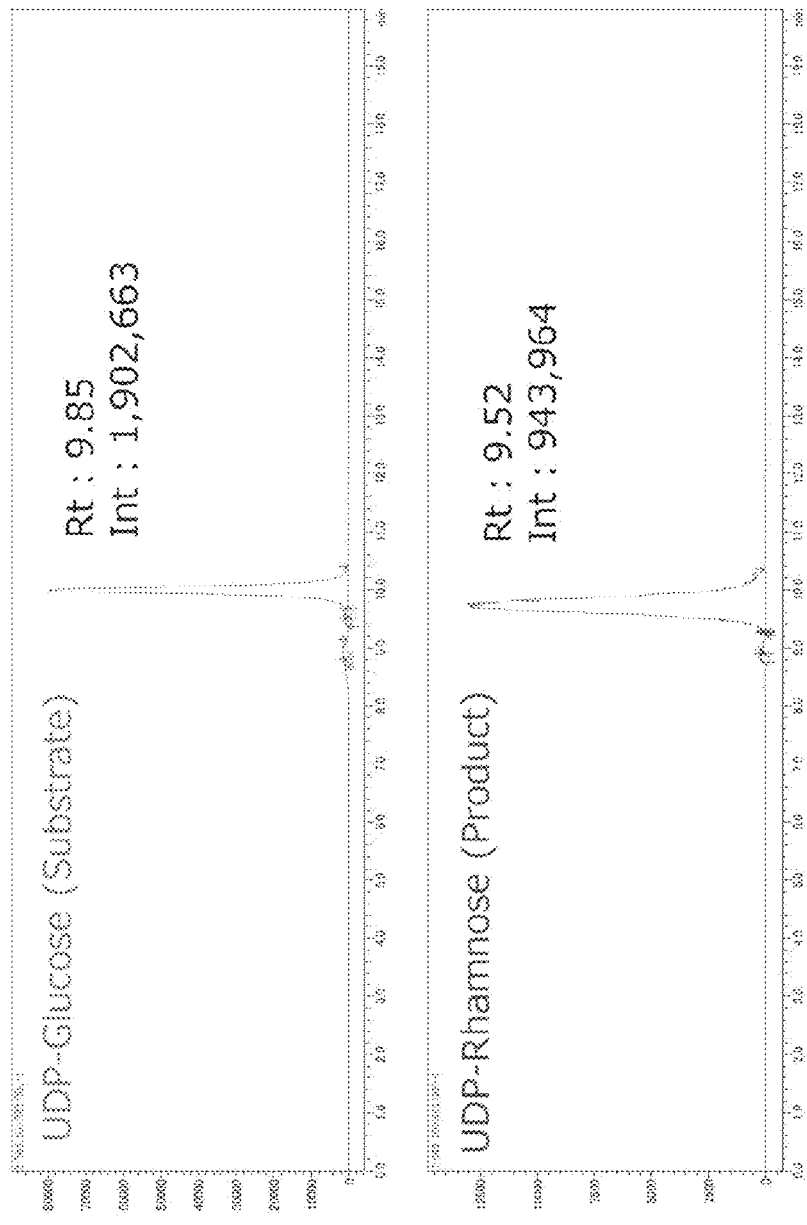
Figure 4-5: Enzymatic activity of SrRHM recombinant protein (SrRHM1#3)

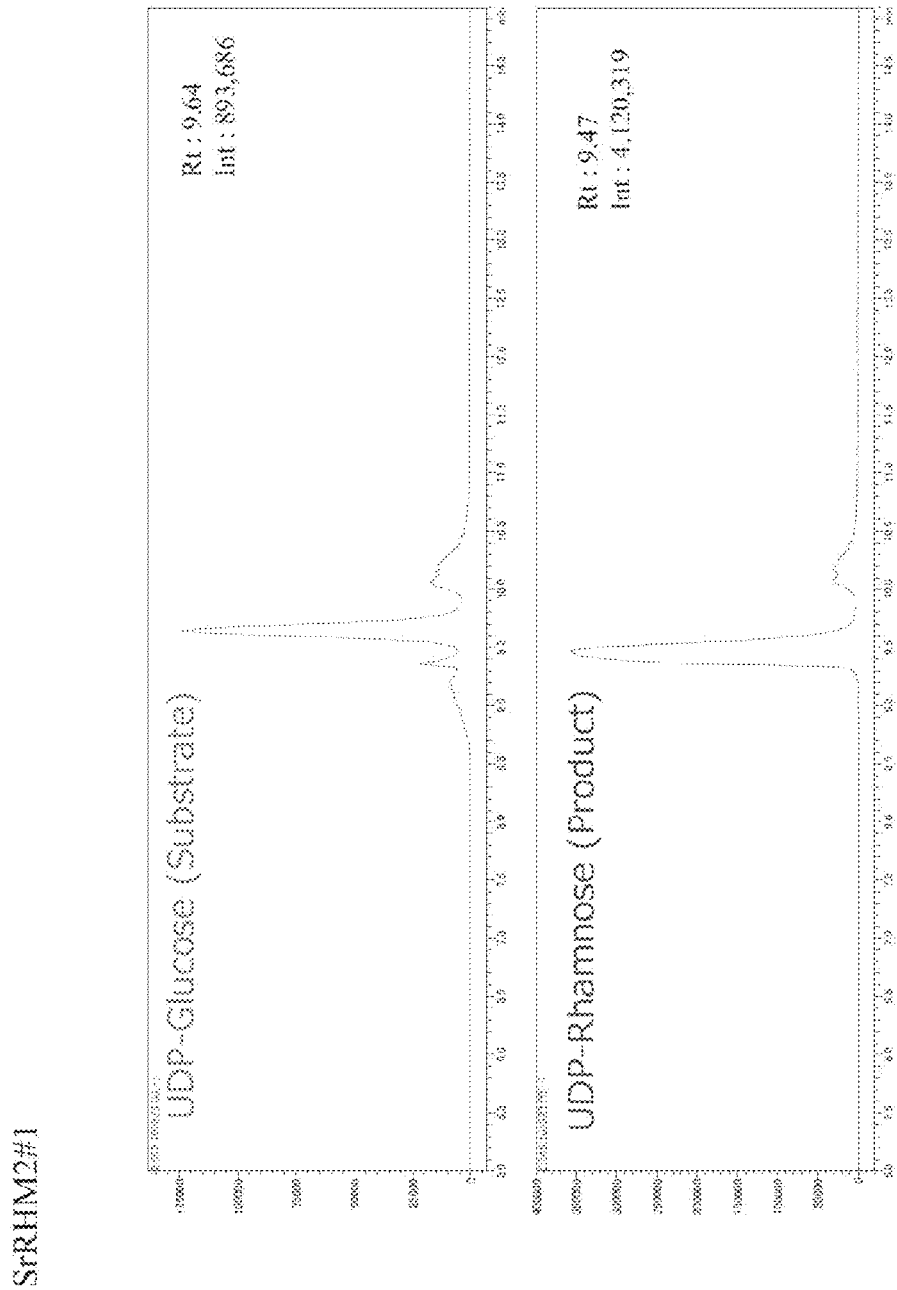
Figure 4-6: Enzymatic activity of SrRHM recombinant protein (SrRHM2#1)

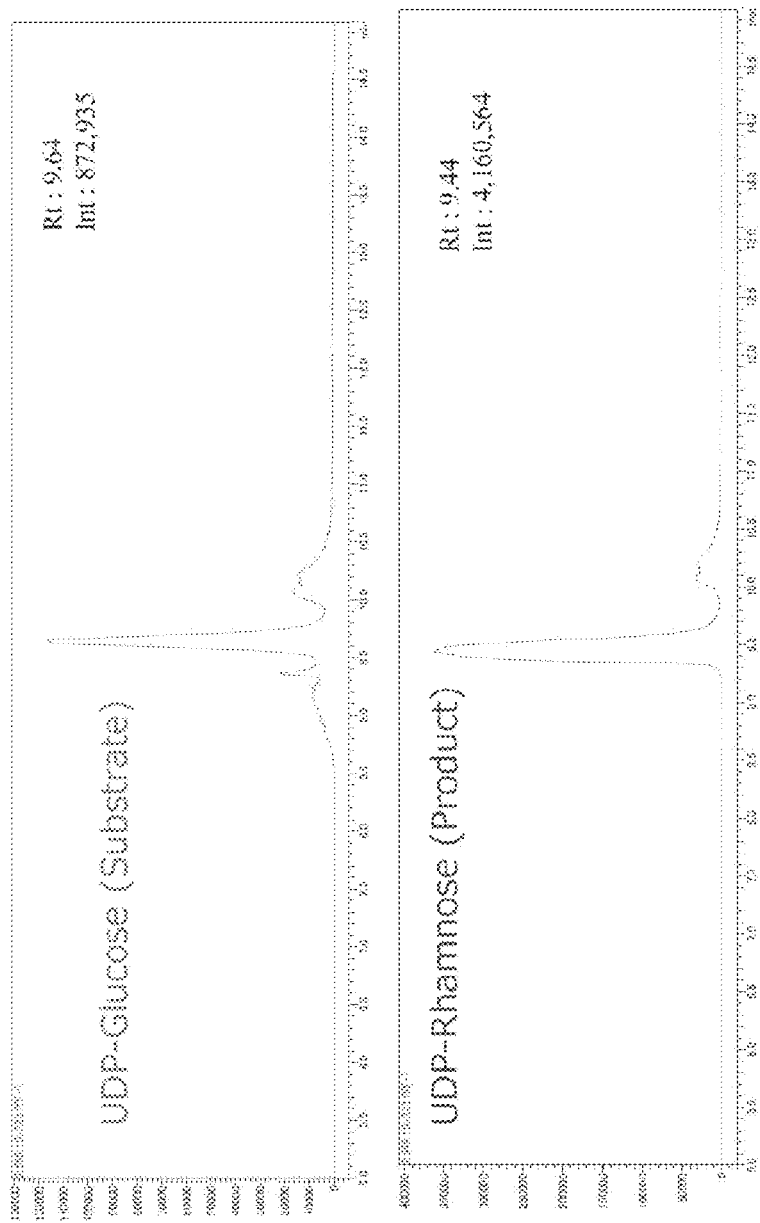
Figure 4-7: Enzymatic activity of SrRHM recombinant protein (SrRHM2#2)

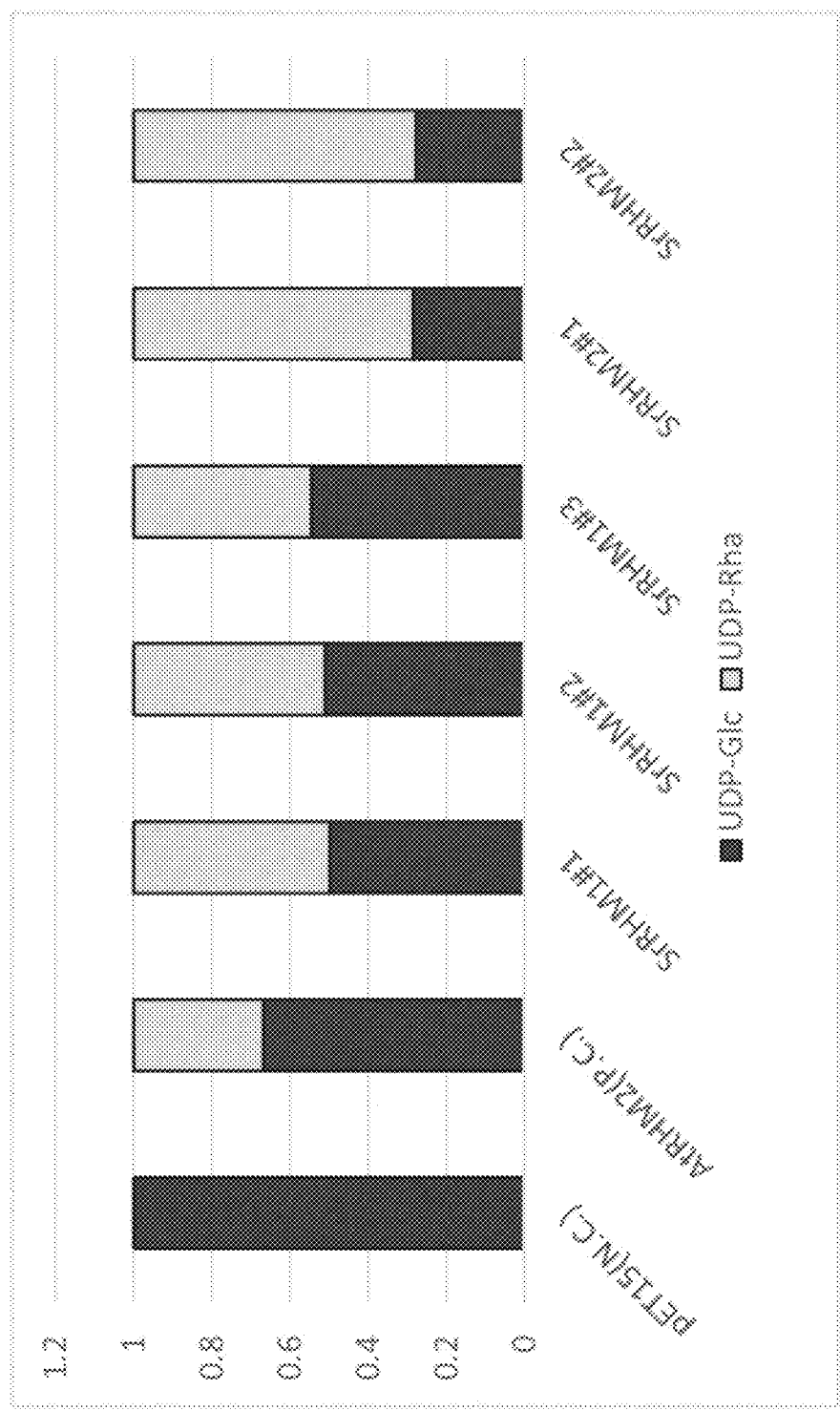
Figure 5: Specific activities of RHM recombinant proteins

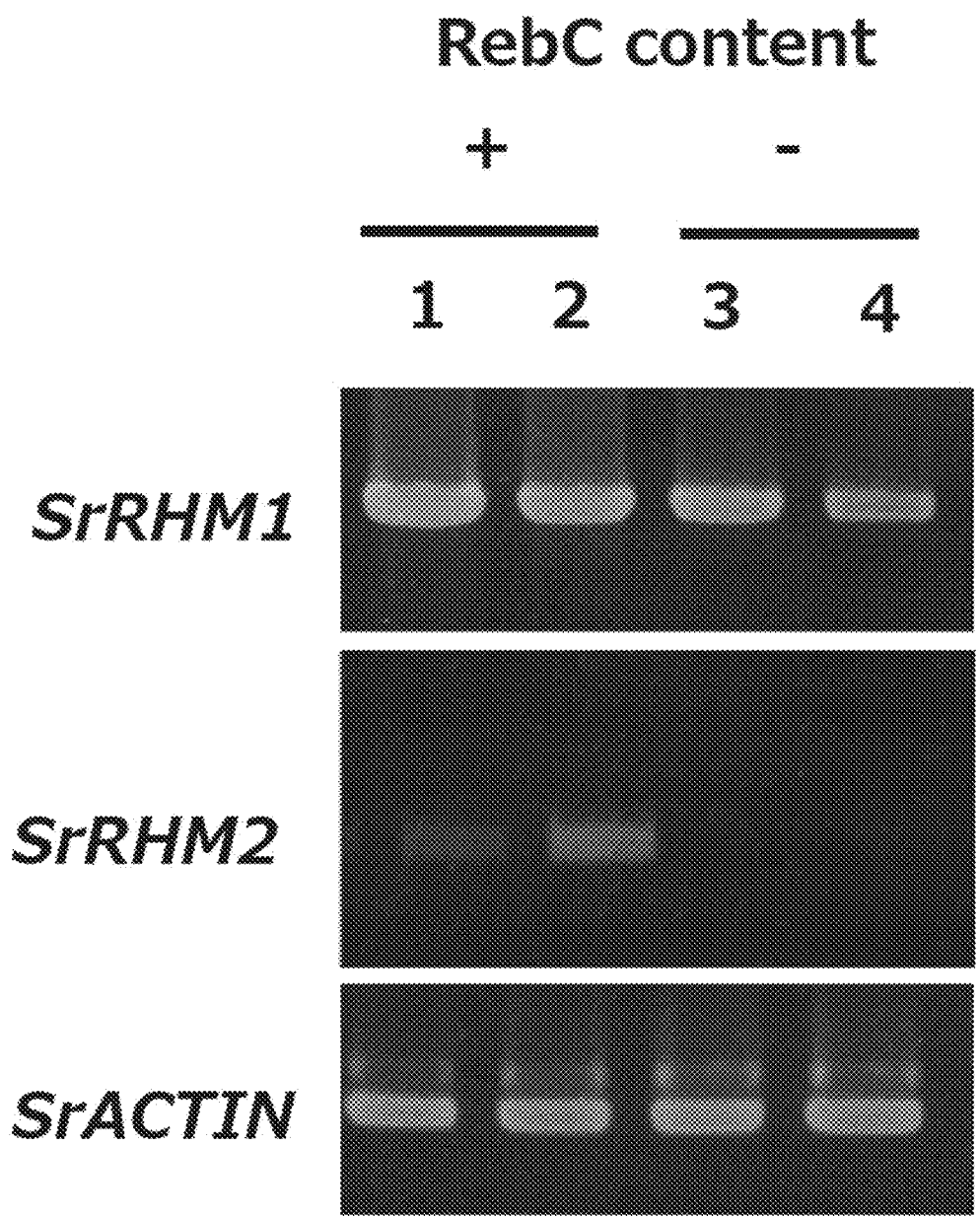
Figure 6: Expression of SrRHM genes

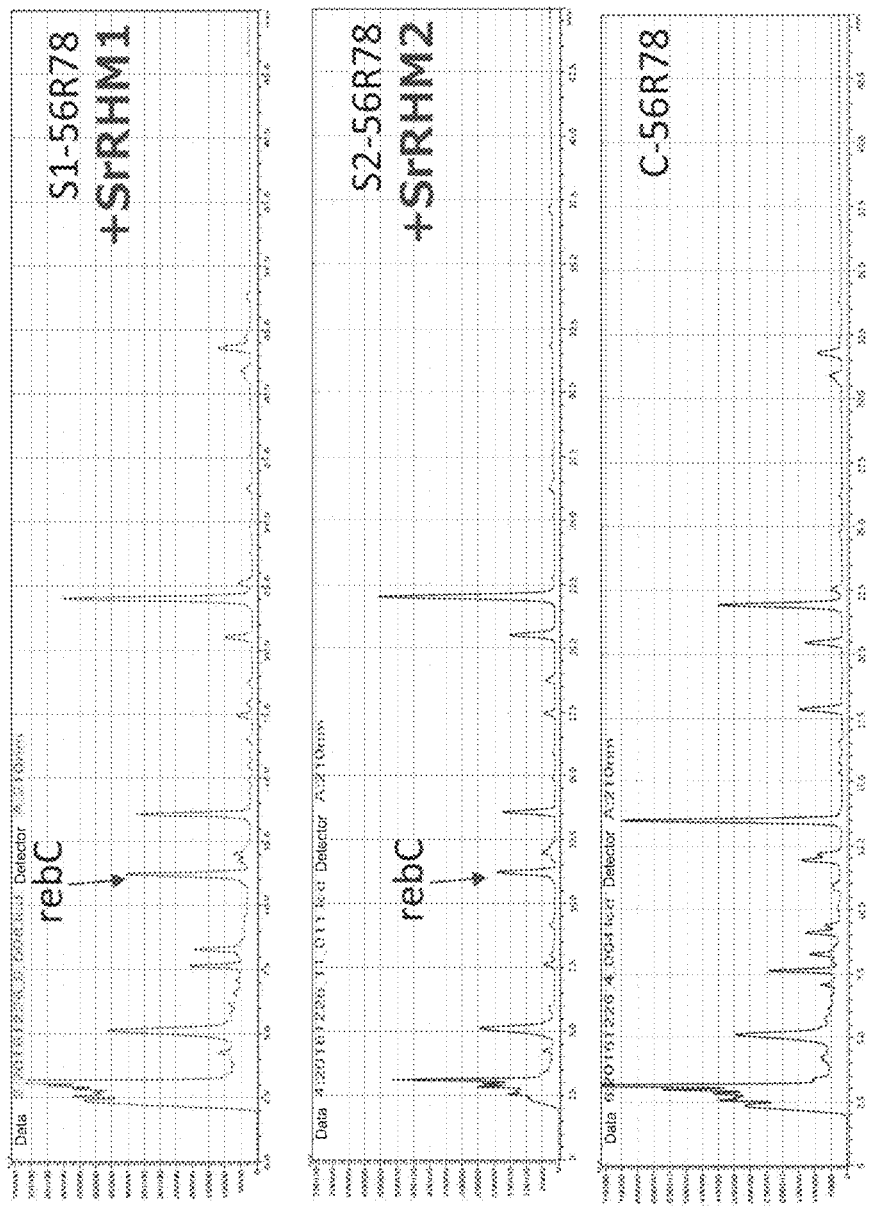
Figure 7: Coexpression of RHM from Stevia rebaudiana and UGT85C2, UGT91D2L#16, UGT74G1 and UGT76G1 in yeast

SEQUENCE LISTING

```
<160> NUMBER OF SEQ ID NOS: 56

<210> SEQ ID NO 1
<211> LENGTH: 2022
<212> TYPE: DNA
<213> ORGANISM: Stevia rebaudiana
<220> FEATURE:
<221> NAME/KEY: CDS
<222> LOCATION: (1)..(2022)

<400> SEQUENCE: 1 atg gct act tac gtg cca aag aac atc ctt atc act gga gct gca ggc       48
Met Ala Thr Tyr Val Pro Lys Asn Ile Leu Ile Thr Gly Ala Ala Gly
1               5                   10                  15 ttc atc gcc tct cat gtt gct aac cgc tta gtc aga agc tac cct gat       96
Phe Ile Ala Ser His Val Ala Asn Arg Leu Val Arg Ser Tyr Pro Asp
            20                  25                  30
```

| | | |
|---|---|---|
| tac aag att gtt gtg ctt gac aag ctt gat tat tgt tcc aat ctt aaa<br>Tyr Lys Ile Val Val Leu Asp Lys Leu Asp Tyr Cys Ser Asn Leu Lys<br>35            40            45 | | 144 |
| aac ctt aac ccc tcc aaa tca tct ccc aac ttc aag ttt gtt aaa ggc<br>Asn Leu Asn Pro Ser Lys Ser Ser Pro Asn Phe Lys Phe Val Lys Gly<br>50            55            60 | | 192 |
| gac atc ggg agc gct gat ctc gtc aac tac cta ctg atc act gaa tcc<br>Asp Ile Gly Ser Ala Asp Leu Val Asn Tyr Leu Leu Ile Thr Glu Ser<br>65            70            75            80 | | 240 |
| att gac acc ata atg cac ttt gct gca cag acc cat gtt gat aac tca<br>Ile Asp Thr Ile Met His Phe Ala Ala Gln Thr His Val Asp Asn Ser<br>85            90            95 | | 288 |
| ttc ggc aac agt ttc gag ttc aca aag aat aac atc tat gga acc cat<br>Phe Gly Asn Ser Phe Glu Phe Thr Lys Asn Asn Ile Tyr Gly Thr His<br>100           105           110 | | 336 |
| gtg ctt cta gaa gcc tgc aaa gtc act ggt cag att aga agg ttc atc<br>Val Leu Leu Glu Ala Cys Lys Val Thr Gly Gln Ile Arg Arg Phe Ile<br>115           120           125 | | 384 |
| cat gtg agc aca gat gag gtt tat ggc gaa aca gag gaa gat gct gtt<br>His Val Ser Thr Asp Glu Val Tyr Gly Glu Thr Glu Glu Asp Ala Val<br>130           135           140 | | 432 |
| gtt ggt aac cat gaa gct tca caa ctt ctt cct acc aac ccg tat tcc<br>Val Gly Asn His Glu Ala Ser Gln Leu Leu Pro Thr Asn Pro Tyr Ser<br>145           150           155           160 | | 480 |
| gcc acg aaa gct ggt gca gaa atg ctt gtt atg gct tac ggt agg tca<br>Ala Thr Lys Ala Gly Ala Glu Met Leu Val Met Ala Tyr Gly Arg Ser<br>165           170           175 | | 528 |
| tac ggg tta ccc gtg att acc acc aga ggt aac aat gtt tat ggc ccg<br>Tyr Gly Leu Pro Val Ile Thr Thr Arg Gly Asn Asn Val Tyr Gly Pro<br>180           185           190 | | 576 |
| aat caa ttt cca gag aaa cta atc cct aaa ttc atc ctt ctg gcg atg<br>Asn Gln Phe Pro Glu Lys Leu Ile Pro Lys Phe Ile Leu Leu Ala Met<br>195           200           205 | | 624 |
| aga ggt caa ccg cta cca att cat ggt gat ggt tct aat gtc aga agt<br>Arg Gly Gln Pro Leu Pro Ile His Gly Asp Gly Ser Asn Val Arg Ser<br>210           215           220 | | 672 |
| tat ctg tac tgt gaa gat gtt gca gaa gct ttt gaa gta att ctt cac<br>Tyr Leu Tyr Cys Glu Asp Val Ala Glu Ala Phe Glu Val Ile Leu His<br>225           230           235           240 | | 720 |
| aaa gga gaa gtt ggt cat gtt tac aac ata ggg acg aaa aaa gaa agg<br>Lys Gly Glu Val Gly His Val Tyr Asn Ile Gly Thr Lys Lys Glu Arg<br>245           250           255 | | 768 |
| cga gtg att gat gtt gca aaa gat atg tgc aag ctt ttc aat atg gat<br>Arg Val Ile Asp Val Ala Lys Asp Met Cys Lys Leu Phe Asn Met Asp<br>260           265           270 | | 816 |
| cct gat tca agc atc aag ttt gtt gaa aac aga ccg ttt aac gat cag<br>Pro Asp Ser Ser Ile Lys Phe Val Glu Asn Arg Pro Phe Asn Asp Gln<br>275           280           285 | | 864 |
| agg tat ttc tta gat gat gag aaa ttg aaa agt ttg ggt tgg tcc gaa<br>Arg Tyr Phe Leu Asp Asp Glu Lys Leu Lys Ser Leu Gly Trp Ser Glu<br>290           295           300 | | 912 |
| agg aca att tgg gaa gag ggt ttg aaa aag acc atc gag tgg tat acc<br>Arg Thr Ile Trp Glu Glu Gly Leu Lys Lys Thr Ile Glu Trp Tyr Thr<br>305           310           315           320 | | 960 |
| agc aac cct aat tgg tgg gga gat gtg tcg gga gca ctt ttg cct cat<br>Ser Asn Pro Asn Trp Trp Gly Asp Val Ser Gly Ala Leu Leu Pro His<br>325           330           335 | | 1008 |
| cca aga atg tta atg atg cca ggt ggc gtt gat aga ttg gtt gat gga<br>Pro Arg Met Leu Met Met Pro Gly Gly Val Asp Arg Leu Val Asp Gly<br>340           345           350 | | 1056 |

-continued

| | | |
|---|---|---|
| ccg gaa aac gcg gat ttt gac tct gct gat gtg gcg atc aat act cct<br>Pro Glu Asn Ala Asp Phe Asp Ser Ala Asp Val Ala Ile Asn Thr Pro<br>355                          360                    365 | | 1104 |
| cag att ggt gtc caa ata cct aac tcg aaa ccc agt ggc gta tcg ttt<br>Gln Ile Gly Val Gln Ile Pro Asn Ser Lys Pro Ser Gly Val Ser Phe<br>    370                        375                    380 | | 1152 |
| aag aaa cca ggt ttg aag ttt ctc att tat ggg aaa acc ggg tgg atc<br>Lys Lys Pro Gly Leu Lys Phe Leu Ile Tyr Gly Lys Thr Gly Trp Ile<br>385                        390                    395                  400 | | 1200 |
| ggt ggt tta ctc ggg aag tta tgt gat aaa caa cag att caa tac gag<br>Gly Gly Leu Leu Gly Lys Leu Cys Asp Lys Gln Gln Ile Gln Tyr Glu<br>                    405                    410                    415 | | 1248 |
| tat gga aga ggt cgg ttg gag gat cgc tca caa ctt ttg gct gat att<br>Tyr Gly Arg Gly Arg Leu Glu Asp Arg Ser Gln Leu Leu Ala Asp Ile<br>    420                        425                    430 | | 1296 |
| caa act atc aaa ccg act cat gtt ttc aat gct gct ggt gtc act ggt<br>Gln Thr Ile Lys Pro Thr His Val Phe Asn Ala Ala Gly Val Thr Gly<br>435                        440                    445 | | 1344 |
| aga ccg aat gtt gat tgg tgt gaa tct cac aag acg gaa acc att cgt<br>Arg Pro Asn Val Asp Trp Cys Glu Ser His Lys Thr Glu Thr Ile Arg<br>                    450                    455                    460 | | 1392 |
| acc aat gtt tcg ggt aca ctt aat ctt gca gat gtt tgc aga gaa aac<br>Thr Asn Val Ser Gly Thr Leu Asn Leu Ala Asp Val Cys Arg Glu Asn<br>465                        470                    475                  480 | | 1440 |
| ggt ctg tta atg atc aac ttt gct acc gga tgc ata ttt gag tat gat<br>Gly Leu Leu Met Ile Asn Phe Ala Thr Gly Cys Ile Phe Glu Tyr Asp<br>                        485                    490                    495 | | 1488 |
| gct aaa cat ccg gaa ggt tcc gga atc ggt ttt aag gaa gaa gat aca<br>Ala Lys His Pro Glu Gly Ser Gly Ile Gly Phe Lys Glu Glu Asp Thr<br>                500                    505                    510 | | 1536 |
| ccc aat ttc atc ggg tcc ttc tat tca aaa acc aaa gct atg gtg gag<br>Pro Asn Phe Ile Gly Ser Phe Tyr Ser Lys Thr Lys Ala Met Val Glu<br>           515                    520                    525 | | 1584 |
| gag ctt ttg aaa gaa tat gac aat gtg tgc act ctt aga gtc cga atg<br>Glu Leu Leu Lys Glu Tyr Asp Asn Val Cys Thr Leu Arg Val Arg Met<br>530                        535                    540 | | 1632 |
| cca ata tca tca gat ctc aac aac ccg cgc aat ttc atc acg aaa atc<br>Pro Ile Ser Ser Asp Leu Asn Asn Pro Arg Asn Phe Ile Thr Lys Ile<br>545                        550                    555                  560 | | 1680 |
| gcg cgt tat gat aaa gtt gta aac ata ccc aac agc atg tca atc ttg<br>Ala Arg Tyr Asp Lys Val Val Asn Ile Pro Asn Ser Met Ser Ile Leu<br>                    565                    570                    575 | | 1728 |
| gat gag ctt tta cca atc tca atc gag atg gca aaa cgg aat ctc aag<br>Asp Glu Leu Leu Pro Ile Ser Ile Glu Met Ala Lys Arg Asn Leu Lys<br>            580                    585                    590 | | 1776 |
| gga atc tgg aac ttt aca aac ccg ggg gtt gta agc cac aac gag att<br>Gly Ile Trp Asn Phe Thr Asn Pro Gly Val Val Ser His Asn Glu Ile<br>                    595                    600                    605 | | 1824 |
| ctt gaa atg tac aag aaa tac ata aat ccc gaa ttc aag tgg gtc aat<br>Leu Glu Met Tyr Lys Lys Tyr Ile Asn Pro Glu Phe Lys Trp Val Asn<br>610                        615                    620 | | 1872 |
| ttc aca ctt gat gaa caa gca aaa gtg ata gtg gcc cca cga agc aac<br>Phe Thr Leu Asp Glu Gln Ala Lys Val Ile Val Ala Pro Arg Ser Asn<br>625                        630                    635                  640 | | 1920 |
| aac gag ttg gat gca tca aag ttg aag aaa gag ttt cca gaa ctg cta<br>Asn Glu Leu Asp Ala Ser Lys Leu Lys Lys Glu Phe Pro Glu Leu Leu<br>                    645                    650                    655 | | 1968 |

```
tca atc aag gag tcg ttg atc aag tac gta ttc gaa cct aac aaa aaa      2016
Ser Ile Lys Glu Ser Leu Ile Lys Tyr Val Phe Glu Pro Asn Lys Lys
            660                 665                 670 cat taa                                                               2022
His

<210> SEQ ID NO 2
<211> LENGTH: 673
<212> TYPE: PRT
<213> ORGANISM: Stevia rebaudiana

<400> SEQUENCE: 2

Met Ala Thr Tyr Val Pro Lys Asn Ile Leu Ile Thr Gly Ala Ala Gly
1               5                   10                  15

Phe Ile Ala Ser His Val Ala Asn Arg Leu Val Arg Ser Tyr Pro Asp
            20                  25                  30

Tyr Lys Ile Val Val Leu Asp Lys Leu Asp Tyr Cys Ser Asn Leu Lys
        35                  40                  45

Asn Leu Asn Pro Ser Lys Ser Ser Pro Asn Phe Lys Phe Val Lys Gly
    50                  55                  60

Asp Ile Gly Ser Ala Asp Leu Val Asn Tyr Leu Leu Ile Thr Glu Ser
65                  70                  75                  80

Ile Asp Thr Ile Met His Phe Ala Ala Gln Thr His Val Asp Asn Ser
                85                  90                  95

Phe Gly Asn Ser Phe Glu Phe Thr Lys Asn Asn Ile Tyr Gly Thr His
            100                 105                 110

Val Leu Leu Glu Ala Cys Lys Val Thr Gly Gln Ile Arg Arg Phe Ile
        115                 120                 125

His Val Ser Thr Asp Glu Val Tyr Gly Glu Thr Glu Glu Asp Ala Val
    130                 135                 140

Val Gly Asn His Glu Ala Ser Gln Leu Leu Pro Thr Asn Pro Tyr Ser
145                 150                 155                 160

Ala Thr Lys Ala Gly Ala Glu Met Leu Val Met Ala Tyr Gly Arg Ser
                165                 170                 175

Tyr Gly Leu Pro Val Ile Thr Thr Arg Gly Asn Asn Val Tyr Gly Pro
            180                 185                 190

Asn Gln Phe Pro Glu Lys Leu Ile Pro Lys Phe Ile Leu Leu Ala Met
        195                 200                 205

Arg Gly Gln Pro Leu Pro Ile His Gly Asp Gly Ser Asn Val Arg Ser
    210                 215                 220

Tyr Leu Tyr Cys Glu Asp Val Ala Glu Ala Phe Glu Val Ile Leu His
225                 230                 235                 240

Lys Gly Glu Val Gly His Val Tyr Asn Ile Gly Thr Lys Lys Glu Arg
                245                 250                 255

Arg Val Ile Asp Val Ala Lys Asp Met Cys Lys Leu Phe Asn Met Asp
            260                 265                 270

Pro Asp Ser Ser Ile Lys Phe Val Glu Asn Arg Pro Phe Asn Asp Gln
        275                 280                 285

Arg Tyr Phe Leu Asp Asp Glu Lys Leu Lys Ser Leu Gly Trp Ser Glu
    290                 295                 300

Arg Thr Ile Trp Glu Glu Gly Leu Lys Lys Thr Ile Glu Trp Tyr Thr
305                 310                 315                 320
```

Ser Asn Pro Asn Trp Trp Gly Asp Val Ser Gly Ala Leu Leu Pro His
            325                 330                 335

Pro Arg Met Leu Met Met Pro Gly Gly Val Asp Arg Leu Val Asp Gly
        340                 345                 350

Pro Glu Asn Ala Asp Phe Asp Ser Ala Asp Val Ala Ile Asn Thr Pro
            355                 360                 365

Gln Ile Gly Val Gln Ile Pro Asn Ser Lys Pro Ser Gly Val Ser Phe
370                 375                 380

Lys Lys Pro Gly Leu Lys Phe Leu Ile Tyr Gly Lys Thr Gly Trp Ile
385                 390                 395                 400

Gly Gly Leu Leu Gly Lys Leu Cys Asp Lys Gln Gln Ile Gln Tyr Glu
            405                 410                 415

Tyr Gly Arg Gly Arg Leu Glu Asp Arg Ser Gln Leu Leu Ala Asp Ile
            420                 425                 430

Gln Thr Ile Lys Pro Thr His Val Phe Asn Ala Ala Gly Val Thr Gly
            435                 440                 445

Arg Pro Asn Val Asp Trp Cys Glu Ser His Lys Thr Glu Thr Ile Arg
450                 455                 460

Thr Asn Val Ser Gly Thr Leu Asn Leu Ala Asp Val Cys Arg Glu Asn
465                 470                 475                 480

Gly Leu Leu Met Ile Asn Phe Ala Thr Gly Cys Ile Phe Glu Tyr Asp
            485                 490                 495

Ala Lys His Pro Glu Gly Ser Gly Ile Gly Phe Lys Glu Glu Asp Thr
            500                 505                 510

Pro Asn Phe Ile Gly Ser Phe Tyr Ser Lys Thr Lys Ala Met Val Glu
            515                 520                 525

Glu Leu Leu Lys Glu Tyr Asp Asn Val Cys Thr Leu Arg Val Arg Met
530                 535                 540

Pro Ile Ser Ser Asp Leu Asn Asn Pro Arg Asn Phe Ile Thr Lys Ile
545                 550                 555                 560

Ala Arg Tyr Asp Lys Val Val Asn Ile Pro Asn Ser Met Ser Ile Leu
            565                 570                 575

Asp Glu Leu Leu Pro Ile Ser Ile Glu Met Ala Lys Arg Asn Leu Lys
            580                 585                 590

Gly Ile Trp Asn Phe Thr Asn Pro Gly Val Val Ser His Asn Glu Ile
            595                 600                 605

Leu Glu Met Tyr Lys Lys Tyr Ile Asn Pro Glu Phe Lys Trp Val Asn
610                 615                 620

Phe Thr Leu Asp Glu Gln Ala Lys Val Ile Val Ala Pro Arg Ser Asn
625                 630                 635                 640

Asn Glu Leu Asp Ala Ser Lys Leu Lys Lys Glu Phe Pro Glu Leu Leu
            645                 650                 655

Ser Ile Lys Glu Ser Leu Ile Lys Tyr Val Phe Glu Pro Asn Lys Lys
            660                 665                 670

His

<210> SEQ ID NO 3
<211> LENGTH: 2022
<212> TYPE: DNA
<213> ORGANISM: Stevia rebaudiana
<220> FEATURE:
<221> NAME/KEY: CDS
<222> LOCATION: (1)..(2022)

<400> SEQUENCE: 3

```
atg gct act tac gtg cca aag aac atc ctt atc act gga gct gca ggc      48
Met Ala Thr Tyr Val Pro Lys Asn Ile Leu Ile Thr Gly Ala Ala Gly
1               5                   10                  15 ttc atc gcc tct cat gtt gct aac cgc tta gtc aga agc tac cct gat      96
Phe Ile Ala Ser His Val Ala Asn Arg Leu Val Arg Ser Tyr Pro Asp
            20                  25                  30 tac aag att gtt gtg ctt gac aag ctt gat tat tgt tcc aat ctt aaa     144
Tyr Lys Ile Val Val Leu Asp Lys Leu Asp Tyr Cys Ser Asn Leu Lys
        35                  40                  45 aac ctt aac ccc tcc aaa tca tct ccc aac ttc aag ttt gtt aaa ggc     192
Asn Leu Asn Pro Ser Lys Ser Ser Pro Asn Phe Lys Phe Val Lys Gly
    50                  55                  60 gac atc ggg agc gct gat ctc gtc aac tac cta ctg atc act gaa tcc     240
Asp Ile Gly Ser Ala Asp Leu Val Asn Tyr Leu Leu Ile Thr Glu Ser
65                  70                  75                  80 att gac acc ata atg cac ttt gct gca cag acc cat gtt gat aac tca     288
Ile Asp Thr Ile Met His Phe Ala Ala Gln Thr His Val Asp Asn Ser
                85                  90                  95 ttc ggc aac agt ttc gag ttc aca aag aat aac atc tat gga acc cat     336
Phe Gly Asn Ser Phe Glu Phe Thr Lys Asn Asn Ile Tyr Gly Thr His
            100                 105                 110 gtg ctt cta gaa gcc tgc aaa gtc act ggt cag att aga agg ttc atc     384
Val Leu Leu Glu Ala Cys Lys Val Thr Gly Gln Ile Arg Arg Phe Ile
        115                 120                 125 cat gtg agc aca gat gag gtt tat ggc gaa aca gag gaa gat gct gtt     432
His Val Ser Thr Asp Glu Val Tyr Gly Glu Thr Glu Glu Asp Ala Val
    130                 135                 140 gtt ggt aac cat gaa gct tca caa ctt ctt cct acc aac ccg tat tcc     480
Val Gly Asn His Glu Ala Ser Gln Leu Leu Pro Thr Asn Pro Tyr Ser
145                 150                 155                 160 gcc aca aaa gct ggt gca gaa atg ctt gtt atg gct tac ggt agg tcc     528
Ala Thr Lys Ala Gly Ala Glu Met Leu Val Met Ala Tyr Gly Arg Ser
                165                 170                 175 tac ggg tta ccc gtg att acc act aga ggt aac aat gtt tat ggc ccg     576
Tyr Gly Leu Pro Val Ile Thr Thr Arg Gly Asn Asn Val Tyr Gly Pro
            180                 185                 190 aat caa ttt cca gag aaa cta atc cct aaa ttc atc ctt ctg gcg atg     624
Asn Gln Phe Pro Glu Lys Leu Ile Pro Lys Phe Ile Leu Leu Ala Met
        195                 200                 205 aga ggt caa ccg cta cca att cat ggt gat ggt tct aat gtc aga agt     672
Arg Gly Gln Pro Leu Pro Ile His Gly Asp Gly Ser Asn Val Arg Ser
    210                 215                 220 tat ctg tac tgt gaa gat gtt gca gaa gcg ttt gaa gta att ctt cac     720
Tyr Leu Tyr Cys Glu Asp Val Ala Glu Ala Phe Glu Val Ile Leu His
225                 230                 235                 240 aaa gga gaa gtt ggt cat gtt tac aac ata ggg acg aaa aaa gaa agg     768
Lys Gly Glu Val Gly His Val Tyr Asn Ile Gly Thr Lys Lys Glu Arg
                245                 250                 255 cga gtg att gat gtt gca aaa gat atg tgc aag ctt ttc aat atg gat     816
Arg Val Ile Asp Val Ala Lys Asp Met Cys Lys Leu Phe Asn Met Asp
            260                 265                 270 cct gat tca agc atc aag ttt gtt gaa aac aga ccg ttt aac gat cag     864
Pro Asp Ser Ser Ile Lys Phe Val Glu Asn Arg Pro Phe Asn Asp Gln
        275                 280                 285 agg tat ttc tta gat gat gag aaa ttg aaa agt ttg ggt tgg tcc gaa     912
Arg Tyr Phe Leu Asp Asp Glu Lys Leu Lys Ser Leu Gly Trp Ser Glu
    290                 295                 300
```

-continued

| | | |
|---|---|---|
| agg aca att tgg gaa gag ggt ttg aaa aag acc atc gag tgg tat acc<br>Arg Thr Ile Trp Glu Glu Gly Leu Lys Lys Thr Ile Glu Trp Tyr Thr<br>305                           310                     315                 320 | 960 |
| agc aac cct aat tgg tgg gga gat gtg tcg gga gca ctt ttg cct cat<br>Ser Asn Pro Asn Trp Trp Gly Asp Val Ser Gly Ala Leu Leu Pro His<br>                     325                           330                     335 | 1008 |
| cca aga atg tta atg atg cca ggt ggc gtt gat aga ttg gtt gat gga<br>Pro Arg Met Leu Met Met Pro Gly Gly Val Asp Arg Leu Val Asp Gly<br>               340                          345                   350 | 1056 |
| ccg gaa aac gcg gat ttt gac tct gct gat gtg gcg atc aat act tct<br>Pro Glu Asn Ala Asp Phe Asp Ser Ala Asp Val Ala Ile Asn Thr Ser<br>           355                           360                   365 | 1104 |
| cag att ggc gtc caa ata cct aat tcg aaa ccc agt ggc gta ttg gtt<br>Gln Ile Gly Val Gln Ile Pro Asn Ser Lys Pro Ser Gly Val Leu Val<br>370                           375                     380 | 1152 |
| aag aaa cca ggt ttg aag ttt ctc att tat ggg aaa acc ggg tgg atc<br>Lys Lys Pro Gly Leu Lys Phe Leu Ile Tyr Gly Lys Thr Gly Trp Ile<br>385                           390                     395                   400 | 1200 |
| ggt ggt tta ctc ggg aag tta tgt gat aaa caa cag att caa tac gag<br>Gly Gly Leu Leu Gly Lys Leu Cys Asp Lys Gln Gln Ile Gln Tyr Glu<br>                     405                           410                     415 | 1248 |
| tat gga aga ggt cgg ttg gag gat cgc tca caa ctt ttg gct gat att<br>Tyr Gly Arg Gly Arg Leu Glu Asp Arg Ser Gln Leu Leu Ala Asp Ile<br>               420                          425                   430 | 1296 |
| caa act atc aaa ccg act cat gtt ttc aat gct gct ggt gtc act ggt<br>Gln Thr Ile Lys Pro Thr His Val Phe Asn Ala Ala Gly Val Thr Gly<br>           435                           440                   445 | 1344 |
| aga ccg aat gtt gat tgg tgt gaa tct cac aag acg gaa acc att cgt<br>Arg Pro Asn Val Asp Trp Cys Glu Ser His Lys Thr Glu Thr Ile Arg<br>450                           455                     460 | 1392 |
| acc aat gtt tcg ggt aca ctt aat ctt gca gat gtt tgc aga gaa aac<br>Thr Asn Val Ser Gly Thr Leu Asn Leu Ala Asp Val Cys Arg Glu Asn<br>465                           470                     475                   480 | 1440 |
| gga ctg tta atg atc aac ttt gct acc gga tgc ata ttt gag tat gat<br>Gly Leu Leu Met Ile Asn Phe Ala Thr Gly Cys Ile Phe Glu Tyr Asp<br>                     485                           490                   495 | 1488 |
| gct aaa cat ccg gaa ggt tcc gga atc ggt ttt aag gaa gaa gat aca<br>Ala Lys His Pro Glu Gly Ser Gly Ile Gly Phe Lys Glu Glu Asp Thr<br>           500                           505                   510 | 1536 |
| ccc aat ttc atc ggg tcc ttc tat tca aaa acc aaa gct atg gtg gag<br>Pro Asn Phe Ile Gly Ser Phe Tyr Ser Lys Thr Lys Ala Met Val Glu<br>           515                           520                   525 | 1584 |
| gag ctt ttg aaa gaa tat gac aat gtg tgc act ctt aga gtc cga atg<br>Glu Leu Leu Lys Glu Tyr Asp Asn Val Cys Thr Leu Arg Val Arg Met<br>530                           535                     540 | 1632 |
| cca ata tca tca gat ctc aac aac ccg cgc aat ttc atc acg aaa atc<br>Pro Ile Ser Ser Asp Leu Asn Asn Pro Arg Asn Phe Ile Thr Lys Ile<br>545                           550                     555                   560 | 1680 |
| gcg cgt tat gat aaa gtt gta aac ata ccc aac agc atg tca atc ttg<br>Ala Arg Tyr Asp Lys Val Val Asn Ile Pro Asn Ser Met Ser Ile Leu<br>                     565                           570                   575 | 1728 |
| gat gag ctt tta cca atc tca atc gag atg gca aaa cgg aat ctc aag<br>Asp Glu Leu Leu Pro Ile Ser Ile Glu Met Ala Lys Arg Asn Leu Lys<br>                       580                           585                   590 | 1776 |
| gga atc tgg aac ttt aca aac ccg ggg gtt gta agc cac aac gag att<br>Gly Ile Trp Asn Phe Thr Asn Pro Gly Val Val Ser His Asn Glu Ile<br>           595                           600                   605 | 1824 |
| ctt gaa atg tac aag aaa tac ata aat ccc gaa ttc aag tgg gtc aat<br>Leu Glu Met Tyr Lys Lys Tyr Ile Asn Pro Glu Phe Lys Trp Val Asn<br>610                           615                     620 | 1872 |

```
ttc aca ctt gat gaa caa gca aaa gtg ata gtg gcc cca cga agc aac      1920
Phe Thr Leu Asp Glu Gln Ala Lys Val Ile Val Ala Pro Arg Ser Asn
625                 630                 635                 640 aac gag ttg gat gca tca aag ttg aag aaa gag ttt cca gaa ctg cta      1968
Asn Glu Leu Asp Ala Ser Lys Leu Lys Lys Glu Phe Pro Glu Leu Leu
            645                 650                 655 tca atc aag gag tcg ttg atc aag tac gta ttc gaa cct aac aaa aaa      2016
Ser Ile Lys Glu Ser Leu Ile Lys Tyr Val Phe Glu Pro Asn Lys Lys
660                 665                 670 cat taa                                                              2022
His

<210> SEQ ID NO 4
<211> LENGTH: 673
<212> TYPE: PRT
<213> ORGANISM: Stevia rebaudiana

<400> SEQUENCE: 4

Met Ala Thr Tyr Val Pro Lys Asn Ile Leu Ile Thr Gly Ala Ala Gly
1               5                   10                  15

Phe Ile Ala Ser His Val Ala Asn Arg Leu Val Arg Ser Tyr Pro Asp
                20                  25                  30

Tyr Lys Ile Val Leu Asp Lys Leu Asp Tyr Cys Ser Asn Leu Lys
            35                  40                  45

Asn Leu Asn Pro Ser Lys Ser Pro Asn Phe Lys Phe Val Lys Gly
50                  55                  60

Asp Ile Gly Ser Ala Asp Leu Val Asn Tyr Leu Leu Ile Thr Glu Ser
65                  70                  75                  80

Ile Asp Thr Ile Met His Phe Ala Ala Gln Thr His Val Asp Asn Ser
                85                  90                  95

Phe Gly Asn Ser Phe Glu Phe Thr Lys Asn Asn Ile Tyr Gly Thr His
                100                 105                 110

Val Leu Leu Glu Ala Cys Lys Val Thr Gly Gln Ile Arg Arg Phe Ile
            115                 120                 125

His Val Ser Thr Asp Glu Val Tyr Gly Glu Thr Glu Glu Asp Ala Val
        130                 135                 140

Val Gly Asn His Glu Ala Ser Gln Leu Leu Pro Thr Asn Pro Tyr Ser
145                 150                 155                 160

Ala Thr Lys Ala Gly Ala Glu Met Leu Val Met Ala Tyr Gly Arg Ser
                165                 170                 175

Tyr Gly Leu Pro Val Ile Thr Thr Arg Gly Asn Asn Val Tyr Gly Pro
            180                 185                 190

Asn Gln Phe Pro Glu Lys Leu Ile Pro Lys Phe Ile Leu Leu Ala Met
        195                 200                 205

Arg Gly Gln Pro Leu Pro Ile His Gly Asp Gly Ser Asn Val Arg Ser
210                 215                 220

Tyr Leu Tyr Cys Glu Asp Val Ala Glu Ala Phe Glu Val Ile Leu His
225                 230                 235                 240

Lys Gly Glu Val Gly His Val Tyr Asn Ile Gly Thr Lys Lys Glu Arg
                245                 250                 255

Arg Val Ile Asp Val Ala Lys Asp Met Cys Lys Leu Phe Asn Met Asp
            260                 265                 270

Pro Asp Ser Ser Ile Lys Phe Val Glu Asn Arg Pro Phe Asn Asp Gln
        275                 280                 285

Arg Tyr Phe Leu Asp Asp Glu Lys Leu Lys Ser Leu Gly Trp Ser Glu
290                 295                 300
```

```
Arg Thr Ile Trp Glu Glu Gly Leu Lys Lys Thr Ile Glu Trp Tyr Thr
305                 310                 315                 320

Ser Asn Pro Asn Trp Trp Gly Asp Val Ser Gly Ala Leu Leu Pro His
            325                 330                 335

Pro Arg Met Leu Met Met Pro Gly Gly Val Asp Arg Leu Val Asp Gly
            340                 345                 350

Pro Glu Asn Ala Asp Phe Asp Ser Ala Asp Val Ala Ile Asn Thr Ser
            355                 360                 365

Gln Ile Gly Val Gln Ile Pro Asn Ser Lys Pro Ser Gly Val Leu Val
            370                 375                 380

Lys Lys Pro Gly Leu Lys Phe Leu Ile Tyr Gly Lys Thr Gly Trp Ile
385                 390                 395                 400

Gly Gly Leu Leu Gly Lys Leu Cys Asp Lys Gln Ile Gln Tyr Glu
                405                 410                 415

Tyr Gly Arg Gly Arg Leu Glu Asp Arg Ser Gln Leu Leu Ala Asp Ile
            420                 425                 430

Gln Thr Ile Lys Pro Thr His Val Phe Asn Ala Ala Gly Val Thr Gly
            435                 440                 445

Arg Pro Asn Val Asp Trp Cys Glu Ser His Lys Thr Glu Thr Ile Arg
450                 455                 460

Thr Asn Val Ser Gly Thr Leu Asn Leu Ala Asp Val Cys Arg Glu Asn
465                 470                 475                 480

Gly Leu Leu Met Ile Asn Phe Ala Thr Gly Cys Ile Phe Glu Tyr Asp
                485                 490                 495

Ala Lys His Pro Glu Gly Ser Gly Ile Gly Phe Lys Glu Glu Asp Thr
            500                 505                 510

Pro Asn Phe Ile Gly Ser Phe Tyr Ser Lys Thr Lys Ala Met Val Glu
            515                 520                 525

Glu Leu Leu Lys Glu Tyr Asp Asn Val Cys Thr Leu Arg Val Arg Met
            530                 535                 540

Pro Ile Ser Ser Asp Leu Asn Asn Pro Arg Asn Phe Ile Thr Lys Ile
545                 550                 555                 560

Ala Arg Tyr Asp Lys Val Val Asn Ile Pro Asn Ser Met Ser Ile Leu
            565                 570                 575

Asp Glu Leu Leu Pro Ile Ser Ile Glu Met Ala Lys Arg Asn Leu Lys
            580                 585                 590

Gly Ile Trp Asn Phe Thr Asn Pro Gly Val Val Ser His Asn Glu Ile
            595                 600                 605

Leu Glu Met Tyr Lys Lys Tyr Ile Asn Pro Glu Phe Lys Trp Val Asn
            610                 615                 620

Phe Thr Leu Asp Glu Gln Ala Lys Val Ile Val Ala Pro Arg Ser Asn
625                 630                 635                 640

Asn Glu Leu Asp Ala Ser Lys Leu Lys Lys Glu Phe Pro Glu Leu Leu
            645                 650                 655

Ser Ile Lys Glu Ser Leu Ile Lys Tyr Val Phe Glu Pro Asn Lys Lys
            660                 665                 670

His

<210> SEQ ID NO 5
<211> LENGTH: 2022
<212> TYPE: DNA
<213> ORGANISM: Stevia rebaudiana
```

```
<220> FEATURE:
<221> NAME/KEY: CDS
<222> LOCATION: (1)..(2022)

<400> SEQUENCE: 5 atg gct act tac gtg cca aag aac atc ctt atc act gga gct gca ggc      48
Met Ala Thr Tyr Val Pro Lys Asn Ile Leu Ile Thr Gly Ala Ala Gly
1               5                   10                  15 ttc atc gcc tct cat gtt gct aac cgc tta gtc aga agc tac cct gat      96
Phe Ile Ala Ser His Val Ala Asn Arg Leu Val Arg Ser Tyr Pro Asp
                20                  25                  30 tac aag att gtt gtg ctt gac aag ctt gat tat tgt tcc aat ctt aaa     144
Tyr Lys Ile Val Val Leu Asp Lys Leu Asp Tyr Cys Ser Asn Leu Lys
            35                  40                  45 aac ctt aac ccc tcc aaa tca tct ccc aac ttc aag ttt gtt aaa ggc     192
Asn Leu Asn Pro Ser Lys Ser Ser Pro Asn Phe Lys Phe Val Lys Gly
50                  55                  60 gac atc ggg agc gct gat ctc gtc aac tac cta ctg atc act gaa tcc     240
Asp Ile Gly Ser Ala Asp Leu Val Asn Tyr Leu Leu Ile Thr Glu Ser
65                  70                  75                  80 att gac acc ata atg cac ttt gct gca cag acc cat gtt gat aac tca     288
Ile Asp Thr Ile Met His Phe Ala Ala Gln Thr His Val Asp Asn Ser
                85                  90                  95 ttc ggc aac agt ttc gag ttc aca aag aat aac atc tat gga acc cat     336
Phe Gly Asn Ser Phe Glu Phe Thr Lys Asn Asn Ile Tyr Gly Thr His
            100                 105                 110 gtg ctt cta gaa gcc tgc aaa gtc act ggt cag att aga agg ttc atc     384
Val Leu Leu Glu Ala Cys Lys Val Thr Gly Gln Ile Arg Arg Phe Ile
        115                 120                 125 cat gtg agc aca gat gag gtt tat ggc gaa aca gag gaa gat gct gtt     432
His Val Ser Thr Asp Glu Val Tyr Gly Glu Thr Glu Glu Asp Ala Val
130                 135                 140 gtt ggt aac cat gaa gct tca caa ctt ctt cct acc aac ccg tat tcc     480
Val Gly Asn His Glu Ala Ser Gln Leu Leu Pro Thr Asn Pro Tyr Ser
145                 150                 155                 160 gcc aca aaa gct ggt gca gaa atg ctt gtt atg gct tac ggt agg tcc     528
Ala Thr Lys Ala Gly Ala Glu Met Leu Val Met Ala Tyr Gly Arg Ser
                165                 170                 175 tac ggg tta ccc gtg att acc act aga ggt aac aat gtt tat ggc ccg     576
Tyr Gly Leu Pro Val Ile Thr Thr Arg Gly Asn Asn Val Tyr Gly Pro
            180                 185                 190 aat caa ttt cca gag aaa cta atc cct aaa ttc atc ctt ctg gcg atg     624
Asn Gln Phe Pro Glu Lys Leu Ile Pro Lys Phe Ile Leu Leu Ala Met
        195                 200                 205 aga ggt caa ccg cta cca att cat ggt gat ggt tct aat gtc aga agt     672
Arg Gly Gln Pro Leu Pro Ile His Gly Asp Gly Ser Asn Val Arg Ser
210                 215                 220 tat ctg tac tgt gaa gat gtt gca gaa gcg ttt gaa gta att ctt cac     720
Tyr Leu Tyr Cys Glu Asp Val Ala Glu Ala Phe Glu Val Ile Leu His
225                 230                 235                 240 aaa gga gaa gtt ggt cat gtt tac aac ata ggg acg aaa aaa gaa agg     768
Lys Gly Glu Val Gly His Val Tyr Asn Ile Gly Thr Lys Lys Glu Arg
                245                 250                 255 cga gtg att gat gtt gca aaa gat atg tgc aag ctt ttc aat atg gat     816
Arg Val Ile Asp Val Ala Lys Asp Met Cys Lys Leu Phe Asn Met Asp
            260                 265                 270 cct gat tca agc atc aag ttt gtt gaa aac aga ccg ttt aac gat cag     864
Pro Asp Ser Ser Ile Lys Phe Val Glu Asn Arg Pro Phe Asn Asp Gln
        275                 280                 285
```

-continued

| | | | | | | | | | | | | | | | | |
|---|---|---|---|---|---|---|---|---|---|---|---|---|---|---|---|---|
| agg | tat | ttc | tta | gat | gat | gag | aaa | ttg | aaa | agt | ttg | ggt | tgg | tcc | gaa | 912 |
| Arg | Tyr | Phe | Leu | Asp | Asp | Glu | Lys | Leu | Lys | Ser | Leu | Gly | Trp | Ser | Glu | |
| 290 | | | | | 295 | | | | | 300 | | | | | | |

| | | | | | | | | | | | | | | | | |
|---|---|---|---|---|---|---|---|---|---|---|---|---|---|---|---|---|
| agg | aca | att | tgg | gaa | gag | ggt | ttg | aaa | aag | acc | atc | gag | tgg | tat | acc | 960 |
| Arg | Thr | Ile | Trp | Glu | Glu | Gly | Leu | Lys | Lys | Thr | Ile | Glu | Trp | Tyr | Thr | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| agc | aac | cct | aat | tgg | tgg | gga | gat | gtg | tcg | gga | gca | ctt | ttg | cct | cat | 1008 |
| Ser | Asn | Pro | Asn | Trp | Trp | Gly | Asp | Val | Ser | Gly | Ala | Leu | Leu | Pro | His | |
| | | | | 325 | | | | | 330 | | | | | 335 | | |

| | | | | | | | | | | | | | | | | |
|---|---|---|---|---|---|---|---|---|---|---|---|---|---|---|---|---|
| cca | aga | atg | tta | atg | atg | cca | ggt | ggc | gtt | gat | aga | ttg | gtt | gat | gga | 1056 |
| Pro | Arg | Met | Leu | Met | Met | Pro | Gly | Gly | Val | Asp | Arg | Leu | Val | Asp | Gly | |
| | | | 340 | | | | | 345 | | | | | 350 | | | |

| | | | | | | | | | | | | | | | | |
|---|---|---|---|---|---|---|---|---|---|---|---|---|---|---|---|---|
| ccg | gaa | aac | gcg | gat | ttt | gac | tct | gct | gat | gtg | gcg | atc | aat | act | tct | 1104 |
| Pro | Glu | Asn | Ala | Asp | Phe | Asp | Ser | Ala | Asp | Val | Ala | Ile | Asn | Thr | Ser | |
| | | 355 | | | | | 360 | | | | | 365 | | | | |

| | | | | | | | | | | | | | | | | |
|---|---|---|---|---|---|---|---|---|---|---|---|---|---|---|---|---|
| cag | att | ggt | gtc | caa | ata | cct | aac | tcg | aaa | ccc | agt | ggc | gta | tcg | gtt | 1152 |
| Gln | Ile | Gly | Val | Gln | Ile | Pro | Asn | Ser | Lys | Pro | Ser | Gly | Val | Ser | Val | |
| | 370 | | | | | 375 | | | | | 380 | | | | | |

| | | | | | | | | | | | | | | | | |
|---|---|---|---|---|---|---|---|---|---|---|---|---|---|---|---|---|
| aag | aaa | cca | ggt | ttg | aag | ttt | ctc | att | tat | ggg | aaa | acc | ggg | tgg | atc | 1200 |
| Lys | Lys | Pro | Gly | Leu | Lys | Phe | Leu | Ile | Tyr | Gly | Lys | Thr | Gly | Trp | Ile | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| ggt | ggt | tta | ctc | ggg | aag | tta | tgt | gat | aaa | caa | cag | att | caa | tac | gag | 1248 |
| Gly | Gly | Leu | Leu | Gly | Lys | Leu | Cys | Asp | Lys | Gln | Gln | Ile | Gln | Tyr | Glu | |
| | | | | 405 | | | | | 410 | | | | | 415 | | |

| | | | | | | | | | | | | | | | | |
|---|---|---|---|---|---|---|---|---|---|---|---|---|---|---|---|---|
| tat | gga | aga | ggt | cgg | ttg | gag | gat | cgc | tca | caa | ctt | ttg | gct | gat | att | 1296 |
| Tyr | Gly | Arg | Gly | Arg | Leu | Glu | Asp | Arg | Ser | Gln | Leu | Leu | Ala | Asp | Ile | |
| | | | 420 | | | | | 425 | | | | | 430 | | | |

| | | | | | | | | | | | | | | | | |
|---|---|---|---|---|---|---|---|---|---|---|---|---|---|---|---|---|
| caa | act | atc | aaa | ccg | act | cat | gtt | ttc | aat | gct | gct | ggt | gtc | act | ggt | 1344 |
| Gln | Thr | Ile | Lys | Pro | Thr | His | Val | Phe | Asn | Ala | Ala | Gly | Val | Thr | Gly | |
| | | 435 | | | | | 440 | | | | | 445 | | | | |

| | | | | | | | | | | | | | | | | |
|---|---|---|---|---|---|---|---|---|---|---|---|---|---|---|---|---|
| aga | ccg | aat | gtt | gat | tgg | tgt | gaa | tct | cac | aag | acg | gaa | acc | att | cgt | 1392 |
| Arg | Pro | Asn | Val | Asp | Trp | Cys | Glu | Ser | His | Lys | Thr | Glu | Thr | Ile | Arg | |
| | 450 | | | | | 455 | | | | | 460 | | | | | |

| | | | | | | | | | | | | | | | | |
|---|---|---|---|---|---|---|---|---|---|---|---|---|---|---|---|---|
| acc | aat | gtt | tcg | ggt | aca | ctt | aat | ctt | gca | gat | gtt | tgc | aga | gaa | aac | 1440 |
| Thr | Asn | Val | Ser | Gly | Thr | Leu | Asn | Leu | Ala | Asp | Val | Cys | Arg | Glu | Asn | |
| 465 | | | | | 470 | | | | | 475 | | | | | 480 | |

| | | | | | | | | | | | | | | | | |
|---|---|---|---|---|---|---|---|---|---|---|---|---|---|---|---|---|
| gga | ctg | tta | atg | atc | aac | ttt | gct | acc | gga | tgc | ata | ttt | gag | tat | gat | 1488 |
| Gly | Leu | Leu | Met | Ile | Asn | Phe | Ala | Thr | Gly | Cys | Ile | Phe | Glu | Tyr | Asp | |
| | | | | 485 | | | | | 490 | | | | | 495 | | |

| | | | | | | | | | | | | | | | | |
|---|---|---|---|---|---|---|---|---|---|---|---|---|---|---|---|---|
| gct | aaa | cat | ccg | gaa | ggt | tcc | gga | atc | ggt | ttt | aag | gaa | gaa | gat | aca | 1536 |
| Ala | Lys | His | Pro | Glu | Gly | Ser | Gly | Ile | Gly | Phe | Lys | Glu | Glu | Asp | Thr | |
| | | | 500 | | | | | 505 | | | | | 510 | | | |

| | | | | | | | | | | | | | | | | |
|---|---|---|---|---|---|---|---|---|---|---|---|---|---|---|---|---|
| ccc | aat | ttc | atc | ggg | tcc | ttc | tat | tca | aaa | acc | aaa | gct | atg | gtg | gag | 1584 |
| Pro | Asn | Phe | Ile | Gly | Ser | Phe | Tyr | Ser | Lys | Thr | Lys | Ala | Met | Val | Glu | |
| | | 515 | | | | | 520 | | | | | 525 | | | | |

| | | | | | | | | | | | | | | | | |
|---|---|---|---|---|---|---|---|---|---|---|---|---|---|---|---|---|
| gag | ctt | ttg | aaa | gaa | tat | gac | aat | gtg | tgc | act | ctt | aga | gtc | cga | atg | 1632 |
| Glu | Leu | Leu | Lys | Glu | Tyr | Asp | Asn | Val | Cys | Thr | Leu | Arg | Val | Arg | Met | |
| | 530 | | | | | 535 | | | | | 540 | | | | | |

| | | | | | | | | | | | | | | | | |
|---|---|---|---|---|---|---|---|---|---|---|---|---|---|---|---|---|
| cca | ata | tca | tca | gat | ctc | aac | aac | ccg | cgc | aat | ttc | atc | acg | aaa | atc | 1680 |
| Pro | Ile | Ser | Ser | Asp | Leu | Asn | Asn | Pro | Arg | Asn | Phe | Ile | Thr | Lys | Ile | |
| 545 | | | | | 550 | | | | | 555 | | | | | 560 | |

| | | | | | | | | | | | | | | | | |
|---|---|---|---|---|---|---|---|---|---|---|---|---|---|---|---|---|
| gcg | cgt | tat | gat | aaa | gtt | gta | aac | ata | ccc | aac | agc | atg | tca | atc | ttg | 1728 |
| Ala | Arg | Tyr | Asp | Lys | Val | Val | Asn | Ile | Pro | Asn | Ser | Met | Ser | Ile | Leu | |
| | | | | 565 | | | | | 570 | | | | | 575 | | |

| | | | | | | | | | | | | | | | | |
|---|---|---|---|---|---|---|---|---|---|---|---|---|---|---|---|---|
| gat | gag | ctt | tta | cca | atc | tca | atc | gag | atg | gca | aaa | cgg | aat | ctc | aag | 1776 |
| Asp | Glu | Leu | Leu | Pro | Ile | Ser | Ile | Glu | Met | Ala | Lys | Arg | Asn | Leu | Lys | |
| | | | 580 | | | | | 585 | | | | | 590 | | | |

| | | | | | | | | | | | | | | | | |
|---|---|---|---|---|---|---|---|---|---|---|---|---|---|---|---|---|
| gga | atc | tgg | aac | ttt | aca | aac | ccg | ggg | att | gta | agc | cac | aac | gag | att | 1824 |
| Gly | Ile | Trp | Asn | Phe | Thr | Asn | Pro | Gly | Ile | Val | Ser | His | Asn | Glu | Ile | |
| | | 595 | | | | | 600 | | | | | 605 | | | | |

| | | | | | | | | | | | | | | | | |
|---|---|---|---|---|---|---|---|---|---|---|---|---|---|---|---|---|
| ctt | gaa | atg | tac | aag | aaa | tac | ata | aat | ccc | gaa | ttc | aag | tgg | gtc | aat | 1872 |
| Leu | Glu | Met | Tyr | Lys | Lys | Tyr | Ile | Asn | Pro | Glu | Phe | Lys | Trp | Val | Asn | |
| | 610 | | | | | 615 | | | | | 620 | | | | | |
| ttc | aca | ctt | gat | gaa | caa | gca | aaa | gtg | ata | gtg | gcc | cca | cga | agc | aac | 1920 |
| Phe | Thr | Leu | Asp | Glu | Gln | Ala | Lys | Val | Ile | Val | Ala | Pro | Arg | Ser | Asn | |
| 625 | | | | | 630 | | | | | 635 | | | | | 640 | |
| aac | gag | ttg | gat | gca | tca | aag | ttg | aag | aaa | gag | ttt | cca | gaa | ctg | cta | 1968 |
| Asn | Glu | Leu | Asp | Ala | Ser | Lys | Leu | Lys | Lys | Glu | Phe | Pro | Glu | Leu | Leu | |
| | | | | 645 | | | | | 650 | | | | | 655 | | |
| tca | atc | aag | gag | tcg | ttg | atc | aag | tac | gta | ttc | gaa | cct | aac | aaa | aaa | 2016 |
| Ser | Ile | Lys | Glu | Ser | Leu | Ile | Lys | Tyr | Val | Phe | Glu | Pro | Asn | Lys | Lys | |
| | | | 660 | | | | | 665 | | | | | 670 | | | |
| cat | taa | | | | | | | | | | | | | | | 2022 |
| His | | | | | | | | | | | | | | | | |

<210> SEQ ID NO 6
<211> LENGTH: 673
<212> TYPE: PRT
<213> ORGANISM: Stevia rebaudiana

<400> SEQUENCE: 6

Met Ala Thr Tyr Val Pro Lys Asn Ile Leu Ile Thr Gly Ala Ala Gly
1               5                   10                  15

Phe Ile Ala Ser His Val Ala Asn Arg Leu Val Arg Ser Tyr Pro Asp
            20                  25                  30

Tyr Lys Ile Val Val Leu Asp Lys Leu Asp Tyr Cys Ser Asn Leu Lys
        35                  40                  45

Asn Leu Asn Pro Ser Lys Ser Ser Pro Asn Phe Lys Phe Val Lys Gly
    50                  55                  60

Asp Ile Gly Ser Ala Asp Leu Val Asn Tyr Leu Leu Ile Thr Glu Ser
65                  70                  75                  80

Ile Asp Thr Ile Met His Phe Ala Ala Gln Thr His Val Asp Asn Ser
                85                  90                  95

Phe Gly Asn Ser Phe Glu Phe Thr Lys Asn Asn Ile Tyr Gly Thr His
            100                 105                 110

Val Leu Leu Glu Ala Cys Lys Val Thr Gly Gln Ile Arg Arg Phe Ile
        115                 120                 125

His Val Ser Thr Asp Glu Val Tyr Gly Glu Thr Glu Glu Asp Ala Val
    130                 135                 140

Val Gly Asn His Glu Ala Ser Gln Leu Leu Pro Thr Asn Pro Tyr Ser
145                 150                 155                 160

Ala Thr Lys Ala Gly Ala Glu Met Leu Val Met Ala Tyr Gly Arg Ser
                165                 170                 175

Tyr Gly Leu Pro Val Ile Thr Thr Arg Gly Asn Asn Val Tyr Gly Pro
            180                 185                 190

Asn Gln Phe Pro Glu Lys Leu Ile Pro Lys Phe Ile Leu Leu Ala Met
        195                 200                 205

Arg Gly Gln Pro Leu Pro Ile His Gly Asp Gly Ser Asn Val Arg Ser
    210                 215                 220

Tyr Leu Tyr Cys Glu Asp Val Ala Glu Ala Phe Glu Val Ile Leu His
225                 230                 235                 240

Lys Gly Glu Val Gly His Val Tyr Asn Ile Gly Thr Lys Lys Glu Arg
                245                 250                 255

Arg Val Ile Asp Val Ala Lys Asp Met Cys Lys Leu Phe Asn Met Asp
            260                 265                 270

```
Pro Asp Ser Ile Lys Phe Val Glu Asn Arg Pro Phe Asn Asp Gln
        275                 280                 285

Arg Tyr Phe Leu Asp Asp Glu Lys Leu Lys Ser Leu Gly Trp Ser Glu
    290                 295                 300

Arg Thr Ile Trp Glu Glu Gly Leu Lys Lys Thr Ile Glu Trp Tyr Thr
305                 310                 315                 320

Ser Asn Pro Asn Trp Trp Gly Asp Val Ser Gly Ala Leu Leu Pro His
                325                 330                 335

Pro Arg Met Leu Met Met Pro Gly Gly Val Asp Arg Leu Val Asp Gly
            340                 345                 350

Pro Glu Asn Ala Asp Phe Asp Ser Ala Asp Val Ala Ile Asn Thr Ser
            355                 360                 365

Gln Ile Gly Val Gln Ile Pro Asn Ser Lys Pro Ser Gly Val Ser Val
        370                 375                 380

Lys Lys Pro Gly Leu Lys Phe Leu Ile Tyr Gly Lys Thr Gly Trp Ile
385                 390                 395                 400

Gly Gly Leu Leu Gly Lys Leu Cys Asp Lys Gln Gln Ile Gln Tyr Glu
                405                 410                 415

Tyr Gly Arg Gly Arg Leu Glu Asp Arg Ser Gln Leu Leu Ala Asp Ile
            420                 425                 430

Gln Thr Ile Lys Pro Thr His Val Phe Asn Ala Ala Gly Val Thr Gly
        435                 440                 445

Arg Pro Asn Val Asp Trp Cys Glu Ser His Lys Thr Glu Thr Ile Arg
    450                 455                 460

Thr Asn Val Ser Gly Thr Leu Asn Leu Ala Asp Val Cys Arg Glu Asn
465                 470                 475                 480

Gly Leu Leu Met Ile Asn Phe Ala Thr Gly Cys Ile Phe Glu Tyr Asp
                485                 490                 495

Ala Lys His Pro Glu Gly Ser Gly Ile Gly Phe Lys Glu Glu Asp Thr
            500                 505                 510

Pro Asn Phe Ile Gly Ser Phe Tyr Ser Lys Thr Lys Ala Met Val Glu
        515                 520                 525

Glu Leu Leu Lys Glu Tyr Asp Asn Val Cys Thr Leu Arg Val Arg Met
530                 535                 540

Pro Ile Ser Ser Asp Leu Asn Asn Pro Arg Asn Phe Ile Thr Lys Ile
545                 550                 555                 560

Ala Arg Tyr Asp Lys Val Asn Ile Pro Asn Ser Met Ser Ile Leu
                565                 570                 575

Asp Glu Leu Leu Pro Ile Ser Ile Glu Met Ala Lys Arg Asn Leu Lys
            580                 585                 590

Gly Ile Trp Asn Phe Thr Asn Pro Gly Ile Val Ser His Asn Glu Ile
        595                 600                 605

Leu Glu Met Tyr Lys Lys Tyr Ile Asn Pro Glu Phe Lys Trp Val Asn
    610                 615                 620

Phe Thr Leu Asp Glu Gln Ala Lys Val Ile Val Ala Pro Arg Ser Asn
625                 630                 635                 640

Asn Glu Leu Asp Ala Ser Lys Leu Lys Lys Glu Phe Pro Glu Leu Leu
                645                 650                 655

Ser Ile Lys Glu Ser Leu Ile Lys Tyr Val Phe Glu Pro Asn Lys Lys
            660                 665                 670

His
```

```
<210> SEQ ID NO 7
<211> LENGTH: 1992
<212> TYPE: DNA
<213> ORGANISM: Stevia rebaudiana
<220> FEATURE:
<221> NAME/KEY: CDS
<222> LOCATION: (1)..(1992)

<400> SEQUENCE: 7
```

| | | | | | | | | | | | | | | | | |
|---|---|---|---|---|---|---|---|---|---|---|---|---|---|---|---|---|
| atg | acc | agt | tat | aca | cct | aaa | aac | atc | ctc | atc | act | ggg | gca | gct | gga | 48 |
| Met | Thr | Ser | Tyr | Thr | Pro | Lys | Asn | Ile | Leu | Ile | Thr | Gly | Ala | Ala | Gly | |
| 1 | | | | 5 | | | | | 10 | | | | | 15 | | |
| ttc | atc | gcc | tct | cat | gta | gct | aat | cgt | ctt | gtt | aga | acc | tat | ccg | gat | 96 |
| Phe | Ile | Ala | Ser | His | Val | Ala | Asn | Arg | Leu | Val | Arg | Thr | Tyr | Pro | Asp | |
| | | | 20 | | | | | 25 | | | | | 30 | | | |
| tac | aaa | att | gtt | gtg | ctt | gac | aag | ctt | gat | tac | tgc | tca | aat | ctc | aaa | 144 |
| Tyr | Lys | Ile | Val | Val | Leu | Asp | Lys | Leu | Asp | Tyr | Cys | Ser | Asn | Leu | Lys | |
| | 35 | | | | | 40 | | | | | 45 | | | | | |
| aac | cta | aac | ccc | tct | aaa | tca | tct | ccc | aat | ttc | aaa | ttc | gtt | aaa | gga | 192 |
| Asn | Leu | Asn | Pro | Ser | Lys | Ser | Ser | Pro | Asn | Phe | Lys | Phe | Val | Lys | Gly | |
| 50 | | | | | 55 | | | | | 60 | | | | | | |
| gac | atc | gca | agt | gcg | gat | cta | gtc | aat | cat | ttg | tta | ctc | acc | gaa | tcc | 240 |
| Asp | Ile | Ala | Ser | Ala | Asp | Leu | Val | Asn | His | Leu | Leu | Leu | Thr | Glu | Ser | |
| 65 | | | | | 70 | | | | | 75 | | | | | 80 | |
| atc | gac | acc | ata | atg | cac | ttt | gca | gct | caa | act | cat | gtc | gac | aac | tca | 288 |
| Ile | Asp | Thr | Ile | Met | His | Phe | Ala | Ala | Gln | Thr | His | Val | Asp | Asn | Ser | |
| | | | | 85 | | | | | 90 | | | | | 95 | | |
| ttt | ggt | aac | agc | ttc | gag | ttc | aca | aag | aac | aac | ata | tac | ggc | aca | cat | 336 |
| Phe | Gly | Asn | Ser | Phe | Glu | Phe | Thr | Lys | Asn | Asn | Ile | Tyr | Gly | Thr | His | |
| | | | 100 | | | | | 105 | | | | | 110 | | | |
| gtt | ctt | cta | gaa | gcc | tgc | aaa | gtc | acc | cgc | cag | atc | aaa | cgg | ttc | atc | 384 |
| Val | Leu | Leu | Glu | Ala | Cys | Lys | Val | Thr | Arg | Gln | Ile | Lys | Arg | Phe | Ile | |
| | | 115 | | | | | 120 | | | | | 125 | | | | |
| cac | gtc | agc | acc | gat | gag | gtg | tat | ggt | gaa | aca | gat | gaa | gat | gct | gtt | 432 |
| His | Val | Ser | Thr | Asp | Glu | Val | Tyr | Gly | Glu | Thr | Asp | Glu | Asp | Ala | Val | |
| | 130 | | | | | 135 | | | | | 140 | | | | | |
| gtg | ggt | aac | cat | gaa | gcc | tca | caa | ctt | ctt | cct | aca | aat | ccg | tat | tcc | 480 |
| Val | Gly | Asn | His | Glu | Ala | Ser | Gln | Leu | Leu | Pro | Thr | Asn | Pro | Tyr | Ser | |
| 145 | | | | | 150 | | | | | 155 | | | | | 160 | |
| gcc | aca | aaa | gcc | ggt | gca | gaa | atg | ctc | gtt | atg | gct | tat | ggt | aga | tca | 528 |
| Ala | Thr | Lys | Ala | Gly | Ala | Glu | Met | Leu | Val | Met | Ala | Tyr | Gly | Arg | Ser | |
| | | | | 165 | | | | | 170 | | | | | 175 | | |
| tac | ggg | tta | ccc | gtg | atc | acc | act | aga | gga | aac | aac | gtt | tat | ggc | ccg | 576 |
| Tyr | Gly | Leu | Pro | Val | Ile | Thr | Thr | Arg | Gly | Asn | Asn | Val | Tyr | Gly | Pro | |
| | | | 180 | | | | | 185 | | | | | 190 | | | |
| aat | caa | ttt | cct | gaa | aaa | cta | atc | cct | aaa | ttc | att | ctt | tta | tcc | atg | 624 |
| Asn | Gln | Phe | Pro | Glu | Lys | Leu | Ile | Pro | Lys | Phe | Ile | Leu | Leu | Ser | Met | |
| | | 195 | | | | | 200 | | | | | 205 | | | | |
| aga | ggc | aaa | ccg | tta | acg | att | cat | ggt | gac | gga | tcg | aat | gtc | aga | agt | 672 |
| Arg | Gly | Lys | Pro | Leu | Thr | Ile | His | Gly | Asp | Gly | Ser | Asn | Val | Arg | Ser | |
| | 210 | | | | | 215 | | | | | 220 | | | | | |
| tat | ctt | tac | tgt | gaa | gat | gtt | gca | gaa | gca | ttt | gaa | gtc | gtg | tta | cat | 720 |
| Tyr | Leu | Tyr | Cys | Glu | Asp | Val | Ala | Glu | Ala | Phe | Glu | Val | Val | Leu | His | |
| 225 | | | | | 230 | | | | | 235 | | | | | 240 | |
| aaa | gga | gaa | gtt | gga | cat | gtt | tac | aac | att | gga | acc | aaa | aaa | gaa | aga | 768 |
| Lys | Gly | Glu | Val | Gly | His | Val | Tyr | Asn | Ile | Gly | Thr | Lys | Lys | Glu | Arg | |
| | | | | 245 | | | | | 250 | | | | | 255 | | |
| cga | gtg | att | gat | gtt | gct | aaa | gat | ata | tgc | aat | ctt | ttt | gaa | atc | gat | 816 |
| Arg | Val | Ile | Asp | Val | Ala | Lys | Asp | Ile | Cys | Asn | Leu | Phe | Glu | Ile | Asp | |
| | | | | 260 | | | | | 265 | | | | | 270 | | |

```
cat gaa tca aga atc aaa ttt gtt gaa aac aga cct ttt aac gat caa      864
His Glu Ser Arg Ile Lys Phe Val Glu Asn Arg Pro Phe Asn Asp Gln
        275                 280                 285 aga tac ttt tta gat gat gaa aag ctc aag agt ttg ggc tgg gtt gaa      912
Arg Tyr Phe Leu Asp Asp Glu Lys Leu Lys Ser Leu Gly Trp Val Glu
    290                 295                 300 aga acc acg tgg caa gag ggt ttg aaa aaa act atg aaa tgg tat acc      960
Arg Thr Thr Trp Gln Glu Gly Leu Lys Lys Thr Met Lys Trp Tyr Thr
305                 310                 315                 320 atg aat cct gat tgg tgg ggt gac gtg tca ggt gca ttg ctt cct cat     1008
Met Asn Pro Asp Trp Trp Gly Asp Val Ser Gly Ala Leu Leu Pro His
                325                 330                 335 cca cgt atg ctg atg atg cca ggt ggc att caa tct gac tca cct cat     1056
Pro Arg Met Leu Met Met Pro Gly Gly Ile Gln Ser Asp Ser Pro His
            340                 345                 350 tct gga atc atc tct act ccg atg gaa aaa ccg ggt cat ctt tca gga     1104
Ser Gly Ile Ile Ser Thr Pro Met Glu Lys Pro Gly His Leu Ser Gly
        355                 360                 365 ccc ggt ata aat tct tcc aac aaa ccg ggt ttt aag ttc ttg att tac     1152
Pro Gly Ile Asn Ser Ser Asn Lys Pro Gly Phe Lys Phe Leu Ile Tyr
370                 375                 380 ggt cga acc ggg tgg atc ggt ggt tta ctt ggg aag tta tgt gaa aaa     1200
Gly Arg Thr Gly Trp Ile Gly Gly Leu Leu Gly Lys Leu Cys Glu Lys
385                 390                 395                 400 caa ggg att cag tac gag tac gga aag ggt cgg ttg gag aac cgg gcc     1248
Gln Gly Ile Gln Tyr Glu Tyr Gly Lys Gly Arg Leu Glu Asn Arg Ala
                405                 410                 415 caa att gtt tcg gat att cag aac gtt aaa ccg acc cat gtt ttt aac     1296
Gln Ile Val Ser Asp Ile Gln Asn Val Lys Pro Thr His Val Phe Asn
            420                 425                 430 gcg gct ggt gtt acg ggt cga ccg aat gtg gat tgg tgt gaa tct cat     1344
Ala Ala Gly Val Thr Gly Arg Pro Asn Val Asp Trp Cys Glu Ser His
        435                 440                 445 aag act gaa acg att cgc acc aat gtt tca gga acc cta aat ttg gca     1392
Lys Thr Glu Thr Ile Arg Thr Asn Val Ser Gly Thr Leu Asn Leu Ala
    450                 455                 460 gat gtt tgc agg gaa aat ggg atc ttg atg atg aac ttt gct act gga     1440
Asp Val Cys Arg Glu Asn Gly Ile Leu Met Met Asn Phe Ala Thr Gly
465                 470                 475                 480 tgc ata ttt gaa tac gat gat gca cat cct gaa ggt tct gga atc ggg     1488
Cys Ile Phe Glu Tyr Asp Asp Ala His Pro Glu Gly Ser Gly Ile Gly
                485                 490                 495 ttt aaa gaa gaa gac aca ccc aat ttc acc ggt tca ttc tat tcc aaa     1536
Phe Lys Glu Glu Asp Thr Pro Asn Phe Thr Gly Ser Phe Tyr Ser Lys
            500                 505                 510 acc aaa gct atg gtt gag gag ctt ttg aaa gaa tat gac aac gtg tgc     1584
Thr Lys Ala Met Val Glu Glu Leu Leu Lys Glu Tyr Asp Asn Val Cys
        515                 520                 525 aca ctt cgt gtc cgt atg cca ata tct tca gac ctt aac aat cca cgt     1632
Thr Leu Arg Val Arg Met Pro Ile Ser Ser Asp Leu Asn Asn Pro Arg
    530                 535                 540 aat ttt ata act aaa atc gcg cgt tat gat aag gtt gta aat att cca     1680
Asn Phe Ile Thr Lys Ile Ala Arg Tyr Asp Lys Val Val Asn Ile Pro
545                 550                 555                 560 aac tcg atg acg att tta gat gag ctt tta cct att tca ata gaa atg     1728
Asn Ser Met Thr Ile Leu Asp Glu Leu Leu Pro Ile Ser Ile Glu Met
                565                 570                 575 gca aag aga aat tta aaa gga ata tgg aat ttt aca aac ccg ggg gtt     1776
Ala Lys Arg Asn Leu Lys Gly Ile Trp Asn Phe Thr Asn Pro Gly Val
            580                 585                 590
```

```
gtg agt cat aac gag gtt ttg gaa atg tat aaa gat tat ata aac ccg    1824
Val Ser His Asn Glu Val Leu Glu Met Tyr Lys Asp Tyr Ile Asn Pro
    595                 600                 605 gaa ttt aaa tgg aaa aat ttc aca ctt gaa gaa caa gaa cgt gtg att    1872
Glu Phe Lys Trp Lys Asn Phe Thr Leu Glu Glu Gln Glu Arg Val Ile
610                 615                 620 gtt gca cca aga agt aat aat gag ttg gat aca tcc aag ttg aag aaa    1920
Val Ala Pro Arg Ser Asn Asn Glu Leu Asp Thr Ser Lys Leu Lys Lys
625                 630                 635                 640 gag ttt cct gaa ttg ctg tcg att aaa gaa tca ttg gtt aaa tac gta    1968
Glu Phe Pro Glu Leu Leu Ser Ile Lys Glu Ser Leu Val Lys Tyr Val
                645                 650                 655 ttt gca ccc aac aag aca acc taa                                    1992
Phe Ala Pro Asn Lys Thr Thr
                660
```

<210> SEQ ID NO 8
<211> LENGTH: 663
<212> TYPE: PRT
<213> ORGANISM: Stevia rebaudiana

<400> SEQUENCE: 8

```
Met Thr Ser Tyr Thr Pro Lys Asn Ile Leu Ile Thr Gly Ala Ala Gly
1               5                   10                  15

Phe Ile Ala Ser His Val Ala Asn Arg Leu Val Arg Thr Tyr Pro Asp
                20                  25                  30

Tyr Lys Ile Val Val Leu Asp Lys Leu Asp Tyr Cys Ser Asn Leu Lys
            35                  40                  45

Asn Leu Asn Pro Ser Lys Ser Ser Pro Asn Phe Lys Phe Val Lys Gly
    50                  55                  60

Asp Ile Ala Ser Ala Asp Leu Val Asn His Leu Leu Thr Glu Ser
65                  70                  75                  80

Ile Asp Thr Ile Met His Phe Ala Ala Gln Thr His Val Asp Asn Ser
                85                  90                  95

Phe Gly Asn Ser Phe Glu Phe Thr Lys Asn Asn Ile Tyr Gly Thr His
            100                 105                 110

Val Leu Leu Glu Ala Cys Lys Val Thr Arg Gln Ile Lys Arg Phe Ile
        115                 120                 125

His Val Ser Thr Asp Glu Val Tyr Gly Glu Thr Asp Glu Asp Ala Val
    130                 135                 140

Val Gly Asn His Glu Ala Ser Gln Leu Leu Pro Thr Asn Pro Tyr Ser
145                 150                 155                 160

Ala Thr Lys Ala Gly Ala Glu Met Leu Val Met Ala Tyr Gly Arg Ser
                165                 170                 175

Tyr Gly Leu Pro Val Ile Thr Thr Arg Gly Asn Asn Val Tyr Gly Pro
            180                 185                 190

Asn Gln Phe Pro Glu Lys Leu Ile Pro Lys Phe Ile Leu Leu Ser Met
        195                 200                 205

Arg Gly Lys Pro Leu Thr Ile His Gly Asp Gly Ser Asn Val Arg Ser
    210                 215                 220

Tyr Leu Tyr Cys Glu Asp Val Ala Glu Ala Phe Glu Val Val Leu His
225                 230                 235                 240

Lys Gly Glu Val Gly His Val Tyr Asn Ile Gly Thr Lys Lys Glu Arg
                245                 250                 255

Arg Val Ile Asp Val Ala Lys Asp Ile Cys Asn Leu Phe Glu Ile Asp
            260                 265                 270
```

```
His Glu Ser Arg Ile Lys Phe Val Glu Asn Arg Pro Phe Asn Asp Gln
        275                 280                 285

Arg Tyr Phe Leu Asp Asp Glu Lys Leu Lys Ser Leu Gly Trp Val Glu
        290                 295                 300

Arg Thr Thr Trp Gln Glu Gly Leu Lys Lys Thr Met Lys Trp Tyr Thr
305                 310                 315                 320

Met Asn Pro Asp Trp Trp Gly Asp Val Ser Gly Ala Leu Leu Pro His
                325                 330                 335

Pro Arg Met Leu Met Met Pro Gly Gly Ile Gln Ser Asp Ser Pro His
            340                 345                 350

Ser Gly Ile Ile Ser Thr Pro Met Glu Lys Pro Gly His Leu Ser Gly
        355                 360                 365

Pro Gly Ile Asn Ser Ser Asn Lys Pro Gly Phe Lys Phe Leu Ile Tyr
        370                 375                 380

Gly Arg Thr Gly Trp Ile Gly Gly Leu Leu Gly Lys Leu Cys Glu Lys
385                 390                 395                 400

Gln Gly Ile Gln Tyr Glu Tyr Gly Lys Gly Arg Leu Glu Asn Arg Ala
            405                 410                 415

Gln Ile Val Ser Asp Ile Gln Asn Val Lys Pro Thr His Val Phe Asn
            420                 425                 430

Ala Ala Gly Val Thr Gly Arg Pro Asn Val Asp Trp Cys Glu Ser His
            435                 440                 445

Lys Thr Glu Thr Ile Arg Thr Asn Val Ser Gly Thr Leu Asn Leu Ala
        450                 455                 460

Asp Val Cys Arg Glu Asn Gly Ile Leu Met Met Asn Phe Ala Thr Gly
465                 470                 475                 480

Cys Ile Phe Glu Tyr Asp Asp Ala His Pro Glu Gly Ser Gly Ile Gly
                485                 490                 495

Phe Lys Glu Glu Asp Thr Pro Asn Phe Thr Gly Ser Phe Tyr Ser Lys
            500                 505                 510

Thr Lys Ala Met Val Glu Glu Leu Leu Lys Glu Tyr Asp Asn Val Cys
        515                 520                 525

Thr Leu Arg Val Arg Met Pro Ile Ser Ser Asp Leu Asn Asn Pro Arg
530                 535                 540

Asn Phe Ile Thr Lys Ile Ala Arg Tyr Asp Lys Val Val Asn Ile Pro
545                 550                 555                 560

Asn Ser Met Thr Ile Leu Asp Glu Leu Leu Pro Ile Ser Ile Glu Met
            565                 570                 575

Ala Lys Arg Asn Leu Lys Gly Ile Trp Asn Phe Thr Asn Pro Gly Val
        580                 585                 590

Val Ser His Asn Glu Val Leu Glu Met Tyr Lys Asp Tyr Ile Asn Pro
        595                 600                 605

Glu Phe Lys Trp Lys Asn Phe Thr Leu Glu Gln Glu Arg Val Ile
        610                 615                 620

Val Ala Pro Arg Ser Asn Asn Glu Leu Asp Thr Ser Lys Leu Lys Lys
625                 630                 635                 640

Glu Phe Pro Glu Leu Leu Ser Ile Lys Glu Ser Leu Val Lys Tyr Val
                645                 650                 655

Phe Ala Pro Asn Lys Thr Thr
            660
```

```
<210> SEQ ID NO 9
<211> LENGTH: 1992
<212> TYPE: DNA
<213> ORGANISM: Stevia rebaudiana
<220> FEATURE:
<221> NAME/KEY: CDS
<222> LOCATION: (1)..(1992)

<400> SEQUENCE: 9
```

| | | | | | | | | | | | | | | | | |
|---|---|---|---|---|---|---|---|---|---|---|---|---|---|---|---|---|
| atg | acc | agt | tat | aca | cct | aaa | aac | atc | ctc | atc | act | ggg | gca | gct | gga | 48 |
| Met | Thr | Ser | Tyr | Thr | Pro | Lys | Asn | Ile | Leu | Ile | Thr | Gly | Ala | Ala | Gly | |
| 1 | | | | 5 | | | | | 10 | | | | | 15 | | |
| ttc | atc | gcc | tct | cat | gta | gct | aat | cgt | ctt | gtt | aga | acc | tat | ccg | gat | 96 |
| Phe | Ile | Ala | Ser | His | Val | Ala | Asn | Arg | Leu | Val | Arg | Thr | Tyr | Pro | Asp | |
| | | | 20 | | | | | 25 | | | | | 30 | | | |
| tac | aaa | att | gtt | gtg | ctt | gac | aag | ctt | gat | tac | tgc | tca | aat | ctc | aaa | 144 |
| Tyr | Lys | Ile | Val | Val | Leu | Asp | Lys | Leu | Asp | Tyr | Cys | Ser | Asn | Leu | Lys | |
| | 35 | | | | | 40 | | | | | 45 | | | | | |
| aac | cta | aac | ccc | tct | aaa | tca | tct | ccc | aat | ttc | aaa | ttc | gtt | aaa | gga | 192 |
| Asn | Leu | Asn | Pro | Ser | Lys | Ser | Ser | Pro | Asn | Phe | Lys | Phe | Val | Lys | Gly | |
| 50 | | | | | 55 | | | | | 60 | | | | | | |
| gac | atc | gca | agt | gcg | gat | cta | gtc | aat | cat | ttg | tta | ctc | acc | gaa | tcc | 240 |
| Asp | Ile | Ala | Ser | Ala | Asp | Leu | Val | Asn | His | Leu | Leu | Leu | Thr | Glu | Ser | |
| 65 | | | | | 70 | | | | | 75 | | | | | 80 | |
| atc | gac | acc | ata | atg | cac | ttt | gca | gct | caa | act | cat | gtc | gac | aac | tca | 288 |
| Ile | Asp | Thr | Ile | Met | His | Phe | Ala | Ala | Gln | Thr | His | Val | Asp | Asn | Ser | |
| | | | | 85 | | | | | 90 | | | | | 95 | | |
| ttt | ggt | aac | agc | ttc | gag | ttc | aca | aag | aac | aac | ata | tac | ggc | aca | cat | 336 |
| Phe | Gly | Asn | Ser | Phe | Glu | Phe | Thr | Lys | Asn | Asn | Ile | Tyr | Gly | Thr | His | |
| | | | 100 | | | | | 105 | | | | | 110 | | | |
| gtt | ctt | cta | gaa | gcc | tgc | aaa | gtc | acc | cgc | cag | atc | aaa | cgg | ttc | atc | 384 |
| Val | Leu | Leu | Glu | Ala | Cys | Lys | Val | Thr | Arg | Gln | Ile | Lys | Arg | Phe | Ile | |
| | | 115 | | | | | 120 | | | | | 125 | | | | |
| cac | gtc | agc | acc | gat | gag | gtg | tat | ggt | gaa | aca | gat | gaa | gat | gct | gtt | 432 |
| His | Val | Ser | Thr | Asp | Glu | Val | Tyr | Gly | Glu | Thr | Asp | Glu | Asp | Ala | Val | |
| | 130 | | | | | 135 | | | | | 140 | | | | | |
| gtg | ggt | aac | cat | gaa | gcc | tca | caa | ctt | ctt | cct | aca | aat | ccg | tat | tcc | 480 |
| Val | Gly | Asn | His | Glu | Ala | Ser | Gln | Leu | Leu | Pro | Thr | Asn | Pro | Tyr | Ser | |
| 145 | | | | | 150 | | | | | 155 | | | | | 160 | |
| gcc | aca | aaa | gcc | ggt | gca | gaa | atg | ctc | gtt | atg | gct | tat | ggt | aga | tca | 528 |
| Ala | Thr | Lys | Ala | Gly | Ala | Glu | Met | Leu | Val | Met | Ala | Tyr | Gly | Arg | Ser | |
| | | | | 165 | | | | | 170 | | | | | 175 | | |
| tac | ggg | tta | ccc | gtg | atc | acc | act | aga | gga | aac | aac | gtt | tat | ggc | ccg | 576 |
| Tyr | Gly | Leu | Pro | Val | Ile | Thr | Thr | Arg | Gly | Asn | Asn | Val | Tyr | Gly | Pro | |
| | | | 180 | | | | | 185 | | | | | 190 | | | |
| aat | caa | ttt | cct | gaa | aaa | cta | atc | cct | aaa | ttc | att | ctt | tta | tcc | atg | 624 |
| Asn | Gln | Phe | Pro | Glu | Lys | Leu | Ile | Pro | Lys | Phe | Ile | Leu | Leu | Ser | Met | |
| | | 195 | | | | | 200 | | | | | 205 | | | | |
| aga | ggc | aaa | ccg | tta | acg | att | cat | ggt | gac | gga | tcg | aat | gtc | aga | agt | 672 |
| Arg | Gly | Lys | Pro | Leu | Thr | Ile | His | Gly | Asp | Gly | Ser | Asn | Val | Arg | Ser | |
| | 210 | | | | | 215 | | | | | 220 | | | | | |
| tat | ctt | tac | tgt | gaa | gat | gtt | gca | gaa | gca | ttt | gaa | gtc | gtg | tta | cat | 720 |
| Tyr | Leu | Tyr | Cys | Glu | Asp | Val | Ala | Glu | Ala | Phe | Glu | Val | Val | Leu | His | |
| 225 | | | | | 230 | | | | | 235 | | | | | 240 | |
| aaa | gga | gaa | gtt | gga | cat | gtt | tac | aac | att | gga | acc | aaa | aaa | gaa | aga | 768 |
| Lys | Gly | Glu | Val | Gly | His | Val | Tyr | Asn | Ile | Gly | Thr | Lys | Lys | Glu | Arg | |
| | | | | 245 | | | | | 250 | | | | | 255 | | |
| cga | gtg | att | gat | gtt | gct | aaa | gat | ata | tgc | aat | ctt | ttt | gaa | atc | gat | 816 |
| Arg | Val | Ile | Asp | Val | Ala | Lys | Asp | Ile | Cys | Asn | Leu | Phe | Glu | Ile | Asp | |
| | | | 260 | | | | | 265 | | | | | 270 | | | |

```
cat gaa tca aga atc aaa ttt gtt gaa aac aga cct ttt aac gat caa      864
His Glu Ser Arg Ile Lys Phe Val Glu Asn Arg Pro Phe Asn Asp Gln
        275                 280                 285 aga tac ttt tta gat gat gaa aag ctc aag agt ttg ggc tgg gtt gaa      912
Arg Tyr Phe Leu Asp Asp Glu Lys Leu Lys Ser Leu Gly Trp Val Glu
    290                 295                 300 aga acc acg tgg caa gag ggt ttg aaa aaa act atg gaa tgg tat acc      960
Arg Thr Thr Trp Gln Glu Gly Leu Lys Lys Thr Met Glu Trp Tyr Thr
305                 310                 315                 320 atg aat cct gat tgg tgg ggt gac gtg tca ggt gca ttg ctt cct cat     1008
Met Asn Pro Asp Trp Trp Gly Asp Val Ser Gly Ala Leu Leu Pro His
                325                 330                 335 cca cgt atg ctg atg atg cca ggt ggc att caa tct gac tca cct cat     1056
Pro Arg Met Leu Met Met Pro Gly Gly Ile Gln Ser Asp Ser Pro His
            340                 345                 350 tct gga atc atc tct act ccg atg gaa aaa ccg ggt cat ctt tca gga     1104
Ser Gly Ile Ile Ser Thr Pro Met Glu Lys Pro Gly His Leu Ser Gly
        355                 360                 365 ccc ggt aca aat tct tcc aac aaa ccg ggt ttt aag ttc ttg att tac     1152
Pro Gly Thr Asn Ser Ser Asn Lys Pro Gly Phe Lys Phe Leu Ile Tyr
370                 375                 380 ggt cga acc ggg tgg atc ggt ggt tta ctt ggg aag tta tgt gaa aaa     1200
Gly Arg Thr Gly Trp Ile Gly Gly Leu Leu Gly Lys Leu Cys Glu Lys
385                 390                 395                 400 caa ggg att cag tac gag tac gga aag ggt cgg ttg gag aac cgg gcc     1248
Gln Gly Ile Gln Tyr Glu Tyr Gly Lys Gly Arg Leu Glu Asn Arg Ala
                405                 410                 415 caa att gtt tcg gat att cag aac gtt aaa ccg acc cat gtt ttt aac     1296
Gln Ile Val Ser Asp Ile Gln Asn Val Lys Pro Thr His Val Phe Asn
            420                 425                 430 gcg gct ggt gtt acg ggt cga ccg aat gtg gat tgg tgt gaa tct cat     1344
Ala Ala Gly Val Thr Gly Arg Pro Asn Val Asp Trp Cys Glu Ser His
        435                 440                 445 aaa act gaa acg att cgc acc aat gtt tca gga acc cta aat ttg gca     1392
Lys Thr Glu Thr Ile Arg Thr Asn Val Ser Gly Thr Leu Asn Leu Ala
450                 455                 460 gat gtt tgc agg gaa aat ggg atc ttg atg atg aac ttt gct act gga     1440
Asp Val Cys Arg Glu Asn Gly Ile Leu Met Met Asn Phe Ala Thr Gly
465                 470                 475                 480 tgc ata ttt gaa tac gat gat gca cat cct gaa ggt tct gga atc ggg     1488
Cys Ile Phe Glu Tyr Asp Asp Ala His Pro Glu Gly Ser Gly Ile Gly
                485                 490                 495 ttt aaa gaa gaa gac aca ccc aat ttc acc ggt tca ttc tat tcc aaa     1536
Phe Lys Glu Glu Asp Thr Pro Asn Phe Thr Gly Ser Phe Tyr Ser Lys
            500                 505                 510 acc aaa gct atg gtt gag gag ctt ttg aaa gaa tat gac aac gtg tgc     1584
Thr Lys Ala Met Val Glu Glu Leu Leu Lys Glu Tyr Asp Asn Val Cys
        515                 520                 525 aca ctt cgt gtc cgt atg cca ata tct tca gac ctt aac aat cca cgt     1632
Thr Leu Arg Val Arg Met Pro Ile Ser Ser Asp Leu Asn Asn Pro Arg
530                 535                 540 aat ttt ata act aaa atc gcg cgt tat gat aag gtt gta aat att cca     1680
Asn Phe Ile Thr Lys Ile Ala Arg Tyr Asp Lys Val Val Asn Ile Pro
545                 550                 555                 560 aac tcg atg acg att tta gat gag ctt tta cct att tca ata gaa atg     1728
Asn Ser Met Thr Ile Leu Asp Glu Leu Leu Pro Ile Ser Ile Glu Met
                565                 570                 575 gca aag aga aat tta aaa gga ata tgg aat ttt aca aac ccg ggg gtt     1776
Ala Lys Arg Asn Leu Lys Gly Ile Trp Asn Phe Thr Asn Pro Gly Val
            580                 585                 590
```

```
gtg agt cat aac gag gtt ttg gaa atg tat aaa gat tat ata aac ccg      1824
Val Ser His Asn Glu Val Leu Glu Met Tyr Lys Asp Tyr Ile Asn Pro
    595                 600                 605 gaa ttt aaa tgg aaa aat ttc aca ctt gaa gaa caa gaa cgt gtg att      1872
Glu Phe Lys Trp Lys Asn Phe Thr Leu Glu Glu Gln Glu Arg Val Ile
610                 615                 620 gtt gca cca aga agt aat aat gag ttg gat aca tcc aag ttg aag aaa      1920
Val Ala Pro Arg Ser Asn Asn Glu Leu Asp Thr Ser Lys Leu Lys Lys
625                 630                 635                 640 gag ttt cct gaa ttg ctg tcg att aaa gaa tca ttg gtt aaa tac gta      1968
Glu Phe Pro Glu Leu Leu Ser Ile Lys Glu Ser Leu Val Lys Tyr Val
                645                 650                 655 ttt gca ccc aac aag aca acc taa                                      1992
Phe Ala Pro Asn Lys Thr Thr
            660
```

<210> SEQ ID NO 10
<211> LENGTH: 663
<212> TYPE: PRT
<213> ORGANISM: Stevia rebaudiana

<400> SEQUENCE: 10

```
Met Thr Ser Tyr Thr Pro Lys Asn Ile Leu Ile Thr Gly Ala Ala Gly
1               5                   10                  15

Phe Ile Ala Ser His Val Ala Asn Arg Leu Val Arg Thr Tyr Pro Asp
                20                  25                  30

Tyr Lys Ile Val Val Leu Asp Lys Leu Asp Tyr Cys Ser Asn Leu Lys
            35                  40                  45

Asn Leu Asn Pro Ser Lys Ser Ser Pro Asn Phe Lys Phe Val Lys Gly
    50                  55                  60

Asp Ile Ala Ser Ala Asp Leu Val Asn His Leu Leu Leu Thr Glu Ser
65                  70                  75                  80

Ile Asp Thr Ile Met His Phe Ala Ala Gln Thr His Val Asp Asn Ser
                85                  90                  95

Phe Gly Asn Ser Phe Glu Phe Thr Lys Asn Asn Ile Tyr Gly Thr His
            100                 105                 110

Val Leu Leu Glu Ala Cys Lys Val Thr Arg Gln Ile Lys Arg Phe Ile
        115                 120                 125

His Val Ser Thr Asp Glu Val Tyr Gly Glu Thr Asp Glu Asp Ala Val
    130                 135                 140

Val Gly Asn His Glu Ala Ser Gln Leu Leu Pro Thr Asn Pro Tyr Ser
145                 150                 155                 160

Ala Thr Lys Ala Gly Ala Glu Met Leu Val Met Ala Tyr Gly Arg Ser
                165                 170                 175

Tyr Gly Leu Pro Val Ile Thr Thr Arg Gly Asn Asn Val Tyr Gly Pro
            180                 185                 190

Asn Gln Phe Pro Glu Lys Leu Ile Pro Lys Phe Ile Leu Leu Ser Met
        195                 200                 205

Arg Gly Lys Pro Leu Thr Ile His Gly Asp Gly Ser Asn Val Arg Ser
    210                 215                 220

Tyr Leu Tyr Cys Glu Asp Val Ala Glu Ala Phe Glu Val Val Leu His
225                 230                 235                 240

Lys Gly Glu Val Gly His Val Tyr Asn Ile Gly Thr Lys Lys Glu Arg
                245                 250                 255

Arg Val Ile Asp Val Ala Lys Asp Ile Cys Asn Leu Phe Glu Ile Asp
            260                 265                 270
```

```
His Glu Ser Arg Ile Lys Phe Val Glu Asn Arg Pro Phe Asn Asp Gln
            275                 280                 285

Arg Tyr Phe Leu Asp Asp Glu Lys Leu Lys Ser Leu Gly Trp Val Glu
        290                 295                 300

Arg Thr Thr Trp Gln Glu Gly Leu Lys Lys Thr Met Glu Trp Tyr Thr
305                 310                 315                 320

Met Asn Pro Asp Trp Trp Gly Asp Val Ser Gly Ala Leu Leu Pro His
                325                 330                 335

Pro Arg Met Leu Met Met Pro Gly Gly Ile Gln Ser Asp Ser Pro His
            340                 345                 350

Ser Gly Ile Ile Ser Thr Pro Met Glu Lys Pro Gly His Leu Ser Gly
        355                 360                 365

Pro Gly Thr Asn Ser Ser Asn Lys Pro Gly Phe Lys Phe Leu Ile Tyr
    370                 375                 380

Gly Arg Thr Gly Trp Ile Gly Gly Leu Leu Gly Lys Leu Cys Glu Lys
385                 390                 395                 400

Gln Gly Ile Gln Tyr Glu Tyr Gly Lys Gly Arg Leu Glu Asn Arg Ala
                405                 410                 415

Gln Ile Val Ser Asp Ile Gln Asn Val Lys Pro Thr His Val Phe Asn
            420                 425                 430

Ala Ala Gly Val Thr Gly Arg Pro Asn Val Asp Trp Cys Glu Ser His
        435                 440                 445

Lys Thr Glu Thr Ile Arg Thr Asn Val Ser Gly Thr Leu Asn Leu Ala
    450                 455                 460

Asp Val Cys Arg Glu Asn Gly Ile Leu Met Met Asn Phe Ala Thr Gly
465                 470                 475                 480

Cys Ile Phe Glu Tyr Asp Asp Ala His Pro Glu Gly Ser Gly Ile Gly
                485                 490                 495

Phe Lys Glu Glu Asp Thr Pro Asn Phe Thr Gly Ser Phe Tyr Ser Lys
            500                 505                 510

Thr Lys Ala Met Val Glu Glu Leu Leu Lys Glu Tyr Asp Asn Val Cys
        515                 520                 525

Thr Leu Arg Val Arg Met Pro Ile Ser Ser Asp Leu Asn Asn Pro Arg
    530                 535                 540

Asn Phe Ile Thr Lys Ile Ala Arg Tyr Asp Lys Val Val Asn Ile Pro
545                 550                 555                 560

Asn Ser Met Thr Ile Leu Asp Glu Leu Leu Pro Ile Ser Ile Glu Met
                565                 570                 575

Ala Lys Arg Asn Leu Lys Gly Ile Trp Asn Phe Thr Asn Pro Gly Val
            580                 585                 590

Val Ser His Asn Glu Val Leu Glu Met Tyr Lys Asp Tyr Ile Asn Pro
        595                 600                 605

Glu Phe Lys Trp Lys Asn Phe Thr Leu Glu Gln Glu Arg Val Ile
    610                 615                 620

Val Ala Pro Arg Ser Asn Asn Glu Leu Asp Thr Ser Lys Leu Lys Lys
625                 630                 635                 640

Glu Phe Pro Glu Leu Leu Ser Ile Lys Glu Ser Leu Val Lys Tyr Val
                645                 650                 655

Phe Ala Pro Asn Lys Thr Thr
            660
```

```
<210> SEQ ID NO 11
<211> LENGTH: 1458
<212> TYPE: DNA
<213> ORGANISM: Stevia rebaudiana
<220> FEATURE:
<221> NAME/KEY: CDS
<222> LOCATION: (1)..(1458)

<400> SEQUENCE: 11 atg tac aac gtt act tat cat caa aat tca aaa gca atg gct acc agt       48
Met Tyr Asn Val Thr Tyr His Gln Asn Ser Lys Ala Met Ala Thr Ser
1               5                  10                  15 gac tcc ata gtt gac gac cgt aag cag ctt cat gtt gcg acg ttc cca       96
Asp Ser Ile Val Asp Asp Arg Lys Gln Leu His Val Ala Thr Phe Pro
            20                  25                  30 tgg ctt gct ttc ggt cac atc ctc cct tac ctt cag ctt tcg aaa ttg      144
Trp Leu Ala Phe Gly His Ile Leu Pro Tyr Leu Gln Leu Ser Lys Leu
        35                  40                  45 ata gct gaa aag ggt cac aaa gtc tcg ttt ctt tct acc acc aga aac      192
Ile Ala Glu Lys Gly His Lys Val Ser Phe Leu Ser Thr Thr Arg Asn
    50                  55                  60 att caa cgt ctc tct tct cat atc tcg cca ctc ata aat gtt gtt caa      240
Ile Gln Arg Leu Ser Ser His Ile Ser Pro Leu Ile Asn Val Val Gln
65                  70                  75                  80 ctc aca ctt cca cgt gtc caa gag ctg ccg gag gat gca gag gcg acc      288
Leu Thr Leu Pro Arg Val Gln Glu Leu Pro Glu Asp Ala Glu Ala Thr
                85                  90                  95 act gac gtc cac cct gaa gat att cca tat ctc aag aag gct tct gat      336
Thr Asp Val His Pro Glu Asp Ile Pro Tyr Leu Lys Lys Ala Ser Asp
            100                 105                 110 ggt ctt caa ccg gag gtc acc cgg ttt cta gaa caa cac tct ccg gac      384
Gly Leu Gln Pro Glu Val Thr Arg Phe Leu Glu Gln His Ser Pro Asp
        115                 120                 125 tgg att att tat gat tat act cac tac tgg ttg cca tcc atc gcg gct      432
Trp Ile Ile Tyr Asp Tyr Thr His Tyr Trp Leu Pro Ser Ile Ala Ala
    130                 135                 140 agc ctc ggt atc tca cga gcc cac ttc tcc gtc acc act cca tgg gcc      480
Ser Leu Gly Ile Ser Arg Ala His Phe Ser Val Thr Thr Pro Trp Ala
145                 150                 155                 160 att gct tat atg gga ccc tca gct gac gcc atg ata aat ggt tca gat      528
Ile Ala Tyr Met Gly Pro Ser Ala Asp Ala Met Ile Asn Gly Ser Asp
                165                 170                 175 ggt cga acc acg gtt gag gat ctc acg aca ccg ccc aag tgg ttt ccc      576
Gly Arg Thr Thr Val Glu Asp Leu Thr Thr Pro Pro Lys Trp Phe Pro
            180                 185                 190 ttt ccg acc aaa gta tgc tgg cgg aag cat gat ctt gcc cga ctg gtg      624
Phe Pro Thr Lys Val Cys Trp Arg Lys His Asp Leu Ala Arg Leu Val
        195                 200                 205 cct tac aaa gct ccg ggg ata tct gat gga tac cgt atg ggg ctg gtt      672
Pro Tyr Lys Ala Pro Gly Ile Ser Asp Gly Tyr Arg Met Gly Leu Val
    210                 215                 220 ctt aag gga tct gat tgt ttg ctt tcc aaa tgt tac cat gag ttt gga      720
Leu Lys Gly Ser Asp Cys Leu Leu Ser Lys Cys Tyr His Glu Phe Gly
225                 230                 235                 240 act caa tgg cta cct ctt ttg gag aca cta cac caa gta ccg gtg gtt      768
Thr Gln Trp Leu Pro Leu Leu Glu Thr Leu His Gln Val Pro Val Val
                245                 250                 255 ccg gtg gga tta ctg cca ccg gaa ata ccc gga gac gag aaa gat gaa      816
Pro Val Gly Leu Leu Pro Pro Glu Ile Pro Gly Asp Glu Lys Asp Glu
            260                 265                 270
```

| | | |
|---|---|---|
| aca tgg gtg tca atc aag aaa tgg ctc gat ggt aaa caa aaa ggc agt<br>Thr Trp Val Ser Ile Lys Lys Trp Leu Asp Gly Lys Gln Lys Gly Ser<br>           275                   280                   285 | | 864 |
| gtg gtg tac gtt gca tta gga agc gag gtt ttg gtg agc caa acc gag<br>Val Val Tyr Val Ala Leu Gly Ser Glu Val Leu Val Ser Gln Thr Glu<br>       290                   295                   300 | | 912 |
| gtt gtt gag tta gca ttg ggt ctc gag ctt tct ggg ttg cca ttt gtt<br>Val Val Glu Leu Ala Leu Gly Leu Glu Leu Ser Gly Leu Pro Phe Val<br>305                   310                   315                 320 | | 960 |
| tgg gct tat aga aaa cca aaa ggt ccc gcg aag tca gac tcg gtg gag<br>Trp Ala Tyr Arg Lys Pro Lys Gly Pro Ala Lys Ser Asp Ser Val Glu<br>             325                   330                   335 | | 1008 |
| ttg cca gac ggg ttc gtg gaa cga act cgt gac cgt ggg ttg gtc tgg<br>Leu Pro Asp Gly Phe Val Glu Arg Thr Arg Asp Arg Gly Leu Val Trp<br>                 340                   345                   350 | | 1056 |
| acg agt tgg gca cct cag tta cga ata ctg agc cat gag tcg gtt tgt<br>Thr Ser Trp Ala Pro Gln Leu Arg Ile Leu Ser His Glu Ser Val Cys<br>             355                   360                   365 | | 1104 |
| ggt ttc ttg act cat tgt ggt tct gga tca att gtg gaa ggg cta atg<br>Gly Phe Leu Thr His Cys Gly Ser Gly Ser Ile Val Glu Gly Leu Met<br>370                   375                   380 | | 1152 |
| ttt ggt cac cct cta atc atg cta ccg att ttt ggg gac caa cct ctg<br>Phe Gly His Pro Leu Ile Met Leu Pro Ile Phe Gly Asp Gln Pro Leu<br>385                   390                   395                 400 | | 1200 |
| aat gct cga tta ctg gag gac aaa cag gtg gga atc gag ata cca aga<br>Asn Ala Arg Leu Leu Glu Asp Lys Gln Val Gly Ile Glu Ile Pro Arg<br>                 405                   410                   415 | | 1248 |
| aat gag gaa gat ggt tgc ttg acc aag gag tcg gtt gct aga tca ctg<br>Asn Glu Glu Asp Gly Cys Leu Thr Lys Glu Ser Val Ala Arg Ser Leu<br>                 420                   425                   430 | | 1296 |
| agg tcc gtt gtt gtg gaa aaa gaa ggg gag atc tac aag gcg aac gcg<br>Arg Ser Val Val Val Glu Lys Glu Gly Glu Ile Tyr Lys Ala Asn Ala<br>             435                   440                   445 | | 1344 |
| agg gag ctg agt aaa atc tat aac gac act aag gtt gaa aaa gaa tat<br>Arg Glu Leu Ser Lys Ile Tyr Asn Asp Thr Lys Val Glu Lys Glu Tyr<br>450                   455                   460 | | 1392 |
| gta agc caa ttc gta gac tat ttg gaa aag aat gcg cgt gcg gtt gcc<br>Val Ser Gln Phe Val Asp Tyr Leu Glu Lys Asn Ala Arg Ala Val Ala<br>465                   470                   475                 480 | | 1440 |
| atc gat cat gag agt taa<br>Ile Asp His Glu Ser<br>             485 | | 1458 |

<210> SEQ ID NO 12
<211> LENGTH: 485
<212> TYPE: PRT
<213> ORGANISM: Stevia rebaudiana

<400> SEQUENCE: 12

Met Tyr Asn Val Thr Tyr His Gln Asn Ser Lys Ala Met Ala Thr Ser
1               5                    10                   15

Asp Ser Ile Val Asp Asp Arg Lys Gln Leu His Val Ala Thr Phe Pro
                20                   25                   30

Trp Leu Ala Phe Gly His Ile Leu Pro Tyr Leu Gln Leu Ser Lys Leu
         35                   40                   45

Ile Ala Glu Lys Gly His Lys Val Ser Phe Leu Ser Thr Thr Arg Asn
    50                   55                   60

Ile Gln Arg Leu Ser Ser His Ile Ser Pro Leu Ile Asn Val Val Gln
65                  70                   75                  80

```
Leu Thr Leu Pro Arg Val Gln Glu Leu Pro Glu Asp Ala Glu Ala Thr
                 85                  90                  95

Thr Asp Val His Pro Glu Asp Ile Pro Tyr Leu Lys Lys Ala Ser Asp
            100                 105                 110

Gly Leu Gln Pro Glu Val Thr Arg Phe Leu Glu Gln His Ser Pro Asp
            115                 120                 125

Trp Ile Ile Tyr Asp Tyr Thr His Tyr Trp Leu Pro Ser Ile Ala Ala
            130                 135                 140

Ser Leu Gly Ile Ser Arg Ala His Phe Ser Val Thr Thr Pro Trp Ala
145                 150                 155                 160

Ile Ala Tyr Met Gly Pro Ser Ala Asp Ala Met Ile Asn Gly Ser Asp
                165                 170                 175

Gly Arg Thr Thr Val Glu Asp Leu Thr Thr Pro Pro Lys Trp Phe Pro
                180                 185                 190

Phe Pro Thr Lys Val Cys Trp Arg Lys His Asp Leu Ala Arg Leu Val
            195                 200                 205

Pro Tyr Lys Ala Pro Gly Ile Ser Asp Gly Tyr Arg Met Gly Leu Val
            210                 215                 220

Leu Lys Gly Ser Asp Cys Leu Leu Ser Lys Cys Tyr His Glu Phe Gly
225                 230                 235                 240

Thr Gln Trp Leu Pro Leu Leu Glu Thr Leu His Gln Val Pro Val Val
                245                 250                 255

Pro Val Gly Leu Leu Pro Pro Glu Ile Pro Gly Asp Glu Lys Asp Glu
                260                 265                 270

Thr Trp Val Ser Ile Lys Lys Trp Leu Asp Gly Lys Gln Lys Gly Ser
            275                 280                 285

Val Val Tyr Val Ala Leu Gly Ser Glu Val Leu Val Ser Gln Thr Glu
            290                 295                 300

Val Val Glu Leu Ala Leu Gly Leu Glu Leu Ser Gly Leu Pro Phe Val
305                 310                 315                 320

Trp Ala Tyr Arg Lys Pro Lys Gly Pro Ala Lys Ser Asp Ser Val Glu
                325                 330                 335

Leu Pro Asp Gly Phe Val Glu Arg Thr Arg Asp Arg Gly Leu Val Trp
                340                 345                 350

Thr Ser Trp Ala Pro Gln Leu Arg Ile Leu Ser His Glu Ser Val Cys
            355                 360                 365

Gly Phe Leu Thr His Cys Gly Ser Gly Ser Ile Val Glu Gly Leu Met
            370                 375                 380

Phe Gly His Pro Leu Ile Met Leu Pro Ile Phe Gly Asp Gln Pro Leu
385                 390                 395                 400

Asn Ala Arg Leu Leu Glu Asp Lys Gln Val Gly Ile Glu Ile Pro Arg
                405                 410                 415

Asn Glu Glu Asp Gly Cys Leu Thr Lys Glu Ser Val Ala Arg Ser Leu
            420                 425                 430

Arg Ser Val Val Val Glu Lys Glu Gly Glu Ile Tyr Lys Ala Asn Ala
            435                 440                 445

Arg Glu Leu Ser Lys Ile Tyr Asn Asp Thr Lys Val Glu Lys Glu Tyr
            450                 455                 460

Val Ser Gln Phe Val Asp Tyr Leu Glu Lys Asn Ala Arg Ala Val Ala
465                 470                 475                 480

Ile Asp His Glu Ser
                485
```

```
<210> SEQ ID NO 13
<211> LENGTH: 1458
<212> TYPE: DNA
<213> ORGANISM: Stevia rebaudiana
<220> FEATURE:
<221> NAME/KEY: CDS
<222> LOCATION: (1)..(1458)

<400> SEQUENCE: 13
```

| | | | | | | | | | | | | | | | | |
|---|---|---|---|---|---|---|---|---|---|---|---|---|---|---|---|---|
| atg | tac | aac | gtt | act | tat | cat | caa | aat | tca | aaa | gca | atg | gct | acc | agt | 48 |
| Met | Tyr | Asn | Val | Thr | Tyr | His | Gln | Asn | Ser | Lys | Ala | Met | Ala | Thr | Ser | |
| 1 | | | | 5 | | | | | 10 | | | | | 15 | | |
| gac | tcc | ata | gtt | gac | gac | cgt | aag | cag | ctt | cat | gtt | gcg | acg | ttc | cca | 96 |
| Asp | Ser | Ile | Val | Asp | Asp | Arg | Lys | Gln | Leu | His | Val | Ala | Thr | Phe | Pro | |
| | | | 20 | | | | | 25 | | | | | 30 | | | |
| tgg | ctt | gct | ttc | ggt | cac | atc | ctc | cct | ttc | ctt | cag | ctt | tcg | aaa | ttg | 144 |
| Trp | Leu | Ala | Phe | Gly | His | Ile | Leu | Pro | Phe | Leu | Gln | Leu | Ser | Lys | Leu | |
| | | 35 | | | | | 40 | | | | | 45 | | | | |
| ata | gct | gaa | aag | ggt | cac | aaa | gtc | tcg | ttt | ctt | tct | acc | acc | aga | aac | 192 |
| Ile | Ala | Glu | Lys | Gly | His | Lys | Val | Ser | Phe | Leu | Ser | Thr | Thr | Arg | Asn | |
| | 50 | | | | | 55 | | | | | 60 | | | | | |
| att | caa | cgt | ctc | tct | tct | cat | atc | tcg | cca | ctc | ata | aat | gtt | gtt | caa | 240 |
| Ile | Gln | Arg | Leu | Ser | Ser | His | Ile | Ser | Pro | Leu | Ile | Asn | Val | Val | Gln | |
| 65 | | | | | 70 | | | | | 75 | | | | | 80 | |
| ctc | aca | ctt | cca | cgt | gtc | caa | gag | ctg | ccg | gag | gat | gca | gag | gcg | acc | 288 |
| Leu | Thr | Leu | Pro | Arg | Val | Gln | Glu | Leu | Pro | Glu | Asp | Ala | Glu | Ala | Thr | |
| | | | | 85 | | | | | 90 | | | | | 95 | | |
| act | gac | gtc | cac | cct | gaa | gat | att | cca | tat | ctc | aag | aag | gct | tct | gat | 336 |
| Thr | Asp | Val | His | Pro | Glu | Asp | Ile | Pro | Tyr | Leu | Lys | Lys | Ala | Ser | Asp | |
| | | | 100 | | | | | 105 | | | | | 110 | | | |
| ggt | ctt | caa | ccg | gag | gtc | acc | cgg | ttt | cta | gaa | caa | cac | tct | ccg | gac | 384 |
| Gly | Leu | Gln | Pro | Glu | Val | Thr | Arg | Phe | Leu | Glu | Gln | His | Ser | Pro | Asp | |
| | | 115 | | | | | 120 | | | | | 125 | | | | |
| tgg | att | att | tat | gat | tat | act | cac | tac | tgg | ttg | cca | tcc | atc | gcg | gct | 432 |
| Trp | Ile | Ile | Tyr | Asp | Tyr | Thr | His | Tyr | Trp | Leu | Pro | Ser | Ile | Ala | Ala | |
| | 130 | | | | | 135 | | | | | 140 | | | | | |
| agc | ctc | ggt | atc | tca | cga | gcc | cac | ttc | tcc | gtc | gtc | act | cca | tgg | gcc | 480 |
| Ser | Leu | Gly | Ile | Ser | Arg | Ala | His | Phe | Ser | Val | Val | Thr | Pro | Trp | Ala | |
| 145 | | | | | 150 | | | | | 155 | | | | | 160 | |
| att | gct | tat | atg | gga | ccc | tca | gct | gac | gcc | atg | ata | aat | ggt | tca | gat | 528 |
| Ile | Ala | Tyr | Met | Gly | Pro | Ser | Ala | Asp | Ala | Met | Ile | Asn | Gly | Ser | Asp | |
| | | | | 165 | | | | | 170 | | | | | 175 | | |
| ggt | cga | acc | acg | gtt | gag | gat | ctc | acg | aca | ccg | ccc | aag | tgg | ttt | ccc | 576 |
| Gly | Arg | Thr | Thr | Val | Glu | Asp | Leu | Thr | Thr | Pro | Pro | Lys | Trp | Phe | Pro | |
| | | | 180 | | | | | 185 | | | | | 190 | | | |
| ttt | ccg | acc | aaa | gta | tgc | tgg | cgg | aag | cat | gat | ctt | gcc | cga | ctg | gtg | 624 |
| Phe | Pro | Thr | Lys | Val | Cys | Trp | Arg | Lys | His | Asp | Leu | Ala | Arg | Leu | Val | |
| | | 195 | | | | | 200 | | | | | 205 | | | | |
| cct | tac | aaa | gct | ccg | ggg | ata | tct | gat | gga | tac | cgt | atg | ggg | ctg | gtt | 672 |
| Pro | Tyr | Lys | Ala | Pro | Gly | Ile | Ser | Asp | Gly | Tyr | Arg | Met | Gly | Leu | Val | |
| | 210 | | | | | 215 | | | | | 220 | | | | | |
| ctt | aag | gga | tct | gat | tgt | ttg | ctt | ttc | aaa | tgt | tac | cat | gag | ttt | gga | 720 |
| Leu | Lys | Gly | Ser | Asp | Cys | Leu | Leu | Phe | Lys | Cys | Tyr | His | Glu | Phe | Gly | |
| 225 | | | | | 230 | | | | | 235 | | | | | 240 | |
| act | caa | tgg | cta | cct | ctt | ttg | gag | aca | cta | cac | caa | gta | ccg | gtg | gtt | 768 |
| Thr | Gln | Trp | Leu | Pro | Leu | Leu | Glu | Thr | Leu | His | Gln | Val | Pro | Val | Val | |
| | | | | 245 | | | | | 250 | | | | | 255 | | |
| ccg | gtg | gga | tta | ctg | cca | ccg | gaa | ata | ccc | gga | gac | gag | aaa | gat | gaa | 816 |
| Pro | Val | Gly | Leu | Leu | Pro | Pro | Glu | Ile | Pro | Gly | Asp | Glu | Lys | Asp | Glu | |
| | | | 260 | | | | | 265 | | | | | 270 | | | |

```
aca tgg gtg tca atc aag aaa tgg ctc gat ggt aaa caa aaa ggc agt      864
Thr Trp Val Ser Ile Lys Lys Trp Leu Asp Gly Lys Gln Lys Gly Ser
        275                 280                 285 gtg gtg tac gtt gca tta gga agc gag gct ttg gtg agc caa acc gag      912
Val Val Tyr Val Ala Leu Gly Ser Glu Ala Leu Val Ser Gln Thr Glu
    290                 295                 300 gtt gtt gag tta gca ttg ggt ctc gag ctt tct ggg ttg cca ttt gtt      960
Val Val Glu Leu Ala Leu Gly Leu Glu Leu Ser Gly Leu Pro Phe Val
305                 310                 315                 320 tgg gct tat aga aaa cca aaa ggt ccc gcg aag tca gac tcg gtg gag     1008
Trp Ala Tyr Arg Lys Pro Lys Gly Pro Ala Lys Ser Asp Ser Val Glu
                325                 330                 335 ttg cca gac ggg ttc gtg gaa cga act cgt gac cgt ggg ttg gtc tgg     1056
Leu Pro Asp Gly Phe Val Glu Arg Thr Arg Asp Arg Gly Leu Val Trp
            340                 345                 350 acg agt tgg gca cct cag tta cga ata ctg agc cat gag tcg gtt tgt     1104
Thr Ser Trp Ala Pro Gln Leu Arg Ile Leu Ser His Glu Ser Val Cys
        355                 360                 365 ggt ttc ttg act cat tgt ggt tct gga tca att gtg gaa ggg cta atg     1152
Gly Phe Leu Thr His Cys Gly Ser Gly Ser Ile Val Glu Gly Leu Met
370                 375                 380 ttt ggt cac cct cta atc atg cta ccg ctt ttt ggg gac caa cct ctg     1200
Phe Gly His Pro Leu Ile Met Leu Pro Leu Phe Gly Asp Gln Pro Leu
385                 390                 395                 400 aat gct cga tta ctg gag gac aaa cag gtg gga atc gag ata cca aga     1248
Asn Ala Arg Leu Leu Glu Asp Lys Gln Val Gly Ile Glu Ile Pro Arg
                405                 410                 415 aat gag gaa gat ggt tgc ttg acc aag gag tcg gtt gct aga tca ctg     1296
Asn Glu Glu Asp Gly Cys Leu Thr Lys Glu Ser Val Ala Arg Ser Leu
            420                 425                 430 agg tcc gtt gtt gtg gaa aac gaa ggg gag atc tac aag gcg aac gcg     1344
Arg Ser Val Val Val Glu Asn Glu Gly Glu Ile Tyr Lys Ala Asn Ala
        435                 440                 445 agg gag ctg agt aaa atc tat aac gac act aag gtg gaa aaa gaa tat     1392
Arg Glu Leu Ser Lys Ile Tyr Asn Asp Thr Lys Val Glu Lys Glu Tyr
450                 455                 460 gta agc caa ttc gta gac ttt ttg gaa aag aat gcg cgt gcg gtt gcc     1440
Val Ser Gln Phe Val Asp Phe Leu Glu Lys Asn Ala Arg Ala Val Ala
465                 470                 475                 480 atc gat cat gag agt taa                                             1458
Ile Asp His Glu Ser
                485

<210> SEQ ID NO 14
<211> LENGTH: 485
<212> TYPE: PRT
<213> ORGANISM: Stevia rebaudiana

<400> SEQUENCE: 14

Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
            20                  25                  30

Trp Leu Ala Phe Gly His Ile Leu Pro Phe Leu Gln Leu Ser Lys Leu
        35                  40                  45

Ile Ala Glu Lys Gly His Lys Val Ser Phe Leu Ser Thr Thr Arg Asn
    50                  55                  60

Ile Gln Arg Leu Ser Ser His Ile Ser Pro Leu Ile Asn Val Val Gln
65                  70                  75                  80
```

```
Leu Thr Leu Pro Arg Val Gln Glu Leu Pro Glu Asp Ala Glu Ala Thr
             85                  90                  95

Thr Asp Val His Pro Glu Asp Ile Pro Tyr Leu Lys Lys Ala Ser Asp
            100                 105                 110

Gly Leu Gln Pro Glu Val Thr Arg Phe Leu Glu Gln His Ser Pro Asp
            115                 120                 125

Trp Ile Ile Tyr Asp Tyr Thr His Tyr Trp Leu Pro Ser Ile Ala Ala
            130                 135                 140

Ser Leu Gly Ile Ser Arg Ala His Phe Ser Val Val Thr Pro Trp Ala
145                 150                 155                 160

Ile Ala Tyr Met Gly Pro Ser Ala Asp Ala Met Ile Asn Gly Ser Asp
                165                 170                 175

Gly Arg Thr Thr Val Glu Asp Leu Thr Thr Pro Pro Lys Trp Phe Pro
                180                 185                 190

Phe Pro Thr Lys Val Cys Trp Arg Lys His Asp Leu Ala Arg Leu Val
            195                 200                 205

Pro Tyr Lys Ala Pro Gly Ile Ser Asp Gly Tyr Arg Met Gly Leu Val
            210                 215                 220

Leu Lys Gly Ser Asp Cys Leu Leu Phe Lys Cys Tyr His Glu Phe Gly
225                 230                 235                 240

Thr Gln Trp Leu Pro Leu Leu Glu Thr Leu His Gln Val Pro Val Val
                245                 250                 255

Pro Val Gly Leu Leu Pro Pro Glu Ile Pro Gly Asp Glu Lys Asp Glu
                260                 265                 270

Thr Trp Val Ser Ile Lys Lys Trp Leu Asp Gly Lys Gln Lys Gly Ser
            275                 280                 285

Val Val Tyr Val Ala Leu Gly Ser Glu Ala Leu Val Ser Gln Thr Glu
            290                 295                 300

Val Val Glu Leu Ala Leu Gly Leu Glu Leu Ser Gly Leu Pro Phe Val
305                 310                 315                 320

Trp Ala Tyr Arg Lys Pro Lys Gly Pro Ala Lys Ser Asp Ser Val Glu
                325                 330                 335

Leu Pro Asp Gly Phe Val Glu Arg Thr Arg Asp Arg Gly Leu Val Trp
                340                 345                 350

Thr Ser Trp Ala Pro Gln Leu Arg Ile Leu Ser His Glu Ser Val Cys
            355                 360                 365

Gly Phe Leu Thr His Cys Gly Ser Gly Ser Ile Val Glu Gly Leu Met
            370                 375                 380

Phe Gly His Pro Leu Ile Met Leu Pro Leu Phe Gly Asp Gln Pro Leu
385                 390                 395                 400

Asn Ala Arg Leu Leu Glu Asp Lys Gln Val Gly Ile Glu Ile Pro Arg
                405                 410                 415

Asn Glu Glu Asp Gly Cys Leu Thr Lys Glu Ser Val Ala Arg Ser Leu
            420                 425                 430

Arg Ser Val Val Val Glu Asn Glu Gly Glu Ile Tyr Lys Ala Asn Ala
            435                 440                 445

Arg Glu Leu Ser Lys Ile Tyr Asn Asp Thr Lys Val Glu Lys Glu Tyr
450                 455                 460

Val Ser Gln Phe Val Asp Phe Leu Glu Lys Asn Ala Arg Ala Val Ala
465                 470                 475                 480

Ile Asp His Glu Ser
            485
```

```
<210> SEQ ID NO 15
<211> LENGTH: 1446
<212> TYPE: DNA
<213> ORGANISM: Stevia rebaudiana
<220> FEATURE:
<221> NAME/KEY: CDS
<222> LOCATION: (1)..(1446)

<400> SEQUENCE: 15
```

| | | | | | | | | | | | | | | | | |
|---|---|---|---|---|---|---|---|---|---|---|---|---|---|---|---|---|
| atg | gat | gca | atg | gct | aca | act | gag | aag | aaa | cca | cac | gtc | atc | ttc | ata | 48 |
| Met | Asp | Ala | Met | Ala | Thr | Thr | Glu | Lys | Lys | Pro | His | Val | Ile | Phe | Ile | |
| 1 | | | | 5 | | | | | 10 | | | | | 15 | | |
| cca | ttt | cca | gca | caa | agc | cac | att | aaa | gcc | atg | ctc | aaa | cta | gca | caa | 96 |
| Pro | Phe | Pro | Ala | Gln | Ser | His | Ile | Lys | Ala | Met | Leu | Lys | Leu | Ala | Gln | |
| | | | 20 | | | | | 25 | | | | | 30 | | | |
| ctt | ctc | cac | cac | aaa | gga | ctc | cag | ata | acc | ttc | gtc | aac | acc | gac | ttc | 144 |
| Leu | Leu | His | His | Lys | Gly | Leu | Gln | Ile | Thr | Phe | Val | Asn | Thr | Asp | Phe | |
| | | | | 35 | | | | | 40 | | | | | 45 | | |
| atc | cac | aac | cag | ttt | ctt | gaa | tca | tcg | ggc | cca | cat | tgt | ttg | gac | ggt | 192 |
| Ile | His | Asn | Gln | Phe | Leu | Glu | Ser | Ser | Gly | Pro | His | Cys | Leu | Asp | Gly | |
| | | 50 | | | | | 55 | | | | | 60 | | | | |
| tca | ccg | ggt | ttc | cgg | ttc | gaa | acc | atc | ccg | gat | ggt | gtt | tct | cac | agt | 240 |
| Ser | Pro | Gly | Phe | Arg | Phe | Glu | Thr | Ile | Pro | Asp | Gly | Val | Ser | His | Ser | |
| 65 | | | | | 70 | | | | | 75 | | | | | 80 | |
| ccg | gaa | gcg | agc | atc | cca | atc | aga | gaa | tca | ctc | ctt | aga | tcc | att | gaa | 288 |
| Pro | Glu | Ala | Ser | Ile | Pro | Ile | Arg | Glu | Ser | Leu | Leu | Arg | Ser | Ile | Glu | |
| | | | | 85 | | | | | 90 | | | | | 95 | | |
| acc | aac | ttc | ttg | gat | cgt | ttc | att | gat | ctt | gta | acc | aaa | ctt | ccg | gat | 336 |
| Thr | Asn | Phe | Leu | Asp | Arg | Phe | Ile | Asp | Leu | Val | Thr | Lys | Leu | Pro | Asp | |
| | | | 100 | | | | | 105 | | | | | 110 | | | |
| cct | ccg | act | tgt | att | atc | tca | gat | ggg | ttc | ttg | tcg | gtt | ttc | aca | att | 384 |
| Pro | Pro | Thr | Cys | Ile | Ile | Ser | Asp | Gly | Phe | Leu | Ser | Val | Phe | Thr | Ile | |
| | | 115 | | | | | 120 | | | | | 125 | | | | |
| gac | gct | gca | aaa | aag | ctt | gga | att | ccg | gtc | atg | atg | tat | tgg | aca | ctt | 432 |
| Asp | Ala | Ala | Lys | Lys | Leu | Gly | Ile | Pro | Val | Met | Met | Tyr | Trp | Thr | Leu | |
| | 130 | | | | | 135 | | | | | 140 | | | | | |
| gct | gcc | tgt | ggg | ttc | atg | ggt | ttt | tac | cat | att | cat | tct | ctc | att | gag | 480 |
| Ala | Ala | Cys | Gly | Phe | Met | Gly | Phe | Tyr | His | Ile | His | Ser | Leu | Ile | Glu | |
| 145 | | | | | 150 | | | | | 155 | | | | | 160 | |
| aaa | gga | ttt | gca | cca | ctt | aaa | gat | gca | agt | tac | ttg | aca | aat | ggg | tat | 528 |
| Lys | Gly | Phe | Ala | Pro | Leu | Lys | Asp | Ala | Ser | Tyr | Leu | Thr | Asn | Gly | Tyr | |
| | | | | 165 | | | | | 170 | | | | | 175 | | |
| ttg | gac | acc | gtc | att | gat | tgg | gtt | ccg | gga | atg | gaa | ggc | atc | cgt | ctc | 576 |
| Leu | Asp | Thr | Val | Ile | Asp | Trp | Val | Pro | Gly | Met | Glu | Gly | Ile | Arg | Leu | |
| | | | 180 | | | | | 185 | | | | | 190 | | | |
| aag | gat | ttc | ccg | ctg | gac | tgg | agc | act | gac | ctc | aat | gac | aaa | gtt | ttg | 624 |
| Lys | Asp | Phe | Pro | Leu | Asp | Trp | Ser | Thr | Asp | Leu | Asn | Asp | Lys | Val | Leu | |
| | | 195 | | | | | 200 | | | | | 205 | | | | |
| atg | ttc | act | aca | gaa | gct | cct | caa | agg | tca | cac | aag | gtt | tca | cat | cat | 672 |
| Met | Phe | Thr | Thr | Glu | Ala | Pro | Gln | Arg | Ser | His | Lys | Val | Ser | His | His | |
| | 210 | | | | | 215 | | | | | 220 | | | | | |
| att | ttc | cac | acg | ttc | gat | gag | ttg | gag | cct | agt | att | ata | aaa | act | ttg | 720 |
| Ile | Phe | His | Thr | Phe | Asp | Glu | Leu | Glu | Pro | Ser | Ile | Ile | Lys | Thr | Leu | |
| 225 | | | | | 230 | | | | | 235 | | | | | 240 | |
| tca | ttg | agg | tat | aat | cac | att | tac | acc | atc | ggc | cca | ctg | caa | tta | ctt | 768 |
| Ser | Leu | Arg | Tyr | Asn | His | Ile | Tyr | Thr | Ile | Gly | Pro | Leu | Gln | Leu | Leu | |
| | | | | 245 | | | | | 250 | | | | | 255 | | |
| ctt | gat | caa | ata | ccc | gaa | gag | aaa | aag | caa | act | gga | att | acg | agt | ctc | 816 |
| Leu | Asp | Gln | Ile | Pro | Glu | Glu | Lys | Lys | Gln | Thr | Gly | Ile | Thr | Ser | Leu | |
| | | | 260 | | | | | 265 | | | | | 270 | | | |

| | | |
|---|---|---|
| cat gga tac agt tta gta aaa gaa gaa cca gag tgt ttc cag tgg ctt<br>His Gly Tyr Ser Leu Val Lys Glu Glu Pro Glu Cys Phe Gln Trp Leu<br>275                    280                  285 | | 864 |
| cag tct aaa gaa cca aat tcc gtc gtt tat gta aat ttt gga agt act<br>Gln Ser Lys Glu Pro Asn Ser Val Val Tyr Val Asn Phe Gly Ser Thr<br>290                   295                  300 | | 912 |
| aca gta atg tct tta gaa gac atg acg gaa ttt ggt tgg gga ctt gct<br>Thr Val Met Ser Leu Glu Asp Met Thr Glu Phe Gly Trp Gly Leu Ala<br>305                    310                  315                 320 | | 960 |
| aat agc aac cat tat ttc ctt tgg atc atc cga tca aac ttg gtg ata<br>Asn Ser Asn His Tyr Phe Leu Trp Ile Ile Arg Ser Asn Leu Val Ile<br>                           325                  330                  335 | | 1008 |
| ggg gaa aat gca gtt ttg ccc cct gaa ctt gag gaa cat ata aag aaa<br>Gly Glu Asn Ala Val Leu Pro Pro Glu Leu Glu Glu His Ile Lys Lys<br>                 340                  345                  350 | | 1056 |
| aga ggc ttt att gct agc tgg tgt tca caa gaa aag gtc ttg aag cac<br>Arg Gly Phe Ile Ala Ser Trp Cys Ser Gln Glu Lys Val Leu Lys His<br>                           355                  360                  365 | | 1104 |
| cct tcg gtt gga ggg ttc ttg act cat tgt ggg tgg gga tcg acc atc<br>Pro Ser Val Gly Gly Phe Leu Thr His Cys Gly Trp Gly Ser Thr Ile<br>370                    375                  380 | | 1152 |
| gag agc ttg tct gct ggg gtg cca atg ata tgc tgg cct tat tcg tgg<br>Glu Ser Leu Ser Ala Gly Val Pro Met Ile Cys Trp Pro Tyr Ser Trp<br>385                    390                  395                 400 | | 1200 |
| gac cag ctg acc aac tgt agg tat ata tgc aaa gaa tgg gag gtt ggg<br>Asp Gln Leu Thr Asn Cys Arg Tyr Ile Cys Lys Glu Trp Glu Val Gly<br>                           405                  410                  415 | | 1248 |
| ctc gag atg gga acc aaa gtg aaa cga gat gaa gtc aag agg ctt gta<br>Leu Glu Met Gly Thr Lys Val Lys Arg Asp Glu Val Lys Arg Leu Val<br>                 420                  425                  430 | | 1296 |
| caa gag ttg atg gga gaa gga ggt cac aaa atg agg aac aag gct aaa<br>Gln Glu Leu Met Gly Glu Gly Gly His Lys Met Arg Asn Lys Ala Lys<br>                           435                  440                  445 | | 1344 |
| gat tgg aaa gaa aag gct cgc att gca ata gct cct aac ggt tca tct<br>Asp Trp Lys Glu Lys Ala Arg Ile Ala Ile Ala Pro Asn Gly Ser Ser<br>450                    455                  460 | | 1392 |
| tct ttg aac ata gac aaa atg gtc aag gaa atc acc gtg cta gca aga<br>Ser Leu Asn Ile Asp Lys Met Val Lys Glu Ile Thr Val Leu Ala Arg<br>465                    470                  475                 480 | | 1440 |
| aac tag<br>Asn | | 1446 |

<210> SEQ ID NO 16
<211> LENGTH: 481
<212> TYPE: PRT
<213> ORGANISM: Stevia rebaudiana

<400> SEQUENCE: 16

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ser Pro Gly Phe Arg Phe Glu Thr Ile Pro Asp Gly Val Ser His Ser
65                  70                  75                  80

-continued

```
Pro Glu Ala Ser Ile Pro Ile Arg Glu Ser Leu Leu Arg Ser Ile Glu
                 85                  90                  95
Thr Asn Phe Leu Asp Arg Phe Ile Asp Leu Val Thr Lys Leu Pro Asp
            100                 105                 110
Pro Pro Thr Cys Ile Ile Ser Asp Gly Phe Leu Ser Val Phe Thr Ile
            115                 120                 125
Asp Ala Ala Lys Lys Leu Gly Ile Pro Val Met Met Tyr Trp Thr Leu
130                 135                 140
Ala Ala Cys Gly Phe Met Gly Phe Tyr His Ile His Ser Leu Ile Glu
145                 150                 155                 160
Lys Gly Phe Ala Pro Leu Lys Asp Ala Ser Tyr Leu Thr Asn Gly Tyr
                165                 170                 175
Leu Asp Thr Val Ile Asp Trp Val Pro Gly Met Glu Gly Ile Arg Leu
            180                 185                 190
Lys Asp Phe Pro Leu Asp Trp Ser Thr Asp Leu Asn Asp Lys Val Leu
            195                 200                 205
Met Phe Thr Thr Glu Ala Pro Gln Arg Ser His Lys Val Ser His His
210                 215                 220
Ile Phe His Thr Phe Asp Glu Leu Glu Pro Ser Ile Ile Lys Thr Leu
225                 230                 235                 240
Ser Leu Arg Tyr Asn His Ile Tyr Thr Ile Gly Pro Leu Gln Leu Leu
                245                 250                 255
Leu Asp Gln Ile Pro Glu Glu Lys Lys Gln Thr Gly Ile Thr Ser Leu
            260                 265                 270
His Gly Tyr Ser Leu Val Lys Glu Glu Pro Glu Cys Phe Gln Trp Leu
            275                 280                 285
Gln Ser Lys Glu Pro Asn Ser Val Val Tyr Val Asn Phe Gly Ser Thr
290                 295                 300
Thr Val Met Ser Leu Glu Asp Met Thr Glu Phe Gly Trp Gly Leu Ala
305                 310                 315                 320
Asn Ser Asn His Tyr Phe Leu Trp Ile Ile Arg Ser Asn Leu Val Ile
                325                 330                 335
Gly Glu Asn Ala Val Leu Pro Pro Glu Leu Glu Glu His Ile Lys Lys
            340                 345                 350
Arg Gly Phe Ile Ala Ser Trp Cys Ser Gln Glu Lys Val Leu Lys His
            355                 360                 365
Pro Ser Val Gly Gly Phe Leu Thr His Cys Gly Trp Gly Ser Thr Ile
370                 375                 380
Glu Ser Leu Ser Ala Gly Val Pro Met Ile Cys Trp Pro Tyr Ser Trp
385                 390                 395                 400
Asp Gln Leu Thr Asn Cys Arg Tyr Ile Cys Lys Glu Trp Glu Val Gly
                405                 410                 415
Leu Glu Met Gly Thr Lys Val Lys Arg Asp Glu Val Lys Arg Leu Val
            420                 425                 430
Gln Glu Leu Met Gly Glu Gly His Lys Met Arg Asn Lys Ala Lys
            435                 440                 445
Asp Trp Lys Glu Lys Ala Arg Ile Ala Ile Ala Pro Asn Gly Ser Ser
            450                 455                 460
Ser Leu Asn Ile Asp Lys Met Val Lys Glu Ile Thr Val Leu Ala Arg
465                 470                 475                 480
Asn
```

```
<210> SEQ ID NO 17
<211> LENGTH: 1383
<212> TYPE: DNA
<213> ORGANISM: Stevia rebaudiana
<220> FEATURE:
<221> NAME/KEY: CDS
<222> LOCATION: (1)..(1383)

<400> SEQUENCE: 17
```

| | | | | | | | | | | | | | | | | |
|---|---|---|---|---|---|---|---|---|---|---|---|---|---|---|---|---|
| atg | gcg | gaa | caa | caa | aag | atc | aag | aaa | tca | cca | cac | gtt | cta | ctc | atc | 48 |
| Met | Ala | Glu | Gln | Gln | Lys | Ile | Lys | Lys | Ser | Pro | His | Val | Leu | Leu | Ile | |
| 1 | | | | 5 | | | | | 10 | | | | | 15 | | |
| cca | ttc | cct | tta | caa | ggc | cat | ata | aac | cct | ttc | atc | cag | ttt | ggc | aaa | 96 |
| Pro | Phe | Pro | Leu | Gln | Gly | His | Ile | Asn | Pro | Phe | Ile | Gln | Phe | Gly | Lys | |
| | | | 20 | | | | | 25 | | | | | 30 | | | |
| cga | tta | atc | tcc | aaa | ggt | gtc | aaa | aca | aca | ctt | gtt | acc | acc | atc | cac | 144 |
| Arg | Leu | Ile | Ser | Lys | Gly | Val | Lys | Thr | Thr | Leu | Val | Thr | Thr | Ile | His | |
| | | 35 | | | | | 40 | | | | | 45 | | | | |
| acc | tta | aac | tca | acc | cta | aac | cac | agt | aac | acc | acc | acc | tcc | atc | | 192 |
| Thr | Leu | Asn | Ser | Thr | Leu | Asn | His | Ser | Asn | Thr | Thr | Thr | Ser | Ile | | |
| | 50 | | | | | 55 | | | | | 60 | | | | | |
| gaa | atc | caa | gca | att | tcc | gat | ggt | tgt | gat | gaa | ggc | ggt | ttt | atg | agt | 240 |
| Glu | Ile | Gln | Ala | Ile | Ser | Asp | Gly | Cys | Asp | Glu | Gly | Gly | Phe | Met | Ser | |
| 65 | | | | | 70 | | | | | 75 | | | | | 80 | |
| gca | gga | gaa | tca | tat | ttg | gaa | aca | ttc | aaa | caa | gtt | ggg | tct | aaa | tca | 288 |
| Ala | Gly | Glu | Ser | Tyr | Leu | Glu | Thr | Phe | Lys | Gln | Val | Gly | Ser | Lys | Ser | |
| | | | | 85 | | | | | 90 | | | | | 95 | | |
| cta | gct | gac | tta | atc | aag | aag | ctt | caa | agt | gaa | gga | acc | aca | att | gat | 336 |
| Leu | Ala | Asp | Leu | Ile | Lys | Lys | Leu | Gln | Ser | Glu | Gly | Thr | Thr | Ile | Asp | |
| | | | 100 | | | | | 105 | | | | | 110 | | | |
| gca | atc | att | tat | gat | tct | atg | act | gaa | tgg | gtt | tta | gat | gtt | gca | att | 384 |
| Ala | Ile | Ile | Tyr | Asp | Ser | Met | Thr | Glu | Trp | Val | Leu | Asp | Val | Ala | Ile | |
| | | 115 | | | | | 120 | | | | | 125 | | | | |
| gag | ttt | gga | atc | gat | ggt | ggt | tcg | ttt | ttc | act | caa | gct | tgt | gtt | gta | 432 |
| Glu | Phe | Gly | Ile | Asp | Gly | Gly | Ser | Phe | Phe | Thr | Gln | Ala | Cys | Val | Val | |
| | 130 | | | | | 135 | | | | | 140 | | | | | |
| aac | agc | tta | tat | tat | cat | gtt | cat | aag | ggt | ttg | att | tct | ttg | cca | ttg | 480 |
| Asn | Ser | Leu | Tyr | Tyr | His | Val | His | Lys | Gly | Leu | Ile | Ser | Leu | Pro | Leu | |
| 145 | | | | | 150 | | | | | 155 | | | | | 160 | |
| ggt | gaa | act | gtt | tcg | gtt | cct | gga | ttt | cca | gag | ctt | caa | cgg | tgg | gag | 528 |
| Gly | Glu | Thr | Val | Ser | Val | Pro | Gly | Phe | Pro | Glu | Leu | Gln | Arg | Trp | Glu | |
| | | | | 165 | | | | | 170 | | | | | 175 | | |
| aca | ccg | tta | att | ttg | cag | aat | cat | gag | caa | ata | cag | agc | cct | tgg | tct | 576 |
| Thr | Pro | Leu | Ile | Leu | Gln | Asn | His | Glu | Gln | Ile | Gln | Ser | Pro | Trp | Ser | |
| | | | 180 | | | | | 185 | | | | | 190 | | | |
| cag | atg | ttg | ttt | ggt | cag | ttt | gct | aat | att | gat | caa | gca | cgt | tgg | gtc | 624 |
| Gln | Met | Leu | Phe | Gly | Gln | Phe | Ala | Asn | Ile | Asp | Gln | Ala | Arg | Trp | Val | |
| | | 195 | | | | | 200 | | | | | 205 | | | | |
| ttc | aca | aat | agt | ttt | tac | aag | ctc | gag | gaa | gag | gta | ata | gag | tgg | acg | 672 |
| Phe | Thr | Asn | Ser | Phe | Tyr | Lys | Leu | Glu | Glu | Glu | Val | Ile | Glu | Trp | Thr | |
| | 210 | | | | | 215 | | | | | 220 | | | | | |
| aga | aag | ata | tgg | aac | ttg | aag | gta | atc | ggg | cca | aca | ctt | cca | tcc | atg | 720 |
| Arg | Lys | Ile | Trp | Asn | Leu | Lys | Val | Ile | Gly | Pro | Thr | Leu | Pro | Ser | Met | |
| 225 | | | | | 230 | | | | | 235 | | | | | 240 | |
| tac | ctt | gac | aaa | cga | ctt | gat | gat | gat | aaa | gat | aac | gga | ttt | aat | ctc | 768 |
| Tyr | Leu | Asp | Lys | Arg | Leu | Asp | Asp | Asp | Lys | Asp | Asn | Gly | Phe | Asn | Leu | |
| | | | | 245 | | | | | 250 | | | | | 255 | | |
| tac | aaa | gca | aac | cat | cat | gag | tgc | atg | aac | tgg | tta | gac | gat | aag | cca | 816 |
| Tyr | Lys | Ala | Asn | His | His | Glu | Cys | Met | Asn | Trp | Leu | Asp | Asp | Lys | Pro | |
| | | | 260 | | | | | 265 | | | | | 270 | | | |

-continued

| | | |
|---|---|---|
| aag gaa tca gtt gtt tac gta gca ttt ggt agc ctg gtg aaa cat gga<br>Lys Glu Ser Val Val Tyr Val Ala Phe Gly Ser Leu Val Lys His Gly<br>275 280 285 | 864 | |
| ccc gaa caa gtg gaa gaa atc aca cgg gct tta ata gat agt gat gtc<br>Pro Glu Gln Val Glu Glu Ile Thr Arg Ala Leu Ile Asp Ser Asp Val<br>290 295 300 | 912 | |
| aac ttc ttg tgg gtt atc aaa cat aaa gaa gag gga aag ctc cca gaa<br>Asn Phe Leu Trp Val Ile Lys His Lys Glu Glu Gly Lys Leu Pro Glu<br>305 310 315 320 | 960 | |
| aat ctt tcg gaa gta ata aaa acc gga aag ggt ttg att gta gca tgg<br>Asn Leu Ser Glu Val Ile Lys Thr Gly Lys Gly Leu Ile Val Ala Trp<br>325 330 335 | 1008 | |
| tgc aaa caa ttg gat gtg tta gca cac gaa tca gta gga tgc ttt gtt<br>Cys Lys Gln Leu Asp Val Leu Ala His Glu Ser Val Gly Cys Phe Val<br>340 345 350 | 1056 | |
| aca cat tgt ggg ttc aac tca act ctt gaa gca ata agt ctt gga gtc<br>Thr His Cys Gly Phe Asn Ser Thr Leu Glu Ala Ile Ser Leu Gly Val<br>355 360 365 | 1104 | |
| ccc gtt gtt gca atg cct caa ttt tcg gat caa act aca aat gcc aag<br>Pro Val Val Ala Met Pro Gln Phe Ser Asp Gln Thr Thr Asn Ala Lys<br>370 375 380 | 1152 | |
| ctt cta gat gaa att ttg ggt gtt gga gtt aga gtt aag gct gat gag<br>Leu Leu Asp Glu Ile Leu Gly Val Gly Val Arg Val Lys Ala Asp Glu<br>385 390 395 400 | 1200 | |
| aat ggg ata gtg aga aga gga aat ctt gcg tca tgt att aag atg att<br>Asn Gly Ile Val Arg Arg Gly Asn Leu Ala Ser Cys Ile Lys Met Ile<br>405 410 415 | 1248 | |
| atg gag gag gaa aga gga gta ata atc cga aag aat gcg gta aaa tgg<br>Met Glu Glu Glu Arg Gly Val Ile Ile Arg Lys Asn Ala Val Lys Trp<br>420 425 430 | 1296 | |
| aag gat ttg gct aaa gta gcc gtt cat gaa ggt ggt agc tca gac aat<br>Lys Asp Leu Ala Lys Val Ala Val His Glu Gly Gly Ser Ser Asp Asn<br>435 440 445 | 1344 | |
| gat att gtc gaa ttt gta agt gag cta att aag gct taa<br>Asp Ile Val Glu Phe Val Ser Glu Leu Ile Lys Ala<br>450 455 460 | 1383 | |

<210> SEQ ID NO 18
<211> LENGTH: 460
<212> TYPE: PRT
<213> ORGANISM: Stevia rebaudiana

<400> SEQUENCE: 18

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Ser Ile
    50                  55                  60

Glu Ile Gln Ala Ile Ser Asp Gly Cys Asp Glu Gly Phe Met Ser
65              70                  75                  80

Ala Gly Glu Ser Tyr Leu Glu Thr Phe Lys Gln Val Gly Ser Lys Ser
            85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

```
Glu Phe Gly Ile Asp Gly Gly Ser Phe Phe Thr Gln Ala Cys Val Val
    130             135                 140

Asn Ser Leu Tyr Tyr His Val His Lys Gly Leu Ile Ser Leu Pro Leu
145             150                 155                 160

Gly Glu Thr Val Ser Val Pro Gly Phe Pro Glu Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
210             215                 220

Arg Lys Ile Trp Asn Leu Lys Val Ile Gly Pro Thr Leu Pro Ser Met
225             230                 235                 240

Tyr Leu Asp Lys Arg Leu Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Gly Lys Leu Pro Glu
305             310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
    370                 375                 380

Leu Leu Asp Glu Ile Leu Gly Val Gly Val Arg Val Lys Ala Asp Glu
385             390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
        435                 440                 445

Asp Ile Val Glu Phe Val Ser Glu Leu Ile Lys Ala
    450                 455                 460

<210> SEQ ID NO 19
<211> LENGTH: 1377
<212> TYPE: DNA
<213> ORGANISM: Stevia rebaudiana
<220> FEATURE:
<221> NAME/KEY: CDS
<222> LOCATION: (1)..(1377)

<400> SEQUENCE: 19 atg gaa aat aaa acg gag acc acc gtt cgc cgg cgc cgg aga ata ata    48
Met Glu Asn Lys Thr Glu Thr Thr Val Arg Arg Arg Arg Ile Ile
1               5                   10                  15
```

-continued

| | | |
|---|---|---|
| tta ttc ccg gta cca ttt caa ggc cac att aac cca att ctt cag cta<br>Leu Phe Pro Val Pro Phe Gln Gly His Ile Asn Pro Ile Leu Gln Leu<br>              20                        25                30 | 96 |
| gcc aat gtg ttg tac tct aaa gga ttc agt atc acc atc ttt cac acc<br>Ala Asn Val Leu Tyr Ser Lys Gly Phe Ser Ile Thr Ile Phe His Thr<br>         35                    40                      45 | 144 |
| aac ttc aac aaa ccc aaa aca tct aat tac cct cac ttc act ttc aga<br>Asn Phe Asn Lys Pro Lys Thr Ser Asn Tyr Pro His Phe Thr Phe Arg<br>50                        55                      60 | 192 |
| ttc atc ctc gac aac gac cca caa gac gaa cgc att tcc aat cta ccg<br>Phe Ile Leu Asp Asn Asp Pro Gln Asp Glu Arg Ile Ser Asn Leu Pro<br>65                        70                      75                      80 | 240 |
| act cat ggt ccg ctc gct ggt atg cgg att ccg att atc aac gaa cac<br>Thr His Gly Pro Leu Ala Gly Met Arg Ile Pro Ile Ile Asn Glu His<br>              85                        90                      95 | 288 |
| gga gct gac gaa tta cga cgc gaa ctg gaa ctg ttg atg tta gct tct<br>Gly Ala Asp Glu Leu Arg Arg Glu Leu Glu Leu Leu Met Leu Ala Ser<br>              100                      105                     110 | 336 |
| gaa gaa gat gaa gag gta tcg tgt tta atc acg gat gct ctt tgg tac<br>Glu Glu Asp Glu Glu Val Ser Cys Leu Ile Thr Asp Ala Leu Trp Tyr<br>          115                     120                     125 | 384 |
| ttc gcg caa tct gtt gct gac agt ctt aac ctc cga ccg ctt gtt ttg<br>Phe Ala Gln Ser Val Ala Asp Ser Leu Asn Leu Arg Pro Leu Val Leu<br>130                        135                     140 | 432 |
| atg aca agc agc ttg ttt aat ttt cat gca cat gtt tca ctt cct cag<br>Met Thr Ser Ser Leu Phe Asn Phe His Ala His Val Ser Leu Pro Gln<br>145                        150                     155                     160 | 480 |
| ttt gat gag ctt ggt tac ctc gat cct gat gac aaa acc cgt ttg gaa<br>Phe Asp Glu Leu Gly Tyr Leu Asp Pro Asp Asp Lys Thr Arg Leu Glu<br>              165                     170                     175 | 528 |
| gaa caa gcg agt ggg ttt cct atg cta aaa gtg aaa gac atc aag tct<br>Glu Gln Ala Ser Gly Phe Pro Met Leu Lys Val Lys Asp Ile Lys Ser<br>                  180                     185                     190 | 576 |
| gcg tat tcg aac tgg caa ata ctc aaa gag ata tta ggg aag atg ata<br>Ala Tyr Ser Asn Trp Gln Ile Leu Lys Glu Ile Leu Gly Lys Met Ile<br>         195                     200                     205 | 624 |
| aaa caa aca aaa gca tct tca gga gtc atc tgg aac tca ttt aag gaa<br>Lys Gln Thr Lys Ala Ser Ser Gly Val Ile Trp Asn Ser Phe Lys Glu<br>210                        215                     220 | 672 |
| ctc gaa gag tct gag ctc gaa act gtt atc cgt gag atc ccg gct cca<br>Leu Glu Glu Ser Glu Leu Glu Thr Val Ile Arg Glu Ile Pro Ala Pro<br>225                        230                     235                     240 | 720 |
| agt ttc ttg ata cca ctc ccc aag cat ttg aca gcc tct tcc agc agc<br>Ser Phe Leu Ile Pro Leu Pro Lys His Leu Thr Ala Ser Ser Ser Ser<br>                    245                     250                     255 | 768 |
| tta cta gac cac gat cga acc gtt ttt caa tgg tta gac caa caa ccg<br>Leu Leu Asp His Asp Arg Thr Val Phe Gln Trp Leu Asp Gln Gln Pro<br>                  260                     265                     270 | 816 |
| cca agt tcg gta ctg tat gtt agt ttt ggt agt act agt gaa gtg gat<br>Pro Ser Ser Val Leu Tyr Val Ser Phe Gly Ser Thr Ser Glu Val Asp<br>         275                     280                     285 | 864 |
| gag aaa gat ttc ttg gaa ata gct cgt ggg ttg gtt gat agc aag cag<br>Glu Lys Asp Phe Leu Glu Ile Ala Arg Gly Leu Val Asp Ser Lys Gln<br>290                        295                     300 | 912 |
| tcg ttt tta tgg gtg gtt cga cct ggg ttt gtc aag ggt tcg acg tgg<br>Ser Phe Leu Trp Val Val Arg Pro Gly Phe Val Lys Gly Ser Thr Trp<br>305                        310                     315                     320 | 960 |
| gtc gaa ccg ttg cca gat ggg ttc ttg ggt gaa aga gga cgt att gtg<br>Val Glu Pro Leu Pro Asp Gly Phe Leu Gly Glu Arg Gly Arg Ile Val<br>                  325                     330                     335 | 1008 |

```
aaa tgg gtt cca cag caa gaa gtg cta gct cat gga gca ata ggc gca    1056
Lys Trp Val Pro Gln Gln Glu Val Leu Ala His Gly Ala Ile Gly Ala
            340                 345                 350 ttc tgg act cat agc gga tgg aac tct acg ttg gaa agc gtt tgt gaa    1104
Phe Trp Thr His Ser Gly Trp Asn Ser Thr Leu Glu Ser Val Cys Glu
            355                 360                 365 ggt gtt cct atg att ttc tcg gat ttt ggg ctc gat caa ccg ttg aat    1152
Gly Val Pro Met Ile Phe Ser Asp Phe Gly Leu Asp Gln Pro Leu Asn
            370                 375                 380 gct aga tac atg agt gat gtt ttg aag gta ggg gtg tat ttg gaa aat    1200
Ala Arg Tyr Met Ser Asp Val Leu Lys Val Gly Val Tyr Leu Glu Asn
385                 390                 395                 400 ggg tgg gaa aga gga gag ata gca aat gca ata aga aga gtt atg gtg    1248
Gly Trp Glu Arg Gly Glu Ile Ala Asn Ala Ile Arg Arg Val Met Val
                405                 410                 415 gat gaa gaa gga gaa tac att aga cag aat gca aga gtt ttg aaa caa    1296
Asp Glu Glu Gly Glu Tyr Ile Arg Gln Asn Ala Arg Val Leu Lys Gln
            420                 425                 430 aag gca gat gtt tct ttg atg aag ggt ggt tcg tct tac gaa tca tta    1344
Lys Ala Asp Val Ser Leu Met Lys Gly Gly Ser Ser Tyr Glu Ser Leu
                435                 440                 445 gag tct cta gtt tct tac att tca tcg ttg taa                        1377
Glu Ser Leu Val Ser Tyr Ile Ser Ser Leu
        450                 455

<210> SEQ ID NO 20
<211> LENGTH: 458
<212> TYPE: PRT
<213> ORGANISM: Stevia rebaudiana

<400> SEQUENCE: 20

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Pro Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205
```

Lys Gln Thr Lys Ala Ser Ser Gly Val Ile Trp Asn Ser Phe Lys Glu
210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
            245                 250                 255

Leu Leu Asp His Asp Arg Thr Val Phe Gln Trp Leu Asp Gln Gln Pro
        260                 265                 270

Pro Ser Ser Val Leu Tyr Val Ser Phe Gly Ser Thr Ser Glu Val Asp
    275                 280                 285

Glu Lys Asp Phe Leu Glu Ile Ala Arg Gly Leu Val Asp Ser Lys Gln
290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 21
<211> LENGTH: 2004
<212> TYPE: DNA
<213> ORGANISM: Arabidopsis thaliana

<400> SEQUENCE: 21
atggatgata ctacgtataa gccaagaac attctcatta ctggagctgc tggatttatt         60
gcttctcatg ttgccaacag attaatccgt aactatcctg attacaagat cgttgttctt        120
gacaagcttg attactgttc agatctgaag aatcttgatc cttctttttc ttcaccaaat        180
ttcaagtttg tcaaggaga tatcgcgagt gatgatctcg ttaactacct tctcatcact         240
gaaaacattg atacgataat gcattttgct gctcaaactc atgttgataa ctcttttggt        300
aatagctttg agtttaccaa gaacaatatt tatggtactc atgttctttt ggaagcctgt        360
aaagttacag gacagatcag gaggtttatc catgtgagta ccgatgaagt ctatggagaa        420
accgatgagg atgctgctgt aggaaaccat gaagcttctc agctgttacc gacgaatcct        480
tactctgcaa ctaaggctgg tgctgagatg cttgtgatgg cttatggtag atcatatgga        540
ttgcctgtta ttacgactcg cgggaacaat gtttatgggc taaccagtt tcctgaaaaa        600 atgattccta agttcatctt gttggctatg agtgggaagc cgcttcccat ccatggagat        660
ggatctaatg tccggagtta cttgtactgc gaagacgttg ctgaggcttt tgaggttgtt        720

```
cttcacaaag gagaaatcgg tcatgtctac aatgtcggca caaaaagaga aaggagagtg    780
atcgatgtgg ctagagacat ctgcaaactt ttcgggaaag accctgagtc aagcattcag    840
tttgtggaga accggccctt taatgatcaa aggtacttcc ttgatgatca gaagctgaag    900
aaattggggt ggcaagagcg aacaaattgg gaagatggat tgaagaagac aatggactgg    960
tacactcaga atcctgagtg gtggggtgat gtttctggag ctttgcttcc tcatccgaga   1020
atgcttatga tgcccggtgg aagactttct gatggatcta gtgagaagaa agacgtttca   1080
agcaacacgg tccagacatt tacggttgta acacctaaga atggtgattc tggtgacaaa   1140
gcttcgttga agttttgat ctatggtaag actggttggc ttggtggtct tctagggaaa   1200
ctatgtgaga agcaagggat tacatatgag tatgggaaag gacgtctgga ggatagagct   1260
tctcttgtgg cggatattcg tagcatcaaa cctactcatg tgtttaatgc tgctggttta   1320
actggcagac ccaacgttga ctggtgtgaa tctcacaaac cagagaccat tcgtgtaaat   1380
gtcgcaggta ctttgactct agctgatgtt tgcagagaga atgatctctt gatgatgaac   1440
ttcgccaccg gttgcatctt tgagtatgac gctacacatc ctgagggttc gggtataggt   1500
ttcaaggaag aagacaagcc aaatttcttt ggttctttct actcgaaaac caaagccatg   1560
gttgaggagc tcttgagaga atttgacaat gtatgtacct tgagagtccg gatgccaatc   1620
tcctcagacc taaacaaccc gagaaacttc atcacgaaga tctcgcgcta caacaaagtg   1680
gtggacatcc cgaacagcat gaccgtacta gacgagcttc tcccaatctc tatcgagatg   1740
gcgaagagaa acctaagagg catatggaat ttcaccaacc caggggtggt gagccacaac   1800
gagatattgg agatgtacaa gaattacatc gagccaggtt ttaaatggtc caacttcaca   1860
gtggaagaac aagcaaaggt cattgttgct gctcgaagca acaacgaaat ggatggatct   1920
aaactaagca aggagttccc agagatgctc tccatcaaag agtcactgct caaatacgtc   1980
tttgaaccaa acaagagaac ctaa                                          2004

<210> SEQ ID NO 22
<211> LENGTH: 38
<212> TYPE: DNA
<213> ORGANISM: Artificial
<220> FEATURE:
<223> OTHER INFORMATION: SrRHM1-pET-FW

<400> SEQUENCE: 22
tgccgcgcgg cagccatatg gctacttacg tgccaaag                              38

<210> SEQ ID NO 23
<211> LENGTH: 44
<212> TYPE: DNA
<213> ORGANISM: Artificial
<220> FEATURE:
<223> OTHER INFORMATION: SrRHM1-pET-RV

<400> SEQUENCE: 23
gttagcagcc ggatccttaa tgttttttgt taggttcgaa tacg                       44

<210> SEQ ID NO 24
<211> LENGTH: 41
<212> TYPE: DNA
<213> ORGANISM: Artificial
<220> FEATURE:
<223> OTHER INFORMATION: SrRHM2Full-Fw

<400> SEQUENCE: 24
tgccgcgcgg cagccatatg accagttata cacctaaaaa c                          41
```

-continued

```
<210> SEQ ID NO 25
<211> LENGTH: 43
<212> TYPE: DNA
<213> ORGANISM: Artificial
<220> FEATURE:
<223> OTHER INFORMATION: SrRHM2Full-Rv

<400> SEQUENCE: 25
gttagcagcc ggatccttag gttgtcttgt tgggtgcaaa tac            43

<210> SEQ ID NO 26
<211> LENGTH: 24
<212> TYPE: DNA
<213> ORGANISM: Artificial
<220> FEATURE:
<223> OTHER INFORMATION: SrACTIN-Fw

<400> SEQUENCE: 26
atggccgata ctgaggatat tcag                                  24

<210> SEQ ID NO 27
<211> LENGTH: 22
<212> TYPE: DNA
<213> ORGANISM: Artificial
<220> FEATURE:
<223> OTHER INFORMATION: SrACTIN-Rv

<400> SEQUENCE: 27
agcacttcct gtggacaatg ga                                    22

<210> SEQ ID NO 28
<211> LENGTH: 27
<212> TYPE: DNA
<213> ORGANISM: Artificial
<220> FEATURE:
<223> OTHER INFORMATION: Apa-SrRHM1-F

<400> SEQUENCE: 28
gggcccatgg ctacttacgt gccaaag                               27

<210> SEQ ID NO 29
<211> LENGTH: 34
<212> TYPE: DNA
<213> ORGANISM: Artificial
<220> FEATURE:
<223> OTHER INFORMATION: Xho-SrRHM1-R

<400> SEQUENCE: 29
ctcgagttaa tgttttttgt taggttcgaa tacg                       34

<210> SEQ ID NO 30
<211> LENGTH: 34
<212> TYPE: DNA
<213> ORGANISM: Artificial
<220> FEATURE:
<223> OTHER INFORMATION: Bam-SrRHM2-F

<400> SEQUENCE: 30
ggatccatga ccagttatac acctaaaaac atcc                       34

<210> SEQ ID NO 31
<211> LENGTH: 27
<212> TYPE: DNA
<213> ORGANISM: Artificial
<220> FEATURE:
<223> OTHER INFORMATION: Xho-SrRHM2-R
```

<400> SEQUENCE: 31
ctcgagttag gttgtcttgt tgggtgc       27

<210> SEQ ID NO 32
<211> LENGTH: 22
<212> TYPE: DNA
<213> ORGANISM: Artificial
<220> FEATURE:
<223> OTHER INFORMATION: SrRHM1-r1

<400> SEQUENCE: 32
cgagttaggt atttggacac ca       22

<210> SEQ ID NO 33
<211> LENGTH: 21
<212> TYPE: DNA
<213> ORGANISM: Artificial
<220> FEATURE:
<223> OTHER INFORMATION: SrRHM2-r1

<400> SEQUENCE: 33
taccgggtcc tgaaagatga c       21

<210> SEQ ID NO 34
<211> LENGTH: 28
<212> TYPE: DNA
<213> ORGANISM: Artificial
<220> FEATURE:
<223> OTHER INFORMATION: PGAL10-f3

<400> SEQUENCE: 34
gattattaaa cttctttgcg tccatcca       28

<210> SEQ ID NO 35
<211> LENGTH: 33
<212> TYPE: DNA
<213> ORGANISM: Artificial
<220> FEATURE:
<223> OTHER INFORMATION: CACC-NdeI-SrUGT85C2-Fw

<400> SEQUENCE: 35
cacccatatg gatgcaatgg ctacaactga gaa       33

<210> SEQ ID NO 36
<211> LENGTH: 32
<212> TYPE: DNA
<213> ORGANISM: Artificial
<220> FEATURE:
<223> OTHER INFORMATION: BglII-SrUGT85C2-Rv

<400> SEQUENCE: 36
agatctctag tttcttgcta gcacggtgat tt       32

<210> SEQ ID NO 37
<211> LENGTH: 39
<212> TYPE: DNA
<213> ORGANISM: Artificial
<220> FEATURE:
<223> OTHER INFORMATION: SrUGT91D2-pET15b-FW

<400> SEQUENCE: 37
tgccgcgcgg cagccatatg tacaacgtta cttatcatc       39

```
<210> SEQ ID NO 38
<211> LENGTH: 39
<212> TYPE: DNA
<213> ORGANISM: Artificial
<220> FEATURE:
<223> OTHER INFORMATION: SrUGT91D2-pET15b-RV

<400> SEQUENCE: 38
gttagcagcc ggatccttaa ctctcatgat cgatggcaa                              39

<210> SEQ ID NO 39
<211> LENGTH: 35
<212> TYPE: DNA
<213> ORGANISM: Artificial
<220> FEATURE:
<223> OTHER INFORMATION: CACC-NdeI-SrUGT74G1-Fw

<400> SEQUENCE: 39
cacccatatg gcggaacaac aaaagatcaa gaaat                                  35

<210> SEQ ID NO 40
<211> LENGTH: 35
<212> TYPE: DNA
<213> ORGANISM: Artificial
<220> FEATURE:
<223> OTHER INFORMATION: BamHI-SrUGT74G1-Rv

<400> SEQUENCE: 40
ggatccttaa gccttaatta gctcacttac aaatt                                  35

<210> SEQ ID NO 41
<211> LENGTH: 29
<212> TYPE: DNA
<213> ORGANISM: Artificial
<220> FEATURE:
<223> OTHER INFORMATION: CACC-NdeI-SrUGT76G1-Fw

<400> SEQUENCE: 41
cacccatatg gaaaataaaa cggagacca                                         29

<210> SEQ ID NO 42
<211> LENGTH: 32
<212> TYPE: DNA
<213> ORGANISM: Artificial
<220> FEATURE:
<223> OTHER INFORMATION: BamHI-SrUGT76G1-Rv

<400> SEQUENCE: 42
ggatccttac aacgatgaaa tgtaagaaac ta                                     32

<210> SEQ ID NO 43
<211> LENGTH: 33
<212> TYPE: DNA
<213> ORGANISM: Artificial
<220> FEATURE:
<223> OTHER INFORMATION: Bgl2-UGT85C2-F

<400> SEQUENCE: 43
acagatctat ggatgcaatg gctacaactg aga                                    33

<210> SEQ ID NO 44
<211> LENGTH: 34
<212> TYPE: DNA
<213> ORGANISM: Artificial
<220> FEATURE:
<223> OTHER INFORMATION: Sal-UGT85C2-R
```

```
<400> SEQUENCE: 44
tagtcgacta gtttcttgct agcacggtga tttc                          34

<210> SEQ ID NO 45
<211> LENGTH: 42
<212> TYPE: DNA
<213> ORGANISM: Artificial
<220> FEATURE:
<223> OTHER INFORMATION: NotI-UGT91DIL3-F

<400> SEQUENCE: 45
aagcggccgc atgtacaacg ttacttatca tcaaaattca aa                 42

<210> SEQ ID NO 46
<211> LENGTH: 31
<212> TYPE: DNA
<213> ORGANISM: Artificial
<220> FEATURE:
<223> OTHER INFORMATION: Pac-UGT91D1L3-R

<400> SEQUENCE: 46
cgttaattaa ctctcatgat cgatggcaac c                             31

<210> SEQ ID NO 47
<211> LENGTH: 34
<212> TYPE: DNA
<213> ORGANISM: Artificial
<220> FEATURE:
<223> OTHER INFORMATION: Not-UGT74G1-F

<400> SEQUENCE: 47
aagcggccgc atggcggaac aacaaaagat caag                          34

<210> SEQ ID NO 48
<211> LENGTH: 37
<212> TYPE: DNA
<213> ORGANISM: Artificial
<220> FEATURE:
<223> OTHER INFORMATION: Pac-UGT74G1-R

<400> SEQUENCE: 48
cgttaattaa gccttaatta gctcacttac aaattcg                       37

<210> SEQ ID NO 49
<211> LENGTH: 33
<212> TYPE: DNA
<213> ORGANISM: Artificial
<220> FEATURE:
<223> OTHER INFORMATION: Bam-UGT76G1-F

<400> SEQUENCE: 49
aaggatccat ggaaaataaa acggagacca ccg                           33

<210> SEQ ID NO 50
<211> LENGTH: 44
<212> TYPE: DNA
<213> ORGANISM: Artificial
<220> FEATURE:
<223> OTHER INFORMATION: Sal-UGT76G1-R

<400> SEQUENCE: 50
gcgtcgactt acaacgatga aatgtaagaa actagagact ctaa               44
```

```
<210> SEQ ID NO 51
<211> LENGTH: 22
<212> TYPE: DNA
<213> ORGANISM: Artificial
<220> FEATURE:
<223> OTHER INFORMATION: UGT85C2-r1

<400> SEQUENCE: 51
caagtcccca accaaattcc gt                                            22

<210> SEQ ID NO 52
<211> LENGTH: 21
<212> TYPE: DNA
<213> ORGANISM: Artificial
<220> FEATURE:
<223> OTHER INFORMATION: UGT91D1L3-r1

<400> SEQUENCE: 52
cacgaacccg tctggcaact c                                             21

<210> SEQ ID NO 53
<211> LENGTH: 25
<212> TYPE: DNA
<213> ORGANISM: Artificial
<220> FEATURE:
<223> OTHER INFORMATION: UGT74G1-r1

<400> SEQUENCE: 53
cccgtgtgat tcttccact tgttc                                          25

<210> SEQ ID NO 54
<211> LENGTH: 21
<212> TYPE: DNA
<213> ORGANISM: Artificial
<220> FEATURE:
<223> OTHER INFORMATION: UGT76G1-r1

<400> SEQUENCE: 54
caagaaccca tctggcaacg g                                             21

<210> SEQ ID NO 55
<211> LENGTH: 28
<212> TYPE: DNA
<213> ORGANISM: Artificial
<220> FEATURE:
<223> OTHER INFORMATION: PGAL10-f3

<400> SEQUENCE: 55
gattattaaa cttctttgcg tccatcca                                      28

<210> SEQ ID NO 56
<211> LENGTH: 32
<212> TYPE: DNA
<213> ORGANISM: Artificial
<220> FEATURE:
<223> OTHER INFORMATION: PGAL1-f3

<400> SEQUENCE: 56
cctctatact ttaacgtcaa ggagaaaaaa cc                                 32
```

RHAMNOSE SYNTHASE DERIVED FROM STEVIA AND GENE

TECHNICAL FIELD

The present invention relates to a protein having an activity to produce rhamnose from glucose and a polynucleotide encoding this, and methods of producing rhamnose and a steviol glycoside using the protein.

BACKGROUND ART

The leaves of *Stevia rebaudiana* of the family Asteraceae contain a secondary metabolite called "steviol" which is a kind of diterpenoid. Some steviol glycosides have sweetness about 300 times higher than that of sucrose and are therefore used as non-caloric sweeteners in the food industry. Obesity is becoming more of a serious social issue on an international scale, and non-caloric sweeteners are increasingly demanded from the viewpoint of promotion of health and reduction of medical cost. Currently, aspartame and acesulfame potassium, which are artificially-synthesized amino acid derivatives, are used as artificial sweeteners. However, naturally-occurring non-caloric sweeteners such as steviol glycosides are expected to be safer and gain more public acceptance.

The main steviol glycosides in *Stevia rebaudiana* are modified with sugar finally into a glycoside called Rebaudioside A (Reb.A) having 4 sugars attached (FIG. 1). Its precursor stevioside, which is a trisaccharide glycoside, is most abundant and these 2 are central substances of the sweetness of *Stevia rebaudiana*. It is known that the stevioside content is highest in the leaves of *Stevia rebaudiana* and it exhibits sweetness about 250 to 300 times higher than that of sucrose. RebA is very sweet (350 to 450 times of that of sucrose) and is a tetrasaccharide glycoside, which is said to have good quality of taste. These have attracted attention as non-caloric sweeteners. In addition to these glycosides, glycosides considered to be reaction intermediates and analogs differing in the type of sugar are known to exist. For example, while the 4 glycoside sugars in RebA are all glucose, Rebaudioside C (RebC), in which rhamnose instead of glucose is added at position 2 of glucose at position 13, and Rebaudioside F (RebF), in which xylose was added at the same position, are known.

The genes of enzymes for bio-synthesis of RebA have been isolated by the Expressed Sequence Tag (EST) analysis of *Stevia rebaudiana* (Non-Patent Literatures 1 and 2, Patent Literature 1). Ent-kaurenoic acid, which is a precursor of gibberellin, a plant hormone diterpenoid, is hydroxylated at position 13 by ent-kaurenoic acid 13-hydroxylase (EK13H) to produce steviol (FIG. 1) (Patent Literature 1). Steviol is first glucosylated at the hydroxyl group at position 13 by UGT85C2, a UDP sugar-dependent glycosyltransferase (UGT) in *Stevia rebaudiana* to produce steviolmonoside (Non-Patent Literatures 1, 2). Steviolmonoside is further glucosylated at position 2 of glucose at position 13 to produce steviolbioside or glucosylated at the carboxyl group at position 19 to produce a disaccharide glycoside of steviol called rubusoside. As an enzyme that glucosylates steviolbioside or rubusoside at position 2 of glucose at position 13, UGT91D2 has been reported (previously referred to as UGT91D-like 3)) (Patent Literature 2). Meanwhile, position 3 of glucose at position 13 and carboxylic acid at position 19 have been reported to be glucosylated by UGT76G1 and UGT74G1, respectively (Non-Patent Literature 2). As described above, the genes of enzymes responsible for glycosylation to RebA have been identified, ectopic expression of biosynthetic enzymes for steviol glycosides in yeast and production of the steviol glycosides in culture have been reported (Patent Literature 3) and the industrial use of *Stevia rebaudiana* enzymes is in progress.

As steviol glycosides which comprise glycoside sugars other than glucose, RebC (containing rhamnose) and RebF (containing xylose) are known, but UGT enzymes that add a sugar other than glucose have not been elucidated. Furthermore, for the production of UDP-sugars other than glucose, a UDP-rhamnose synthase is reported for *Arabidopsis thaliana* (Non-Patent Literature 3) but not known for *Stevia rebaudiana*.

CITATION LIST

Patent Literature

[Patent Literature 1] EP 1 897 951 B1
[Patent Literature 2] WO2013/137487
[Patent Literature 3] WO2014/122328

Non-Patent Literature

[Non-Patent Literature 1] Brandle and Telmer (2007) Phytochemistry 68, 1855-1863
[Non-Patent Literature 2] Richman et al (2005) Plant J. 41, 56-67
[Non-Patent Literature 3] Oka et al (2007) J. Biol. Chem. 282, 5389-5403
[Non-Patent Literature 4] Natsume et al (2015) Plant Cell Physiol. 56, 428-441

SUMMARY OF INVENTION

Technical Problem

An object of the present invention is to provide a protein having an activity to produce rhamnose from glucose and a polynucleotide encoding this.

Solution to Problem

The present inventors have succeeded, as a result of diligent studies, in identifying amino acid sequences of SrRHM1 and SrRHM2 proteins producing rhamnose from glucose in *Stevia rebaudiana* and gene sequences encoding the proteins. The present invention is based on the findings.

Advantageous Effects of Invention

By using the enzyme according to the present invention, it is possible to produce rhamnose from glucose. Moreover, by using the rhamnose produced in this way, it is possible to produce a steviol glycoside having a rhamnose group. Moreover, by promoting or inhibiting the function of this enzyme, the kind of steviol glycoside in the plant of *Stevia rebaudiana* can be controlled. Furthermore, by using the gene that expresses the enzyme according to the present invention, it is possible to produce a steviol glycoside having a rhamnose group by metabolic engineering.

BRIEF DESCRIPTION OF DRAWINGS

FIG. 1 illustrates the names and structures of the steviol glycosides. In FIG. 1, "Glc-Glc" ($\beta 2 \rightarrow 1$) indicates that the binding of "Glc-Glc" is a β2,1 glycosidic linkage and "Glc-Glc" (β3→1) indicates that the binding of "Glc-Glc" is a β3,1 glycosidic linkage.

FIG. 2 illustrates a result of electrophoresis of PCR products in a 0.8% agarose gel and ethidium bromide staining.

FIG. 3 illustrates a result of CBB staining and Western blot analysis using an anti-HisTag antibody after the SDS-PAGE separation of the prepared enzyme.

FIG. 4-1 illustrates the activity to produce UDP-rhamnose from UDP-glucose in a negative control section.

FIG. 4-2 illustrates the activity to produce UDP-rhamnose from UDP-glucose in AtRHM2 from *Arabidopsis thaliana*.

FIG. 4-3 illustrates the activity to produce UDP-rhamnose from UDP-glucose in the recombinant SrRHM1#1.

FIG. 4-4 illustrates the activity to produce UDP-rhamnose from UDP-glucose in the recombinant SrRHM1#2.

FIG. 4-5 illustrates the activity to produce UDP-rhamnose from UDP-glucose in the recombinant SrRHM1#3.

FIG. 4-6 illustrates the activity to produce UDP-rhamnose from UDP-glucose in the recombinant SrRHM2#1.

FIG. 4-7 illustrates the activity to produce UDP-rhamnose from UDP-glucose in the recombinant SrRHM2#2.

FIG. 5 illustrates the specific activities of the SrRHM recombinant proteins.

FIG. 6 illustrates the expression of the SrRHM genes in each plant obtained in Example 4.

FIG. 7 illustrates the coexpression of RHM from *Stevia rebaudiana* and UGT85C2, UGT91D2L#16, UGT74G1 and UGT76G1 in yeast.

DESCRIPTION OF EMBODIMENTS

The present invention will be described in detail below. The following embodiments are illustrations for describing the present invention and it is not intended to limit the present invention to only these embodiments. The present invention can be embodied in various forms that do not deviates from the spirit of the present invention. All literature and patent literature such as unexamined patent publications and patent publications cited herein are incorporated herein by reference. Moreover, the present specification includes the contents of the specification and the drawings of the Japanese patent application (Japanese Patent Application No. 2017-079041, filed on Apr. 12, 2017) from which the present application claims the priority.

The present inventors have for the first time succeeded in identifying the amino acid sequences of the SrRHM1 protein and the SrRHM2 protein that produce rhamnose from glucose in *Stevia rebaudiana* and the gene sequences encoding the proteins. The SrRHM1 protein includes three mutants SrRHM1#1, SrRHM1#2 and SrRHM1#3, the amino acid sequences of which are SEQ ID NOs: 2, 4 and 6, respectively, and the CDS sequences of which are represented by SEQ ID NOs: 1, 3 and 5, respectively. The SrRHM2 protein includes two mutants SrRHM2#1 and SrRHM2#2, the amino acid sequences of which are SEQ ID NOs: 8 and 10, respectively, and the CDS sequences of which are represented by SEQ ID NOs: 7 and 9, respectively.

Here, the term "SrRHM1 protein" includes the protein of each of three mutants SrRHM1#1, SrRHM1#2 and SrRHM1#3, and the term "SrRHM2 protein" includes the protein of each of two mutants SrRHM2#1 and SrRHM2#2.

The polynucleotides and enzymes can be obtained by the techniques described in Examples below, known genetic engineering techniques, known synthetic methods, and the like.

1. Rhamnose Synthase from *Stevia rebaudiana*

The present invention provides a protein (hereinafter, referred to as the "protein according to the present invention") according to any one selected from the group consisting of the following (a) to (c):

(a) a protein consisting of the amino acid sequence of SEQ ID NO: 2, 4, 6, 8, or 10;

(b) a protein consisting of an amino acid sequence wherein 1 to 33 amino acids are deleted, substituted, inserted, and/or added in the amino acid sequence of SEQ ID NO: 2, 4, 6, 8, or 10 and having an activity to produce rhamnose from glucose;

(c) a protein having an amino acid sequence having a sequence identity of 95% or more to the amino acid sequence of SEQ ID NO: 2, 4, 6, 8, or 10 and having an activity to produce rhamnose from glucose.

The proteins described in above (b) or (c), are typically naturally occurring mutants of polypeptides of SEQ ID NO: 2, 4, 6, 8, or 10, but include those that can be obtained artificially by using site-directed mutagenesis described in, for example, "Sambrook & Russell, Molecular Cloning: A Laboratory Manual Vol. 3, Cold Spring Harbor Laboratory Press, 2001", "Ausubel, Current Protocols in Molecular Biology, John Wiley & Sons, 1987-1997", "Nuc. Acids. Res., 10, 6487 (1982)", "Proc. Natl. Acad. Sci. USA, 79, 6409 (1982)", "Gene, 34, 315 (1985)", "Nuc. Acids. Res., 13, 4431 (1985)", "Proc. Natl. Acad. Sci. USA, 82, 488 (1985)", or the like.

As used herein, the "protein consisting of an amino acid sequence wherein 1 to 33 amino acids are deleted, substituted, inserted, and/or added in the amino acid sequence of SEQ ID NO: 2, 4, 6, 8, or 10 and having an activity to produce rhamnose from glucose" includes a protein consisting of an amino acid sequence wherein, for example, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or 1 amino acid residue(s) is/are deleted, substituted, inserted, and/or added, in the amino acid sequence set forth in SEQ ID NO: 2, 4, 6, 8, or 10 and having an activity to produce rhamnose from glucose. In general, the number of amino acid residues in the aforementioned deletion, substitution, insertion, and/or addition is preferably smaller.

Moreover, examples of such a protein include a protein having an amino acid sequence having a sequence identity of 95% or more, 96% or more, 97% or more, 98% or more, 99% or more, 99.1% or more, 99.2% or more, 99.3% or more, 99.4% or more, 99.59% or more, 99.6% or more, 99.7% or more, 99.8% or more, or 99.9% or more to the amino acid sequence of SEQ ID NO: 2, 4, 6, 8 or 10 and having an activity to produce rhamnose from glucose. In general, the numerical value of the aforementioned sequence identity is preferably greater.

Here, the "activity to produce rhamnose from glucose" means an activity to produce rhamnose from glucose as shown by the following formula.

[Formula 1]

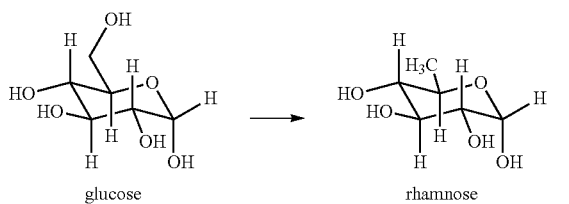

glucose    rhamnose

According to a preferred aspect of the present invention, the aforementioned glucose is in the form of uridine diphosphate glucose. Moreover, according to another preferred aspect of the present invention, the aforementioned rhamnose is in the form of uridine diphosphate rhamnose.

Alternatively, in the production of rhamnose from glucose using the protein according to the present invention, 4-keto-6-deoxyglucose having the following structure may be obtained as an intermediate.

[Formula 2]

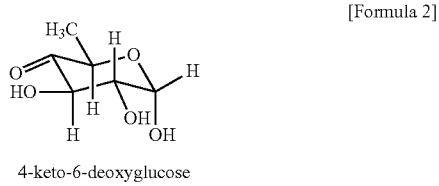

4-keto-6-deoxyglucose

The activity to produce rhamnose from glucose can be validated by incubating a buffer solution (for example, a sodium phosphate buffer or a potassium phosphate buffer) in a neutral region of pH 6.0 to 8.0 containing a test protein and a 1 to 1000 μM (preferably 100 to 700 μM and most preferably 500 μM) of glucose (for example, UDP-glucose) at a temperature of 20 to 40° C. for from 10 minutes to 2 hours followed by purification, and analyzing the purified product by a known technique such as the liquid chromatography-mass spectrometry (LC-MS) analysis.

If rhamnose is detected as a result of the LC-MS analysis, then the test protein is considered to be that having an activity to produce rhamnose from glucose.

The aforementioned rhamnose production reaction is usually completed in around 1 minute to 12 hours.

The one or more amino acid residues deleted, substituted, inserted, and/or added in the amino acid sequence of the protein according to the present invention means that there is deletion, substitution, insertion, and/or addition of one or more amino acid residues at the position(s) of any one or more amino acid sequences in the same sequence. Two or more of the deletion, substitution, insertion, and addition may occur simultaneously.

Examples of amino acid residues that may be substituted with each other are illustrated below. The amino acid residues included in a group may be substituted with each other. Group A: leucine, isoleucine, norleucine, valine, norvaline, alanine, 2-aminobutanoic acid, methionine, o-methylserine, t-butylglycine, t-butylalanine, cyclohexylalanine; Group B: aspartic acid, glutamic acid, isoaspartic acid, isoglutamic acid, 2-aminoadipic acid, 2-aminosuberic acid; Group C: asparagine, glutamine; Group D: lysine, arginine, ornithine, 2,4-diaminobutanoic acid, 2,3-diaminopropionic acid; Group E: proline, 3-hydroxyproline, 4-hydroxyproline; Group F: serine, threonine, homoserine; Group G: phenylalanine, tyrosine.

The protein according to the present invention can be obtained by expressing a polynucleotide (see the "Polynucleotide of the present invention" below) encoding this in an appropriate host cell, but it can be produced by a chemical synthetic method such as the fluorenylmethyl oxycarbonyl (Fmoc) method, the t-butyloxycarbonyl (tBoc) method, or the like. Moreover, the protein according to the present invention can be chemically synthesized with a peptide synthesizer such as that manufactured by Advanced Automation Peptide Protein Technologies, Inc., PerkinElmer, Inc., Protein Technologies Ltd., PerSeptive Biosystems, Inc., Applied Biosystems, or SHIMADZU CORPORATION.

2. Method of Producing Rhamnose

Rhamnose can easily be produced in large amounts by making use of the activity to produce rhamnose from glucose that the protein according to the present invention has.

Therefore, in another embodiment, the present invention provides a method of producing rhamnose, comprising reacting the protein according to the present invention and glucose. Specifically, the method of producing rhamnose according to the present invention is a method of producing rhamnose, comprising reacting glucose and the protein according to any one selected from the group consisting of the following (a) to (c):

(a) a protein consisting of the amino acid sequence of SEQ ID NO: 2, 4, 6, 8 or 10;

(b) a protein consisting of an amino acid sequence wherein 1 to 33 amino acids are deleted, substituted, inserted, and/or added in the amino acid sequence of SEQ ID NO: 2, 4, 6, 8 or 10 and having an activity to produce rhamnose from glucose;

(c) a protein having an amino acid sequence having a sequence identity of 95% or more to the amino acid sequence of SEQ ID NO: 2, 4, 6, 8 or 10 and having an activity to produce rhamnose from glucose.

Here, the aforementioned (a) to (c) are as described above for the "protein according to the present invention". Moreover, according to a preferred aspect of the present invention, the aforementioned glucose is in the form of uridine diphosphate glucose. Moreover, according to another preferred aspect, the aforementioned rhamnose is in the form of uridine diphosphate rhamnose. Alternatively, in the production of rhamnose from glucose using the transformant according to the present invention, 4-keto-6-deoxyglucose having the above structure may be obtained as an intermediate.

The first method of producing rhamnose according to the present invention may further comprise purifying the product in the aforementioned step.

The produced rhamnose can be purified by a known method such as extraction with an appropriate solvent (an aqueous solvent such as water or an organic solvent such as alcohol, ether, and acetone), the gradient of an organic solvent such as ethyl acetate:water, high performance liquid chromatography (HPLC), or ultra (high) performance liquid chromatography (UPLC).

According to another aspect of the present invention, a sweetener, a food or beverage, or a pharmaceutical product comprising the rhamnose or uridine diphosphate rhamnose obtained by the method of producing rhamnose according to the present invention is provided. Examples of the sweetener, the food or beverage, or the pharmaceutical product will be described below. Moreover, according to still another aspect of the present invention, a steviol glycoside comprising at least one rhamnose obtained by the method of producing rhamnose according to the present invention is provided. As used herein, the "steviol glycoside comprising at least one rhamnose" means a "steviol glycoside having at least one rhamnose group".

3. Non-Human Transformant Highly Containing Rhamnose

The rhamnose can be produced in cells of a bacterium (*Escherichia coli*, yeast, or the like), a plant, a microorganism, an insect, or a mammal other than human using the protein according to the present invention. This is because the protein according to the present invention is an enzyme from *Stevia rebaudiana* or a variant thereof and therefore expected to have high activity in the intracellular environment. In this case, rhamnose or UDP-rhamnose can be produced by introducing a vector comprising a polynucleotide encoding the protein according to the present invention (see the "polynucleotide of the present invention" described below) and a expression cassette into host cells from a bacterium, a microorganism, a plant, an insect, or a mammal other than human or the like to express the protein according to the present invention and reacting the protein according to the present invention and glucose or UDP-glucose present in the aforementioned cells.

Accordingly, the present invention provides a non-human transformant (hereinafter, referred to as the "transformant of the present invention") in which a polynucleotide described in any one selected from the group consisting of the following (a) to (d) is introduced (hereinafter, referred to as the "polynucleotide of the present invention").

(a) a polynucleotide comprising the nucleotide sequence of SEQ ID NO: 1, 3, 5, 7, or 9;

(b) a polynucleotide encoding a protein consisting of the amino acid sequences of SEQ ID NO: 2, 4, 6, 8, or 10;

(c) a polynucleotide encoding a protein consisting of an amino acid sequence wherein 1 to 33 amino acids are deleted, substituted, inserted, and/or added in the amino acid sequence of SEQ ID NO: 2, 4, 6, 8, or 10 and having an activity to produce rhamnose from glucose;

(d) a polynucleotide encoding a protein having an amino acid sequence having a sequence identity of 95% or more to the amino acid sequence of SEQ ID NO: 2, 4, 6, 8, or 10 and having an activity to produce rhamnose from glucose:

According to a preferred aspect of the present invention, the aforementioned glucose is in the form of uridine diphosphate glucose. Moreover, according to another preferred aspect of the present invention, the aforementioned rhamnose is in the form of uridine diphosphate rhamnose. Alternatively, in the production of rhamnose from glucose using the transformant according to the present invention, 4-keto-6-deoxyglucose having the above structure may be obtained as an intermediate.

As used herein, the "polynucleotide" means DNA or RNA. The polynucleotide of the present invention described above can be obtained by a known genetic engineering technique or a known synthetic method.

The polynucleotide of the present invention is preferably introduced into a host in a state inserted into an appropriate expression vector.

An appropriate expression vector is usually configured to comprise:
(i) a promoter that allows the transcription in host cells,
(ii) the polynucleotide of the present invention connected to the promoter; and
(iii) an expression cassette comprising signals that function in host cells as a component for the termination of transcription of RNA molecules and the polyadenylation.

Examples of the method of producing the expression vector include, but are not particularly limited to, methods using a plasmid, a bacteriophage, a cosmid or the like.

The specific kind of vector is not particularly limited, but a vector expressible in host cells can be selected as appropriate. More specifically, a vector obtained by selecting a promoter sequence that ensures the expression of the polynucleotide of the present invention, as appropriate, depending on the kind of host cells and incorporating the promoter and the polynucleotide of the present invention into a certain plasmid may be used as an expression vector.

The expression vector according to the present invention contains an expression regulatory region (for example, a promoter, a terminator, and/or a replication origin) depending on the kind of the host in which the expression vector is to be introduced. A conventional promoter (for example, trc promoter, tac promoter, lac promoter) is used as the promoter of the expression vector for bacteria, examples of a promoter for yeast include the GAL1 promoter, the GAL10 promoter, the glyceraldehyde-3-phosphate dehydrogenase promoter, the PHO5 promoter, and the like, and examples of a promoter for filamentous fungi include those for amylase and trpC, and the like. Moreover, examples of a promoter for expressing a gene of interest in plant cells include a vector having a promoter that allows the constitutive expression of a polynucleotide in plant cells or a vector having a promoter that is inductively activated by an external stimulus. Examples of the promoter that allows the constitutive expression of a polynucleotide include the 35S RNA promoter from cauliflower mosaic virus, the rd29A gene promoter, the rbcS promoter and the mac-1 promoter. Examples of the promoter inducibly activated by an external stimulus include the mouse mammary tumor virus (MMTV) promoter, the tetracycline responsiveness promoter, the metallothionein promoter, the heat shock protein promoter, and the like. Examples of a promoter for an animal cell host include a viral promoter (for example, the SV40 early promoter, the SV40 late promoter, or the like).

The expression vector preferably comprises at least one selection marker. Such markers that are available include auxotrophic markers (ura5, niaD, TRP1, URA3, HIS3, LEU2), drug resistance markers (hygromycin, Zeocin), Geneticin resistance genes (G418r), copper resistance genes (CUP1) (Marin et al., Proc. Natl. Acad. Sci. USA, vol. 81, p. 337, 1984), and cerulenin resistance genes (fas2m, PDR4) (Inokoshi, Junji, et al., Biochemistry, vol. 64, p. 660, 1992; and Hussain et al., Gene, vol. 101, p. 149, 1991, respectively).

The transformant according to the present invention is expected to produce a rhamnose at high efficiency. The host cells to be used in transformation are not particularly limited, but various known cells may suitably be used. Examples of the host cells include bacteria such as *Escherichia coli*, microorganisms such as yeast (the budding yeast *Saccharomyces cerevisiae* or the fission yeast *Schizosaccharomyces pombe*), plant cells, and animal cells other than human cells.

The aforementioned appropriate culture media and conditions for host cells are well-known in the art. Moreover, the organism to be transformed is not particularly limited, but examples thereof include the microorganisms, plants, or animals other than humans illustrated for the aforementioned host cells.

For other general techniques in molecular biology, see Sambrook & Russell, "Molecular Cloning: A Laboratory Manual" Vol. 3, Cold Spring Harbor Laboratory Press 2001;

"Methods in Yeast Genetics, A laboratory manual" (Cold Spring Harbor Laboratory Press, Cold Spring Harbor, N.Y.).

In one aspect of the present invention, the host cells for transformation to be used may be any yeast. Specifically, the host cells include, but are not limited to, yeast such as those in the genus *Saccharomyces*.

Examples of available methods of transforming yeast include known methods that are generally used. The transformation can be conducted by methods such as, but not limited to, those described in Meth. Enzym., 194, p 182 (1990) (electroporation); Proc. (12) JP 4918504 B2 2012.4.18 Natl. Acad. Sci. USA, 75 p 1929(1978) (the spheroplast method); J. Bacteriology, 153, p. 163 (1983) (the lithium acetate method); Proc. Natl. Acad. Sci. USA, 75 p. 1929 (1978); Methods in yeast genetics, 2000 Edition: A Cold Spring Harbor Laboratory Course Manual; and the like. The transformant strain is obtained by selecting a strain that grows in a medium with a selective pressure for the selection marker used (for example, a medium containing an antibiotic or a medium lacking a nutrient).

In one aspect of the present invention, the host cells to be used in transformation may be any plant. The plant transformant according to the present embodiment is obtained by introducing a recombinant vector containing the polynucleotide according to the present invention into a plant body such that the polypeptide encoded by the polynucleotide can be expressed. Alternatively, a new plant having the gene can be obtained by using the transformant according to the present invention as a crossing parent since the gene of the present invention is inherited by offspring.

The plant body to be transformed in the present invention means the whole plant body, a plant organ (for example, a leaf, a petal, a stem, a root, a seed, or the like), plant tissue (for example, epidermis, phloem, parenchyma, xylem, vascular bundle, palisade tissue, spongy tissue, or the like) or cultured plant cells, various forms of plant cells (for example, suspension cultured cells), protoplasts, a leaf section, callus, or the like. The plant to be used in transformation is not particularly limited, but may be any of plants belonging to Monocotyledoneae or Dicotyledoneae. Particularly preferable examples desirable to be used include plants known to bio-synthesize various glycosides using steviol as aglycones and examples of such a plant include *Stevia rebaudiana* and *Rubus suavissimus*.

The introduction of a gene into a plant body is conducted by a method of transformation known to those skilled in the art (for example, the *Agrobacterium* method, the gene gun method, the PEG method, electroporation, particle bombardment, or the like).

The cells or plant tissue in which a gene has been introduced is first selected for drug resistance such as the hygromycin resistance and then reproduced into a plant by a conventional method. The reproduction of a plant from transformed cells may be conducted by a method known to those skilled in the art depending on the kind of the plant cells.

Whether the polynucleotide of the present invention has been introduced into a plant or not can be confirmed by PCR, Southern hybridization, Northern hybridization, or the like.

By culturing the transformant obtained in this way, it is possible to have the transformant produce rhamnose. As described above, the production of rhamnose can be promoted by adding glucose or a plant extract containing glucose as a substrate to a culture system of the transformant. The rhamnose of interest can be obtained by extracting and purifying the accumulated product.

4. Extract of Transformant and Use Thereof

In another embodiment, the present invention also provides an extract of the aforementioned transformant. Since the transformant according to the present invention contains rhamnose at a higher content than the wild type when it has an appropriate substrate or when an appropriate substrate is added from the outside, extracts thereof are considered to contain steviol glycosides having rhamnose or a rhamnose group at high concentrations.

The extract of the transformant according to the present invention can be obtained by homogenizing the transformant using glass beads, a homogenizer, or a sonicator, centrifuging the resultant homogenate, and collecting the supernatant. Furthermore, a further extraction step by the methods of extracting rhamnose described above may be conducted.

The extract of the transformant according to the present invention can be used, according to a conventional method, for a purpose such as the production of a sweetener, food or beverage, a pharmaceutical product, an industrial raw material, or the like.

In another embodiment, the present invention also provides a sweetener, food or beverage, a medicament, an industrial raw material (a raw material for a food, beverage, or the like) comprising an extract of the transformant according to the present invention. The sweetener, food or beverage, medicament, or industrial raw material containing an extract of the transformant according to the present invention is prepared according to a conventional method. As seen above, the sweetener, food or beverage, medicament or industrial raw material, or the like containing an extract of the transformant according to the present invention contains a steviol glycoside having rhamnose or a rhamnose group produced using the transformant according to the present invention.

Examples of the food or beverage of the present invention include a dietary supplement, a health food, a food for specified health uses, a food with functional claims, a food for infants, and a food for the elderly. As used herein, the food is a solid, a fluid, and a liquid, and a mixture thereof and is a generic name for edibles.

The dietary supplement refers to a food enriched with a particular nutrition ingredient. The health food refers to a food that is healthy or considered to be good for health and includes a dietary supplement, a natural food, a diet food, and the like. The food for specified health uses is a food which contains ingredients having an effect on physiological functions of the body, and the like, of which the effects of specific health have been scientifically proven, and which has undergone efficacy and safety evaluation by presenting the scientific evidence to the country. The food with functional claims is a food that has been submitted to the Consumer Affairs Agency as indicating its functionality on its product package based on the scientific evidence. The food for infants refers to a food for feeding a child to up to about 6 years old. The food for the elderly refers to a food treated so as to be more easily digested and absorbed than a food with no treatment.

The food or beverage of the present invention uses a steviol glycoside having rhamnose or a rhamnose group as a sweetener. Therefore, the food of the present invention is low-calorie and has a merit of contributing to health promotion or health maintenance.

Examples of the forms of these foods or beverages may be agricultural foods such as bread, noodles, pasta, rice, confectionery (a cake, ice cream, popsicles, doughnuts, baked confectionery, candy, chewing gum, gummy candy, tablets, and Japanese sweets such as a dumpling and a steamed bun), tofu and processed products thereof; fermented foods such as refined sake, alcoholic drinks with medical properties, sweet sake, vinegar, soy sauce, and miso; livestock foods such as yogurt, ham, bacon, and sausage; sea foods such as kamaboko, fried fish paste, and cakes of ground fish; fruit juice beverages, refreshing beverages, sports beverages, alcoholic beverages; tea, and the like or flavoring agents. Examples of the forms of further foods include low calorie beverage, non-sugar beverage, canned fruits, milk beverage, beverage powder, yogurt, Jelly, dressing, noodle soup, pickle, a food boiled down in soy, soy sauce, miso, fish guts pickled in salt, Vermont vinegar, sweet pickled scallions, sweet and sour ginger, and a pickled lotus root, as well as a pickle, sauces for tempura and kabayaki, sauce for grilled meats, sources, gum, candy, toothpaste, a deep-fried patty of fish paste, rolled omelet, chow mein source, sauce for cold Chinese noodles, cut mackerel sprinkled with salt and then pickled in vinegar, ice cream, sherbet, soft ice cream, fish paste, snack food, rice confectionery, a corn cup, seasoned laver, bits of tempura batter that have fallen into the hot oil and been deep-fried, flaked seasoning for sprinkling over rice, and the like.

The dosage form of the pharmaceutical product (composition) according to the present invention is not particularly limited, and may be any dosage form, such as a solution, paste, gel, solid, or powder.

The pharmaceutical composition according to the present invention may further comprise another pharmaceutically active ingredients (for example, an anti-inflammatory ingredient) or an auxiliary ingredient (for example, a lubricant ingredient, a carrier ingredient) as needed.

5. Method of Producing Steviol Glycoside Having Rhamnose Group

According to another aspect of the present invention, a method of producing a steviol glycoside, comprising: reacting glucose and the protein according to the present invention to obtain rhamnose; and transferring the rhamnose to a steviol or steviol glycoside is provided. Specifically, the method of producing a steviol glycoside according to the present invention is a method of producing a steviol glycoside, comprising:

reacting glucose and the protein according to any one selected from the group consisting of the following (a) to (c) to obtain rhamnose:
(a) a protein consisting of the amino acid sequence of SEQ ID NO: 2, 4, 6, 8 or 10;
(b) a protein consisting of an amino acid sequence wherein 1 to 33 amino acids are deleted, substituted, inserted, and/or added in the amino acid sequence of SEQ ID NO: 2, 4, 6, 8 or 10 and having an activity to produce rhamnose from glucose;
(c) a protein having an amino acid sequence having a sequence identity of 95% or more to the amino acid sequence of SEQ ID NO: 2, 4, 6, 8 or 10 and having an activity to produce rhamnose from glucose; and
transferring the rhamnose to a steviol or steviol glycoside.

The step of reacting glucose and the protein of the present invention to obtain rhamnose is as described in "2. Method of producing rhamnose". The step of transferring the rhamnose to a steviol or steviol glycoside is not particularly limited as long as it can transfer rhamnose to a steviol or steviol glycoside, but it may be performed by using an enzyme that transfers rhamnose to a steviol or steviol glycoside. Such an enzyme that can be used is the enzyme UGT91D2 (SEQ ID NO: 11), the enzyme UGT91D2#16 (SEQ ID NO: 13), or the like. Moreover, rhamnose can be transferred to steviol or a steviol glycoside by using host cells in which the genes (SEQ ID NOs: 12 and 14) encoding such an enzyme are introduced. According to a preferred aspect of the present invention, the step of transferring the rhamnose to steviol or a steviol glycoside may be performed by using a non-human transformant in which (i) a polynucleotide comprising the nucleotide sequence of SEQ ID NO: 11 or 13; or (ii) a polynucleotide encoding a protein having an amino acid sequence having a sequence identity of 90% or more to the amino acid sequence of SEQ ID NO: 12 or 14 and having an activity to add rhamnose to glucose at position 13 in the steviol glycoside via a 1→2 bond is introduced.

Furthermore, a more highly glycosylated steviol glycoside (for example, dulcoside A, Rebaudioside C, Rebaudioside N and Rebaudioside O with a rhamnose group in *Stevia rebaudiana*) can be produced by using host cells in which a gene encoding a glycosyltransferase involved in a series of glycoside synthesis from steviol to Rebaudioside C is introduced or such a gene is expressed and expressing the polynucleotide of the present invention in the host cells. Examples of the glycosyltransferase involved in a series of glycoside synthesis from steviol to Rebaudioside C and a gene thereof include UGT91D2 (CDS sequence: SEQ ID NO: 11, amino acid sequence: SEQ ID NO: 12), UGT91D2#16 (CDS sequence: SEQ ID NO: 13, amino acid sequence: SEQ ID NO: 14), UGT85C2 (CDS sequence: SEQ ID NO: 15, amino acid sequence: SEQ ID NO: 16), UGT74G1 (CDS sequence: SEQ ID NO: 17, amino acid sequence: SEQ ID NO: 18), and UGT76G1 (CDS sequence: SEQ ID NO: 19, amino acid sequence: SEQ ID NO: 20). In a preferred aspect, the method for producing the steviol glycoside according to the present invention further comprises using a non-human transformant in which at least one polynucleotide of the following (a) to (e) is introduced:

(a) (i) a polynucleotide comprising the nucleotide sequence of SEQ ID NO: 15; or (ii) a polynucleotide encoding a protein having an amino acid sequence having a sequence identity of 90% or more to the amino acid sequence of SEQ ID NO: 16 and having an activity to add glucose to the hydroxyl group at position 13 in a steviol glycoside;

(b) (i) a polynucleotide comprising the nucleotide sequence of SEQ ID NO: 17; or (ii) a polynucleotide encoding a protein having an amino acid sequence having a sequence identity of 90% or more to the amino acid sequence of SEQ ID NO: 18 and having an activity to add glucose to the carboxylic acid at position 19 in a steviol glycoside;

(c) (i) a polynucleotide comprising the nucleotide sequence of SEQ ID NO: 19; or (ii) a polynucleotide encoding a protein having an amino acid sequence having a sequence identity of 90% or more to the amino acid sequence of SEQ ID NO: 20 and having an activity to add glucose at position 3 of the glucose at position 13 in a steviol glycoside via a 1→3 bond;

(d) (i) a polynucleotide comprising the nucleotide sequence of SEQ ID NO: 11 or 13; or (ii) a polynucleotide encoding a protein having an amino acid sequence having a sequence identity of 90% or more to the amino acid sequence of SEQ ID NO: 12 or 14 and having an activity to add glucose to the glucose at position 19 in a steviol glycoside via a 1→2 bond;

(e) (i) a polynucleotide comprising the nucleotide sequence of SEQ ID NO: 19; or (ii) a polynucleotide encoding a protein having an amino acid sequence having a sequence identity of 90% or more to the amino acid sequence of SEQ ID NO: 20 and having an activity to add glucose to the glucose at position 19 in a steviol glycoside via a 1→3 bond.

The steviol glycoside is not particularly limited as long as it has a rhamnose group, but it is preferably selected from the group consisting of dulcoside A, Rebaudioside C, Rebaudioside N and Rebaudioside O or a combination thereof.

6. Method of Screening for Plant Depending on Content of Steviol Glycosides Having Rhamnose Group The present invention provides a method of screening for a plant depending on the content of steviol glycosides having a rhamnose group (hereinafter, referred to as the "screening method according to the present invention"). Here, the "screening" means identifying a plant with a predetermined content or more (or less) of steviol glycosides having a rhamnose group from the other plants, and selecting the plant with a high (or low) content of steviol glycosides having a rhamnose group. Specifically, the screening method according to the present invention is a method of screening for a plant with a high content of steviol glycosides having a rhamnose group, a plant with a low content of steviol glycosides having a rhamnose group, or a plant having no steviol glycoside having a rhamnose group. Therefore, by using the screening method according to the present invention, a plant with a high content of steviol glycosides not having a rhamnose group but containing only a glucose group can be also selected.

The screening method according to the present invention is a method of screening for a plant depending on the content of steviol glycosides having a rhamnose group, comprising: quantitatively determining a polynucleotide selected from the group consisting of the following (a) to (d) in a test plant; and screening the test plant depending on the content of the polynucleotide by comparing the content of the polynucleotide to the reference value:

(a) a polynucleotide comprising the nucleotide sequence of SEQ ID NO: 1, 3, 5, 7 or 9;

(b) a polynucleotide encoding a protein consisting of the amino acid sequences of SEQ ID NO: 2, 4, 6, 8 or 10;

(c) a polynucleotide encoding a protein consisting of an amino acid sequence wherein 1 to 33 amino acids are deleted, substituted, inserted, and/or added in the amino acid sequence of SEQ ID NO: 2, 4, 6, 8 or 10 and having an activity to produce rhamnose from glucose;

(d) a polynucleotide encoding a protein having an amino acid sequence having a sequence identity of 95% or more to the amino acid sequence of SEQ ID NO: 2, 4, 6, 8 or 10 and having an activity to produce rhamnose from glucose.

In a preferred aspect of the screening method according to the present invention, a method of screening for a plant depending on the content of steviol glycosides having a rhamnose group is provided, the method comprising: quantitatively determining a polynucleotide selected from the group consisting of the following (a') to (d') in a test plant; and screening the test plant depending on the content of the polynucleotide by comparing the content of the polynucleotide to the reference value:

(a') a polynucleotide comprising the nucleotide sequence of SEQ ID NO: 7 or 9;

(b') a polynucleotide encoding a protein consisting of the amino acid sequences of SEQ ID NO: 8 or 10;

(c') a polynucleotide encoding a protein consisting of an amino acid sequence wherein 1 to 33 amino acids are deleted, substituted, inserted, and/or added in the amino acid sequence of SEQ ID NO: 8 or 10 and having an activity to produce rhamnose from glucose;

(d') a polynucleotide encoding a protein having an amino acid sequence having a sequence identity of 95% or more to the amino acid sequence of SEQ ID NO: 8 or 10 and having an activity to produce rhamnose from glucose.

The first step of quantitatively determining the polynucleotide can be performed by a known method such as microarray, real-time PCR, Southern blotting or Northern blotting.

In the second step of screening the test plant depending on the content of the polynucleotide by comparing the content of the polynucleotide to the reference value, the "reference value" can be set as appropriate by those skilled in the art. For example, the reference value is defined as the amount of the polynucleotide contained in any part (such as a leaf, a stem or a root) in the plant of *Stevia rebaudiana*. In screening, when the amount of the polynucleotide contained in the corresponding part (such as a leaf, a stem or a root) in the test plant is more (less) than the reference value, the plant can be screened as a plant with a high (low) content of a steviol glycoside having a rhamnose group.

Alternatively, the reference value may be variable. For example, plural test plants are compared, and the test plant with the first to nth (wherein n is an integer of 1 or more) highest (lowest) amount of the polynucleotide can be screened as a plant with a high (low) content of a steviol glycoside having a rhamnose group. In this case, the amount of the polynucleotide of the test plant with the $(n+1)^{th}$ highest amount of the polynucleotide is a reference value.

EXAMPLES

The present invention will be described more specifically by Examples below, but the scope of the present invention is not limited to these Examples.

[Example 1] Isolation of Candidate Gene for Rhamnose Synthase

The molecular biological techniques used in this Example were according to methods described in Molecular Cloning (Sambrook et al., Cold Spring Harbor Laboratory Press, 2001) otherwise specified in detail.

The total RNA was extracted from *Stevia rebaudiana* leaves using the RNeasy Plant Mini kit (QIAGEN), and DNAs intermingled therewith was digested using a DNase Set (QIAGEN). The extracted RNAs was confirmed for the quality using BioAnalyzer RNA 6000 nano chip (Agilent technologies), and the cDNA library was constructed by a method recommended by those skilled in the art using TrueSeq Standard total RNA with RiboZero Plant Kit (Illumina). The constructed library was confirmed for the quality using BioAnalyzer DNA1000 chip (Agilent technologies) and then quantitatively determined using Cycleave PCR Quantification Kit (TaKaRa Bio). The library was subjected to Pair end (2×101 cycles) sequencing with a HiSeq1500 (Illumina) sequencer. The base sequences of the obtained reads were de novo assembled by the method described in (Non-Patent Literature 4) using the Trinity program to obtain EST information of *Stevia rebaudiana* leaves.

The obtained *Stevia rebaudiana* EST was subjected to homology search analysis by tBlastx using the known sequence information of AtRHM2 (SEQ ID NO: 21) (Non-Patent Literature 3) as a query. As a result, the *Stevia rebaudiana* genes, SrRHM1#1 gene (SEQ ID NO: 1) and SrRHM2#1 gene (SEQ ID NO: 7), which show sequence identities of 74% and 72% to AtRHM2 at the DNA level, respectively, were found.

To obtain the SrRHM1 gene and SrRHM2 gene that were found in *Stevia rebaudiana* leaves, PCR was performed using the following primer sets (SEQ ID NOs: 22 and 23, and SEQ ID NOs: 24 and 25) and cDNAs, which were prepared from a plurality of *Stevia rebaudiana* leaves from different strains, as templates.

```
SrRHM1-pET-FW
                                          (SEQ ID NO: 22)
TGCCGCGCGGCAGCCATATGGCTACTTACGTGCCAAAG

SrRHM1-pET-RV
                                          (SEQ ID NO: 23)
GTTAGCAGCCGGATCCTTAATGTTTTTTGTTAGGTTCGAATACG

SrRHM2Full-Fw
                                          (SEQ ID NO: 24)
TGCCGCGCGGCAGCCATATGACCAGTTATACACCTAAAAAC SrRHM2Full-Rv
                                          (SEQ ID NO: 23)
GTTAGCAGCCGGATCCTTAGGTTGTCTTGTTGGGTGCAAATAC
``` cDNA from *Stevia rebaudiana* leaves was obtained by extracting total RNA from *Stevia rebaudiana* leaves using RNeasy Plant Mini kit (QIAGEN) and reverse-transcribing 0.5 μg the total RNA with Random Oligo-dT primers (RT).

The PCR reaction solution (50 μl) was prepared to have the composition of 1 μl of cDNA from *Stevia rebaudiana* leaves, 1×ExTaq buffer (Takara Bio), 0.2 mM dNTPs, 0.4 pmol/μl each of primers, 2.5 U of ExTaq polymerase. The PCR reaction included the reaction at 94° C. for 3 minutes and subsequent amplification with total 30 cycles of the reaction at 94° C. for 1 minute, at 50° C. for 1 minute, and at 72° C. for 2 minutes. Electrophoresis of the PCR products on a 0.8% agarose gel and staining with ethidium bromide resulted in an amplified band at a size of about 2.0 kb estimated from each cDNA of SrRHM1 gene and SrRHM2 gene (FIG. 2).

Each of the PCR products at about 2 kb was cloned into the NdeI and BamHI sites of the pET15b vector (Novagen), and the sequencing was carried out by primer walking with the synthesized oligonucleotide primers with DNA Sequencer model 3100 (Applied Biosystems). As a result, the presence of a total of three SrRHM1 genes, SrRHM1#1 of SEQ ID NO: 1 as well as SrRHM1#2 and SrRHM1#3 (SEQ ID NOs: 3 and 5) exhibiting a sequence identity of 99% at the DNA level and the amino acid level with SrRHM1#1 gene was revealed. Similarly, SrRHM2#2 exhibiting a sequence identity of 99% at the DNA level and the amino acid level with SrRHM2#1 was obtained (SEQ ID NO: 9). Each of these SrRHM genes was designed such that the His tag upstream of the NdeI site in the vector is in frame with the opening reading frame of the inserted gene and a chimeric protein in which SrRHM1 and the His tag are fused is expressed.

SrRHM1#1, SrRHM1#2 and SrRHM1#3 from *Stevia rebaudiana* exhibited a sequence identity of 74% at the DNA level with AtRHM2 from *Arabidopsis thaliana*, and SrRHM2#1 and SrRHM2#2 exhibited a sequence identity of 72% at the DNA level with AtRHM2 from *Arabidopsis thaliana*.

[Example 2] Expression and Purification of Recombination Protein

To elucidate the biochemical function of the enzyme according to the present invention, the enzyme according to the present invention was expressed in *Escherichia coli*. The *Escherichia coli* strain BL21 (DE3) was transformed by a conventional method with the plasmids for *Escherichia coli* expression of the three SrRHM1 genes and the two SrRHM2 genes obtained as described above. The obtained transformant was cultured with shaking at 37° C. overnight in 4 ml of LB medium (10 g/l tryptone pepton, 5 g/l yeast extract, 1 g/l NaCl) containing 50 μg/ml ampicillin. 80 ml of the medium of the same composition was inoculated with 4 ml of the culture liquid reached to the stationary phase and the resultant culture was cultured with shaking at 37° C. IPTG was added at a final concentration of 0.5 mM when the bacterial turbidity (OD600) reached approximately 0.5 and the shaking culture was continued for 20 hr at 18° C.

All of the following operations were carried out at 4° C. The cultured transformant was collected by centrifugation (5,000×g, 10 min) and suspended by adding 1 ml/g cell of Buffer S [20 mM HEPES buffer (pH 7.5), 20 mM imidazole, 14 mM β-mercaptoethanol]. Subsequently, sonication (15 sec×8 times) and centrifugation (15,000×g, 15 min) were conducted. The obtained supernatant was collected as a crude enzyme liquid. The crude enzyme liquid was loaded onto His SpinTrap (GE Healthcare) equilibrated with Buffer S and centrifuged (70×g, 30 sec). After washing with the Buffer, proteins bound to the column were eluted stepwise with 5 ml each of Buffer S containing 100 mM and 500 mM imidazole. Each elution fraction was subjected to buffer exchange into 20 mM HEPES buffer (pH 7.5), 14 mM β-mercaptoethanol using Microcon YM-30 (Amicon) (dialysis against approximately 500 volumes).

As a result of CBB staining and Western blot analysis using an anti-HisTag antibody after the SDS-PAGE separation of the prepared enzyme, a protein not found in the negative control section (pET15b empty vector) was detected in the vicinity of the estimated molecular weight of about 75 kDa for the fusion chimeric protein of SrRHM1 or SrRHM2 and the His tag in the 200 mM imidazole elution fraction. Therefore, this fraction was used for the enzymatic analysis (FIG. 3).

[Example 3] Enzymatic Activity Measurement

The standard enzymatic reaction conditions are as follows. A reaction solution (100 mM potassium phosphate buffer (pH 7.5), 5 mM UDP-glucose (substrate), 2 mM NADPH, 5 mM DTT, 2 mM EDTA, 60 μl of purified enzyme solution) was prepared to 100 μl with distilled water and incubated at 30° C. for 24 hours to react. The LC-MS analysis of 5 μl of the enzymatic reaction solution was carried out under the following conditions.

LC Conditions
Column: TSKgel Amide—80 3 μm (2.0×150 mm)
Mobile phase: A:, B: Acetonitrile
Gradient: 0 to 0.2 min (B conc 95% constant),
   0.2 to 14.0 min (B conc 95%→30%),
   14.0 to 14.2 min (B conc 30%→95%)
   20 min end of analysis
Flow rate: 0.2 mL/min
Column oven: 40° C.
MS Conditions
ESI (negative mode)
MRM measurement(CE 25): m/z 565.1→323.0 (UDP-Glucose)
m/z 549.1→323.0 (UDP-Rhamnose)

The enzyme reaction solution was analyzed under the above conditions, and only the substrate UDP-glucose was detected in the experimental section of an empty vector as a negative control at a retention time of about 10 minutes (FIG. 4-1). Meanwhile, in addition to the substrate UDP-glucose, UDP-rhamnose was detected at a retention time of about 9.6 minutes in the reaction section of the recombinant protein of AtRHM2 from *Arabidopsis thaliana* as a positive control (FIG. 4-2).

Then, the recombinant proteins SrRHM1#1, SrRHM1#2 and SrRHM1#3 were reacted with UDP-glucose, respectively, and the synthesis of UDP-rhamnose was clearly confirmed in any of the reaction sections (FIGS. 4-3, 4-4 and 4-5).

Similarly, the activity of SrRHM2 was evaluated. The SrRHM2#1 and SrRHM2#2 proteins were reacted with UDP-glucose, respectively, and the synthesis of UDP-rhamnose was clearly confirmed in any of the reaction sections (FIGS. 4-6 and 4-7).

Next, the specific activities of these recombinant proteins were evaluated. The total of the amount of the UDP-glucose left after the reaction and the amount of UDP-rhamnose produced by the reaction was normalized to 1. As a result, the recombinant proteins according to the present invention (SrRHM1#1, SrRHM1#2 and SrRHM1#3 proteins as well as SrRHM2#1 and SrRHM2#2 proteins) were confirmed to have a higher rhamnose production activity than the recombinant protein of AtRHM2 from *Arabidopsis thaliana*. Moreover, it was confirmed that the SrRHM2 proteins tends to produce more rhamnose than the SrRHM1 proteins (FIG. 5).

The foregoing results showed that the SrRHM1#1, SrRHM1#2 and SrRHM1#3 proteins as well as the SrRHM2#1 and SrRHM2#2 proteins are UDP-rhamnose synthases expressed in *Stevia rebaudiana* leaves. Therefore, these enzymes are considered to be involved in the synthesis of dulcoside A, Rebaudioside C, Rebaudioside N and Rebaudioside O or the like having a rhamnose group in *Stevia rebaudiana*.

[Example 4] Gene Expression Analysis

For the expression of the two SrRHM genes that were found to be active this time, the presence or absence of expression in the leaves of independent *Stevia rebaudiana* plants (1, 2) containing RebC and *Stevia rebaudiana* plants (3, 4) in which RebC was not detected was determined by RT-PCR.

SrRHM1 was amplified with the primer sets of SEQ ID NOs: 22 and 23 and SrRHM2 was amplified with the primer sets of SEQ ID NOs: 24 and 25, with 32 cycles under the same conditions as in Example 1. *Stevia rebaudiana* actin gene (SrACTIN) was used as an internal standard gene and amplified with the primer sets of SEQ ID NOS: 26 and 27 (23 cycles).

```
SrRHM1-pET-FW
                                        (SEQ ID NO: 22)
TGCCGCDCGGCAGCCATATGGCTACTTACGTGCCAAAG

SrRHM1-pET-RV
                                        (SEQ ID NO: 23)
GTTAGCAGCCGGATCCTTAATGTTTTTTGTTAGGTTCGAATACG

SrRHM2Full-Fw
                                        (SEQ ID NO: 24)
TGCCGCGCGGCAGCCATATGACCAGTTATACACCTAAAAAC SrRH512Full-Rv
                                        (SEQ ID NO: 25)
GTTAGCAGCCGGATCCTTAGGTTGTCTTGTTGGGTGCAAATAC SrACTIN-Fw
                                        (SEQ ID NO: 26)
ATGGCCGATACTGAGGATATTCAG SrACTIN-Rv
                                        (SEQ ID NO: 27)
AGCACTTCCTGTGGACAATGGA
```

As a result, the gene expression of SrRHM2 was confirmed to specifically decrease in *Stevia rebaudiana* plants (3,4) in which RebC was not detected (FIG. 6). Therefore, it was shown that UDP-rhamnose used for the rhamnose transfer of steviol glycosides in *Stevia rebaudiana* leaves is mainly supplied by SrRHM2.

[Example 5] Fermentative Production of UDP-Rhamnose Using Yeast

Next, it was examined whether UDP-rhamnose could be synthesized in yeast using the obtained SrRHM1 and SrRHM2.

Construction of Expression Vector for Yeast

To incorporate the UDP-rhamnose synthase genes into a yeast expression vector, the following primer sets were designed.

```
StRHM1 Set
Apa-SrRHM1-F (Apai recognition site is underlined):
                                        (SEQ ID NO: 28)
5'-GGGCCCATGGCTACTTACGTGCCAAAG-3'

Xho-SrRHM1-R (XhoI recognition site is underlined):
                                        (SEQ ID NO: 29)
5'-CTCGAGTTAATGTTTTTTGTTAGGTTCGAATACG-3'

StRHM2 Set
Bam-SrRHM2-F(ApaI recognition site is underlined):
                                        (SEQ ID NO: 30)
5'-GGATCCATGACCAGTTATACACCTAAAAACATCC-3'

Xho-SrRHM2-R(XhoI recognition site is underlined):
                                        (SEQ ID NO: 31)
5'-CTCGAGTTAGGTTGTCTTGTTGGGTGC-3'
```

Using the combinations of template and primers, SrRHM1 as a template and the SrRHM1 set and SrRHM2 as a template and the SrRHM2 set, and heat-resistant KOD DNA polymerase (Toyobo), PCR amplification was conducted to add restriction enzyme sites to the both ends of each ORF. The obtained DNA fragments were subcloned using the zero Blunt-TOPO PCR cloning kit (Invitrogen) and the sequencing was carried out by primer walking with the synthesized oligonucleotide primers with DNA Sequencer model 3100 (Applied Biosystems) to confirm that each of the intended UGT genes was cloned.

To express the genes in yeast, the following expression vectors were constructed using the pESC yeast expression system (Stratagene).

Construction of plasmid pESC-TRP-SrRHM1

The plasmid pESC-TRP-SrRHM1 was obtained by cutting out SrRHM1 with the restriction enzymes ApaI and XhoI and ligating the SrRHM1 with the vector pESC-TRP (Stratagene) cut with the restriction enzyme ApaI and the restriction enzyme XhoI.

Construction of plasmid pESC-TRP-SrRHM2

The plasmid pESC-TRP-SrRHM2 was obtained by cutting out SrRHM2 with the restriction enzymes BamHI and XhoI and ligating the SrRHM2 with the vector pESC-TRP (Stratagene) cut with the restriction enzyme BamHI and the restriction enzyme XhoI.

Transformation of Yeast

The *Saccharomyces cerevisiae* strain YPH499 (ura3-52 lys2-801$^{amber}$ ade2-101$^{ochre}$ trp1-Δ63 his3-Δ200 leu2-Δ1a) as a host was transformed with the plasmids, pESC-TRP-SrRHM1 and pESC-TRP-SrRHM2 by the lithium acetate method. Those that grew on SC-Trp agar medium (6.7 g of Yeast nitrogen base without amino acids, 20 g of glucose, 1.3 g of amino acid mixture powder-Trp, 20 g of Bacto agar, per 1 L) were selected as transformant strains. The amino acid mixture powder-Trp was prepared by mixing 2.5 g of adenine sulfate, 1.2 g of L-arginine hydrochloride, 6.0 g of L-aspartic acid, 6.0 g of L-glutamic acid, 1.2 g of L-histidine, 3.6 g of L-leucine, 1.8 g of L-lysine, 1.2 g of L-methionine, 3.0 g of L-phenylalanine, 22.5 g of L-serine, 12 g of L-threonine, 1.8 g of L-tyrosine, 9.0 g of L-valine and 1.2 g of uracil. Meanwhile, the strain transformed with the vector pESC-TRP in the same manner as described above was used as a control strain (C-1 strain).

Induction and Analysis of Expression of Transgene

The obtained transformant strain was cultured as follows.

First, 10 ml of SC-Trp liquid medium (SC-Trp agar medium without Bacto agar) was inoculated with each transformant strain as a preculture and cultured with shaking at 30° C. for 1 day. Then, 10 ml of SG-Trp liquid medium (6.7 g of Yeast nitrogen base without amino acids, 20 g of galactose, 1.3 g of amino acid mixture powder-Trp, per 1 L) was inoculated with 1 ml of the liquid preculture as a main culture and cultured with shaking at 30° C. for 2 days.

To confirm whether the gene introduced in the transformant strain is expressed, bacterial cells were collected from the liquid culture and total RNA was purified with RNeasy Mini Kit.

cDNA was synthesized by taking 1 µg of the total RNA and using Super script II reverse transcriptase (Thermo Fisher Scientific) and random hexamers as primers.

To confirm the expression of the transgenes, the following primers were prepared.

```
For confirming expression of SrRHM1
SrRHM1-r1
                                    (SEQ ID NO: 32)
5'-CGAGTTAGGTATTTGGACACCA-3'

For confirming expression of SrRHM2
SrRHM2-r1
                                    (SEQ ID NO: 33)
5'-TACCGGGTCCTGAAAGATGAC-3'

GAL10p region (promoter region)
PGAL10-f3:
                                    (SEQ ID NO: 34)
5'-GATTATTAAACTTCTTTGCGTCCATCCA-3'
```

Expression of each transgene was confirmed by performing PCR using the following combinations of primers, the previously synthesized cDNA as template, and ExTaq (Takara Bio) and agarose gel electrophoresis of the products.

SrRHM1:SrRHM1-r1 (SEQ ID NO: 32) and PGAL10-f3 (SEQ ID NO: 34)

SrRHM2:SrRHM2-r1 (SEQ ID NO: 33) and PGAL10-f3 (SEQ ID NO: 34)

The strains in which the introduced genes could be confirmed to be expressed were designated as SR1-1 strain and SR2-1 strain.

Analysis of the UDP-Sugar 15 ml of ice-cooled 1 M formic acid (saturated with 1-butanol) was added to the yeast cells collected by centrifugation from 10 ml of the culture obtained by culturing in the same manner as the procedure for the above-described expression analysis, and was gently stirred at 4° C. for 1 hour. The supernatant from which the cells were removed by centrifugation was lyophilized. The obtained lyophilizate was dissolved in 200 µl of water and subjected to HPLC.

The HPLC conditions are as follows.

Column: COSMOSIL (R) 5$C_{18}$-ARII (4.6 mmI.D.×250 mm)

Column temperature: 40° C.

Mobile phase: 20 mM triethylamine acetate (pH 7.0), Flow rate: 1 ml/min

Detection: UV260

As a result, the production of UDP-rhamnose could not be confirmed in the C-1 strain, whereas the production of UDP-rhamnose could be confirmed in both the SR1-1 strain and the SR2-1 strain.

[Example 6] Production of RebC Using Yeast

Cloning of glycosylation enzyme gene cDNA from *Stevia rebaudiana*

The following primer sets were used for cDNA cloning.

```
Primer set for amplification of UGT85C2 gene
CACC-NdeI-SrUGT85C2-Fw (NdeI recognition site is
underlined):
                                    (SEQ ID NO: 35)
5'-CACCCATATGGATGCAATGGCTACAACTGAGAA-3'

BglII-SrUGT85C2-Rv(BglII recognition site is
underlined):
                                    (SEQ ID NO: 36)
5'-AGATCTCTAGTTTCTTGCTAGCACGGTGATTT-3'

Primer set for amplification of UGT91D2 and
UGT91D2#16 genes
SrUGT91D2-pET15b-FW
                                    (SEQ ID NO: 37)
5'-TGCCGCGCGGCAGCCATATGTACAACGTTACTTATCATC-3'

SrUGT91D2-pET15b-RV
                                    (SEQ ID NO: 38)
5'-GTTAGCAGCCGGATCCTTAACTCTCATGATCGATGGCAA-3'

Primer set for amplification of UGT74G1 gene
CACC-NdeI-SrUGT74G1 FW(NdeI recognition site is
underlined):
                                    (SEQ ID NO: 39)
5'-CACCCATATGGCGGAACAACAAAAGATCAAGAAAT-3'

BamHI-SrUGT74G1-Rv(BamHI recognition site is
underlined):
                                    (SEQ ID NO: 40)
5'-GGATCCTTAAGCCTTAATTAGCTCACTTACAAATT-3'

Primer set for amplification of UGT76G1 gene
CACC-NdeI-SrUGT76G1-Fw (NdeI recognition site is
underlined):
                                    SEQ ID NO: 41)
5'-CACCCATATGGAAAATAAAACGGAGACCA-3'

BamHI-SrUGT76G1-Rv (BamHI recognition site is
underlined):
                                    (SEQ ID NO: 42)
5'-GGATCCTTACAACGATGAAATGTAAGAAACTA-3'
```

The PCR reaction solution (50 µl) was prepared to have the composition of 1 µl of cDNA from *Stevia rebaudiana* leaves, 1×KOD plus buffer (TOYOBO), 0.2 mM dNTPs, 0.4 pmol/µl primers, 1 mM MgSO4, and 1 U heat-resistant KOD plus polymerase. The PCR reaction included the reaction at 95° C. for 5 minutes and subsequent amplification with total 30 cycles of the reaction at 94° C. for 0.5 minutes, at 50° C. for 0.5 minutes, and at 68° C. for 2 minutes. Electrophoresis of the PCR products on a 0.8% agarose gel and staining with ethidium bromide resulted in an amplified band at a size of about 1.4 kb estimated from each template DNA.

This PCR product was subcloned into pENTR-TOPO Directional vector (Invitrogen) in a way recommended by the manufacturer. The sequencing was carried out by primer walking with the synthesized oligonucleotide primers with DNA Sequencer model 3100 (Applied Biosystems) to confirm the cloning of all the intended UGT genes, that is to say, UGT85C2, UGT91D2 and UGT91D2#16, UGT74G1, and UGT76G1.

Construction of Expression Vector for Yeast

To incorporate these UGT and UDP-rhamnose synthase genes into a yeast expression vector, the following primer sets were designed.

SrUGT85C2 Set
Bgl2-UGT85C2-F (BglII recognition site is
underlined):
(SEQ ID NO: 43)
5'-AC<u>AGATCT</u>ATGGATGCAATGGCTACAACTGAGA-3'

Sal-UGT85C2-R (SalI recognition site is
underlined):
(SEQ ID NO: 44)
5'-TA<u>GTCGAC</u>TAGTTTCTTGCTAGCACGGTGATTTC-3'

SrUGT91D2 Set
NotI-UGT91DIL3-F (NotI recognition site is
underlined):
(SEQ ID NO: 45)
5'-AA<u>GCGGCCGC</u>ATGTACAACGTTACTTATCATCAAAATTCAAA-3'

Pac-UGT91D1L3-R (PacI recognition site is
underlined):
(SEQ ID NO: 46)
5'-CG<u>TTAATTAA</u>CTCTCATGATCGATGGCAACC-3'

SrUGT74G1 Set
Not-UGT74G1-F (NotI recognition site is
underlined):
(SEQ ID NO: 47)
5'-AA<u>GCGGCCGC</u>ATGGCGGAACAACAAAAGATCAAG-3'

Pac-UGT74G1-R (PacI recognition site is
underlined):
(SEQ ID NO: 48)
5'-CG<u>TTAATTAA</u>GCCTTAATTAGCTCACTTACAAATTCG-3'

SrUGT76G1 Set
Bam-UGT76G1-F (BamHI recognition site is
underlined):
(SEQ ID NO: 49)
5'-AA<u>GGATCC</u>ATGGAAAATAAAACGGAGACCACCG-3'

Sal-UGT76G1-R (SalI recognition site is
underlined):
(SEQ ID NO: 50)
5'-GC<u>GTCGAC</u>TTACAACGATGAAATGTAAGAAACTAGAGACTCTAA-3'

Using the combinations of template and primers, UGT85C2 as template and the SrUGT85C2 set, UGT91D2 or UGT91D2L#16 as template and the SrUGT91D2 set, UGT74G1 as template and the SrUGT74G1 set, UGT76G1 as template and the SrUGT76G1 set, and AtAHM2 as template and the AtAHM2 set, and heat-resistant KOD DNA polymerase (Toyobo), PCR amplification was conducted to add restriction enzyme sites to the both ends of each ORF. The obtained DNA fragments were subcloned using the zero Blunt-TOPO PCR cloning kit (Invitrogen) and the sequencing was carried out by primer walking with the synthesized oligonucleotide primers with DNA Sequencer model 3100 (Applied Biosystems) to confirm that each of the intended UGT genes was cloned.

To express the genes in yeast, the following expression vectors were constructed using the pESC yeast expression system (Stratagene).

(1) Construction of Plasmid pESC-URA-UGT56 or pESC-URA-UGT56R

The plasmid pESC-URA-UGT-1 was obtained by cutting out UGT85C2 with the restriction enzyme BglII and the restriction enzyme SalI and ligating the UGT85C2 into the vector pESC-URA (Stratagene) cut with the restriction enzyme BamHI and the restriction enzyme SalI. This plasmid pESC-URA-UGT-1 cut with the restriction enzyme NotI and the restriction enzyme PacI and UGT91D2 or UGT91D2L#16 cut with the restriction enzyme NotI and the restriction enzyme PacI were ligated to obtain pESC-URA-UGT56 or pESC-URA-UGT56R.

(2) Construction of Plasmid pESC-HIS-UGT78

The plasmid pESC-HIS-UGT-8 was obtained by cutting out UGT76G1 with the restriction enzyme BamHI and the restriction enzyme SalI and ligating the UGT76G1 with the vector pESC-HIS (Stratagene) cut with the same restriction enzymes. This plasmid pESC-HIS-UGT-8 cut with the restriction enzyme NotI and the restriction enzyme PacI and UGT74G1 cut with NotI and PacI were ligated to obtain pESC-HIS-UGT78.

Transformation of Yeast

The plasmids set forth in Table 1 were introduced into the *Saccharomyces cerevisiae* strain YPH499 (ura3-52 lys2-801$^{amber}$ ade2-101$^{ochre}$ trp1-Δ63 his3-Δ200 leu2-Δ1 a) as a host by the lithium acetate method. Those that grew on SC-Trp&Ura&His agar medium (6.7 g of Yeast nitrogen base without amino acids, 20 g of glucose, 1.3 g of amino acid mixture powder Trp&Ura&His, 20 g of Bacto agar, per 1 L) were selected as transformant strains.

TABLE 1

| Transformant strain | Introduced plasmid | Introduced gene |
|---|---|---|
| S1-5678 | pESC-URA-UGT56 | SrUGT85C2, SrUGT91D2 |
|  | pESC-HIS-UGT78 | SrUGT74G1, SrUGT76G1 |
|  | pESC-TRP-SrRHM1 | SrRHM1 |
| S2-56R78 | pESC-URA-UGT56 | SrUGT85C2, |
|  | pESC-HIS-UGT78 | SrUGT91D2L#16 |
|  | pESC-TRP-SrRHM1 | SrUGT74G1, SrUGT76G1 |
|  |  | SrRHM1 |
| S2-5678 | pESC-URA-UGT56 | SrUGT85C2, SrUGT91D2 |
|  | pESC-HIS-UGT78 | SrUGT74G1, SrUGT76G1 |
|  | pESC-TRP-SrRHM2 | SrRHM2 |
| 52-56R78 | pESC-URA-UGT56R | SrUGT85C2, UGT91D2L#16 |
|  | pESC-HIS-UGT78 | SrUGT74G1, SrUGT76G1 |
|  | pESC-TRP-SrRHM2 | SrRHM2 |
| C-5678 | pESC-URA-UGT56 | SrUGT85C2, SrUGT91D2 |
|  | pESC-HIS-UGT78 | SrUGT74G1, SrUGT76G1 |
|  | pESC-TRP |  |
| C-56R78 | pESC-URA-UGT56R | SrUGT85C2, UGT91D2L#16 |
|  | pESC-HIS-UGT78 | SrUGT74G1, SrUGT76G1 |
|  | pESC-TRP |  |

The amino acid mixture powder Trp&Ura&His was prepared by mixing 2.5 g of adenine sulfate, 1.2 g of L-arginine hydrochloride, 6.0 g of L-aspartic acid, 6.0 g of L-glutamic acid, 3.6 g of L-leucine, 1.8 g of L-lysine, 1.2 g of L-methionine, 3.0 g of L-phenylalanine, 22.5 g of L-serine, 12 g of L-threonine, 1.8 g of L-tyrosine, and 9.0 g of L-valine.

Induction and Analysis of Expression of Transgene

The obtained transformant strain was cultured as follows.

First, 10 ml of SC-Trp&Ura&His liquid medium (SC-Trp&Ura&His agar medium without Bacto agar) was inoculated each transformant strain as a preculture and cultured with shaking at 30° C. for 1 day. Then, 10 ml of SG-Trp&Ura&His liquid medium (6.7 g of Yeast nitrogen base without amino acids, 20 g of galactose, 1.3 g of amino acid mixture powder Trp&Ura&His, per 1 L) was inoculated with 1 ml of the liquid preculture as a main culture and cultured with shaking at 30° C. for 2 days.

To confirm whether the gene introduced in the transformant strains is expressed, cells were collected from the liquid culture and total RNA was purified with RNeasy Mini Kit.

cDNA was synthesized by taking 1 μg of the total RNA and using Super script II reverse transcriptase (Thermo Fisher Scientific) and random hexamers as primers.

To confirm the expression of the transgenes, the following primers were prepared.

```
For confirming expression of UGT35C2
UGT35C2-r1
                                          (SEQ ID NO: 51)
5'-CAAGTCCCCAACCAAATTCCGT-3'

For confirming expression of UGT91D2 and
UGT91D2L3#16
UGT91D1L3-r1:
                                          (SEQ ID NO: 52)
5'-CACGAACCCGTCTGGCAACTC-3'

For confirming expression of UGT74G1
UGT74G1-r1:
                                          (SEQ ID NO: 53)
5'-CCCGTGTGATTTCTTCCACTTGTTC-3'

For confirming expression of UGT76G1
UGT76G1-r1:
                                          (SEQ ID NO: 54)
5'-CAAGAACCCATCTGGCAACGG-3'

GAL10p region (promoter region)
PGAL10-f3:
                                          (SEQ ID NO: 55)
5'-GATTATTAAACTTCTTTGCGTCCATCCA-3'

GAL1p region (promoter region)
PGAl1-f3:
                                          (SEQ ID NO: 56)
5'-CCTCTATACTTTAACGTCAAGGAGAAAAAACC-3'
```

Expression of each transgene was confirmed by performing PCR using the following combinations of primers, the previously synthesized cDNA as a template, and ExTaq (Takara Bio), and each product was confirmed by agarose gel electrophoresis of the products.

```
UGT85C2:UGT85C2-r1 (SEQ ID NO: 51) and
PGAL1-f3 (SEQ ID NO: 56)

UGT91D2 or UGT91D2L3:UGT91D1L3-r1 (SEQ ID NO: 52)
and PGAL10-F3 (SEQ ID NO: 55)

UGT74G1:UGT74G1-r1 (SEQ ID NO: 53) and PGAL1-f3
(SEQ ID NO: 56)

UGT76G1:UGT76G1-r1 (SEQ ID NO: 54) and PGAL10-f3
(SEQ ID NO: 55)
```

This confirmed that the introduced genes were expressed in the transformant strains.

Production of Steviol Glycosides

The culture was conducted under the same conditions as Example 5 above, except that 2 μg of steviol (ChromaDex Inc.) per 1 ml of medium was added to the SG-Trp&Ura&His liquid medium. After completing the culture, the supernatant and bacterial cells were separated by centrifugation of the liquid culture. The culture supernatant was washed with acetonitrile and then loaded on the Sep-Pak C18 column equilibrated with water, washed with 20% acetonitrile and then eluted with 80% acetonitrile, dried, and then dissolved in a little amount of 80% acetonitrile to prepare a glycoside sample. This glycoside sample was subjected to the following analyses.

Analysis by HPLC

The obtained steviol glycosides were analyzed by HPLC. The conditions are as follows.

Column: COSMOSIL $5C_{18}$-AR-II 4.6 mmI.D.×250 mm (Nacalai Tesque, Inc.)

Mobile phase: A; Acetonitrile, B; 10 mM sodium phosphate buffer (pH 2.6)

B conc. 70%→30%, 40 min, linear gradient

Flow rate: 1 ml/min

Temperature: 40° C.

Detection: UV 210 nm

RebC was produced in the strains S1-5678, S1-56R78, S2-5678, and S2-56R78 coexpressing the UDP-rhamnose synthase gene and the steviol glycosylation enzyme gene. The amount of RebC produced in the strain expressing UGT91D2L#16 was higher than that in the strain expressing UGT91D2. The result of expression of UGT91D2L#16 is shown in FIG. 7.

Industrial Applicability

According to the present invention, rhamnose can be produced from glucose using the SrRHM1 and SrRHM2 genes. Moreover, the sweetness and taste quality of a *Stevia rebaudiana* sweetener preparation can be controlled by controlling the content of the steviol glycoside having a rhamnose group. In particular, the gene expression of SrRHM2 is highly related to the presence or absence of rhamnose group-containing steviol glycosides, and it is considered that this gene can be used as a marker for qualitative selection of sugars constituting sweet glycosides of *Stevia rebaudiana* plants. The present invention also provides a molecular tool for producing steviol glycosides having rhamnose groups typified by RebC not only in plants but also in microorganisms by metabolic engineering.

The invention claimed is:

1. A method comprising reacting, outside of a stevia plant, glucose and the protein according to any one selected from the group consisting of the following (a) to (c) to produce rhamnose:
   (a) a protein consisting of the amino acid sequence of SEQ ID NO: 2, 4, 6, 8, or 10;
   (b) a protein consisting of an amino acid sequence wherein 1 to 13 amino acids are deleted, substituted, inserted, or added in the amino acid sequence of SEQ ID NO: 2, 4, 6, 8, or 10 and having an activity to produce rhamnose from glucose;
   (c) a protein having an amino acid sequence having a sequence identity of 98% or more to the amino acid sequence of SEQ ID NO: 2, 4, 6, 8, or 10 and having an activity to produce rhamnose from glucose.

2. The method according to claim 1, wherein:
   the glucose is in the form of uridine diphosphate glucose, or
   the rhamnose is in the form of uridine diphosphate rhamnose.

3. The method of claim 1, further comprising:
   transferring the rhamnose to steviol or a steviol glycoside to produce steviol glycoside.

4. The method according to claim 3, wherein the rhamnose is in the form of uridine diphosphate rhamnose.

5. The method according to claim 3, wherein the transferring of the rhamnose to steviol or a steviol glycoside is performed by using: a host cell comprising (i) a polynucleotide comprising the nucleotide sequence of SEQ ID NO: 11 or 13; or (ii) a polynucleotide encoding a protein having an amino acid sequence having a sequence identity of 90% or more to the amino acid sequence of SEQ ID NO: 12 or 14 and having an activity to add rhamnose to glucose at position 13 in the steviol glycoside via a 1→2 bond.

6. The method according to claim 5, wherein the host cell comprises at least one polynucleotide of the following (a) to (e):
   (a) (i) a polynucleotide comprising the nucleotide sequence of SEQ ID NO: 15; or (ii) a polynucleotide encoding a protein having an amino acid sequence having a sequence identity of 90% or more to the amino acid sequence of SEQ ID NO: 16 and having an activity to add glucose to the hydroxyl group at position 13 in a steviol glycoside;
   (b) (i) a polynucleotide comprising the nucleotide sequence of SEQ ID NO: 17; or (ii) a polynucleotide encoding a protein having an amino acid sequence having a sequence identity of 90% or more to the amino acid sequence of SEQ ID NO: 18 and having an activity to add glucose to the carboxylic acid at position 19 in a steviol glycoside;
   (c) (i) a polynucleotide comprising the nucleotide sequence of SEQ ID NO: 19; or (ii) a polynucleotide encoding a protein having an amino acid sequence having a sequence identity of 90% or more to the amino acid sequence of SEQ ID NO: 20 and having an activity to add glucose at position 3 of the glucose at position 13 in a steviol glycoside via a 1→3 bond;
   (d) (i) a polynucleotide comprising the nucleotide sequence of SEQ ID NO: 11 or 13; or (ii) a polynucleotide encoding a protein having an amino acid sequence having a sequence identity of 90% or more to the amino acid sequence of SEQ ID NO: 12 or 14 and having an activity to add glucose to the glucose at position 19 in a steviol glycoside via a 1→2 bond;
   (e) (i) a polynucleotide comprising the nucleotide sequence of SEQ ID NO: 19; or (ii) a polynucleotide encoding a protein having an amino acid sequence having a sequence identity of 90% or more to the amino acid sequence of SEQ ID NO: 20 and having an activity to add glucose to the glucose at position 19 in a steviol glycoside via a 1→3 bond.

7. The method of claim 1, further comprising:
   adding the produced rhamnose to a raw material of the sweetener, the food or beverage, or the pharmaceutical product; and
   preparing the sweetener, the food or beverage, or the pharmaceutical product.

8. The method according to claim 7, wherein the rhamnose is in the form of uridine diphosphate rhamnose.

* * * * *